(12) United States Patent
Ge et al.

(10) Patent No.: US 7,442,808 B2
(45) Date of Patent: Oct. 28, 2008

(54) ANTIDIABETIC BICYCLIC COMPOUNDS

(75) Inventors: Min Ge, Edison, NJ (US); Jiafang He, Dayton, NJ (US); Fiona Wai Yu Lau, Edgewater, NJ (US); Gui-Bai Liang, Scotch Plains, NJ (US); Songnian Lin, Monroe, NJ (US); Weiguo Liu, Princeton, NJ (US); Shawn P. Walsh, Bridgewater, NJ (US); Lihu Yang, Edison, NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 11/801,841

(22) Filed: May 11, 2007

(65) Prior Publication Data

US 2007/0265332 A1   Nov. 15, 2007

Related U.S. Application Data

(60) Provisional application No. 60/800,542, filed on May 15, 2006, provisional application No. 60/836,308, filed on Aug. 8, 2006.

(51) Int. Cl.
| | |
|---|---|
| *C07D 495/00* | (2006.01) |
| *C07D 307/92* | (2006.01) |
| *C07D 209/94* | (2006.01) |
| *C07D 209/00* | (2006.01) |
| *C07C 229/00* | (2006.01) |
| *C07C 62/00* | (2006.01) |
| *A61K 31/38* | (2006.01) |
| *A61K 31/34* | (2006.01) |
| *A61K 31/19* | (2006.01) |
| *A61K 31/195* | (2006.01) |
| *A61K 31/40* | (2006.01) |

(52) U.S. Cl. .......... 549/44; 549/458; 548/439; 548/448; 562/452; 562/466; 514/443; 514/468; 514/411; 514/569; 514/567

(58) Field of Classification Search .......... 549/44, 549/458; 548/439, 448; 514/443, 468, 569, 514/567, 411; 562/452, 466
See application file for complete search history.

(56) References Cited

U.S. PATENT DOCUMENTS

| 3,514,491 A | 5/1970 | Hanessian et al. |
| 2003/0069224 A1 * | 4/2003 | Lindstrom et al. .......... 514/217 |

FOREIGN PATENT DOCUMENTS

| WO | WO 02/070516 | 9/2002 |
| WO | WO 03/020705 | 3/2003 |
| WO | WO 2004/021969 | 3/2004 |
| WO | WO 2005/066131 | 7/2005 |

* cited by examiner

*Primary Examiner*—Kamal Saeed
*Assistant Examiner*—Kristin Bianchi
(74) *Attorney, Agent, or Firm*—Phillippe L. Durette; Catherine D. Fitch

(57) ABSTRACT

Tricyclic compounds containing a cyclopropyl carboxylic acid or carboxylic acid derivative (e.g. amide) fused to a bicyclic ring, including pharmaceutically acceptable salts and prodrugs thereof, are agonists of G-protein coupled receptor 40 (GPR40) and are useful as therapeutic compounds, particularly in the treatment of Type 2 diabetes mellitus, and of conditions that are often associated with this disease, including obesity and lipid disorders, such as mixed or diabetic dyslipidemia, hyperlipidemia, hypercholesterolemia, and hypertriglyceridemia.

13 Claims, 3 Drawing Sheets

ANTIDIABETIC BICYCLIC COMPOUNDS

CROSS REFERENCE TO RELATED APPLICATIONS

This application claims priority under 35 U.S.C. § 119 (e) from U.S. Application No. 60/800,542, filed May 15, 2006, and U.S. Application No. 60/836,308, filed Aug. 8, 2006.

FIELD OF THE INVENTION

The instant invention is concerned with tricyclic compounds containing a cyclopropyl carboxylic acid or carboxylic acid derivative fused to a bicyclic ring, including pharmaceutically acceptable salts and prodrugs thereof, which are agonists of G-protein coupled receptor 40 (GPR40) and are useful as therapeutic compounds, particularly in the treatment of Type 2 diabetes mellitus, and of conditions that are often associated with this disease, including obesity and lipid disorders.

BACKGROUND OF THE INVENTION

Diabetes is a disease derived from multiple causative factors and characterized by elevated levels of plasma glucose (hyperglycemia) in the fasting state or after administration of glucose during an oral glucose tolerance test. There are two generally recognized forms of diabetes. In type 1 diabetes, or insulin-dependent diabetes mellitus (IDDM), patients produce little or no insulin, the hormone which regulates glucose utilization. In type 2 diabetes, or noninsulin-dependent diabetes mellitus (NIDDM), insulin is still produced in the body. Patients having type 2 diabetes have a resistance to the effects of insulin in stimulating glucose and lipid metabolism in the main insulin-sensitive tissues, which are muscle, liver and adipose tissues. These patients often have normal levels of insulin, and may have hyperinsulinemia (elevated plasma insulin levels), as they compensate for the reduced effectiveness of insulin by secreting increased amounts of insulin. Insulin resistance is not primarily caused by a diminished number of insulin receptors but rather by a post-insulin receptor binding defect that is not yet completely understood. This lack of responsiveness to insulin results in insufficient insulin-mediated activation of uptake, oxidation and storage of glucose in muscle, and inadequate insulin-mediated repression of lipolysis in adipose tissue and of glucose production and secretion in the liver.

Persistent or uncontrolled hyperglycemia that occurs with diabetes is associated with increased and premature morbidity and mortality. Often abnormal glucose homeostasis is associated both directly and indirectly with obesity, hypertension, and alterations of the lipid, lipoprotein and apolipoprotein metabolism, as well as other metabolic and hemodynamic disease. Patients with type 2 diabetes mellitus have a significantly increased risk of macrovascular and microvascular complications, including atherosclerosis, coronary heart disease, stroke, peripheral vascular disease, hypertension, nephropathy, neuropathy, and retinopathy. Therefore, therapeutic control of glucose homeostasis, lipid metabolism, obesity, and hypertension are critically important in the clinical management and treatment of diabetes mellitus.

Patients who have insulin resistance often have several symptoms that together are referred to as syndrome X, or the metabolic syndrome. According to one widely used definition, a patient having metabolic syndrome is characterized as having three or more symptoms selected from the following group of five symptoms: (1) abdominal obesity; (2) hypertriglyceridemia; (3) low high-density lipoprotein cholesterol (HDL); (4) high blood pressure; and (5) elevated fasting glucose, which may be in the range characteristic of Type 2 diabetes if the patient is also diabetic. Each of these symptoms is defined clinically in the Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670. Patients with metabolic syndrome, whether or not they have or develop overt diabetes mellitus, have an increased risk of developing the macrovascular and microvascular complications that occur with type 2 diabetes, such as atherosclerosis and coronary heart disease.

There are several available treatments for type 2 diabetes, each of which has its own limitations and potential risks. Physical exercise and a reduction in dietary intake of calories often dramatically improve the diabetic condition and are the usual recommended first-line treatment of type 2 diabetes and of pre-diabetic conditions associated with insulin resistance. Compliance with this treatment is very poor because of well-entrenched sedentary lifestyles and excess food consumption, especially of foods containing high amounts of fat and carbohydrates. Pharmacologic treatments have focused on three areas of pathophysiology: (1) Hepatic glucose production (biguanides), (2) insulin resistance (PPAR agonists), and (3) insulin secretion.

The biguanides are a class of drugs that are widely used to treat type 2 diabetes. The two best known biguanides, phenformin and metformin, cause some correction of hyperglycemia. The biguanides act primarily by inhibiting hepatic glucose production, and they also are believed to modestly improve insulin sensitivity. The biguanides can be used as monotherapy or in combination with other anti-diabetic drugs, such as insulin or an insulin secretagogue, without increasing the risk of hypoglycemia. However, phenformin and metformin can induce lactic acidosis and nausea/diarrhea. Metformin has a lower risk of side effects than phenformin and is widely prescribed for the treatment of Type 2 diabetes.

The glitazones (i.e. 5-benzylthiazolidine-2,4-diones) are a newer class of compounds that can ameliorate hyperglycemia and other symptoms of type 2 diabetes. The glitazones that are currently marketed (rosiglitazone and pioglitazone) are agonists of the peroxisome proliferator activated receptor (PPAR) gamma subtype. The PPAR-gamma agonists substantially increase insulin sensitivity in muscle, liver and adipose tissue in several animal models of type 2 diabetes, resulting in partial or complete correction of elevated plasma glucose levels without the occurrence of hypoglycemia. PPAR-gamma agonism is believed to be responsible for the improved insulin sensititization that is observed in human patients who are treated with the glitazones. New PPAR agonists are currently being developed. Many of the newer PPAR compounds are agonists of one or more of the PPAR alpha, gamma and delta subtypes. Compounds that are agonists of both the PPAR alpha and PPAR gamma subtypes (PPAR alpha/gamma dual agonists) have been made and tested, but so far none have been approved by the regulatory authorities. The currently marketed PPAR gamma agonists are modestly effective in reducing plasma glucose and HemoglobinA1C. The currently marketed compounds do not greatly improve lipid metabolism and may actually have a negative effect on the lipid profile. Selective PPAR Gamma Partial Agonists (SPPARM's) are currently being developed and may be equally effective, with fewer side effects, such as weight gain and edema. Thus, the PPAR compounds represent an important advance in diabetic therapy.

Another widely used drug treatment involves the administration of insulin secretagogues, such as the sulfonylureas (e.g. tolbutamide and glipizide). These drugs increase the plasma level of insulin by stimulating the pancreatic β-cells to secrete more insulin. Insulin secretion in the pancreatic β-cell is under strict regulation by glucose and an array of metabolic, neural and hormonal signals. Glucose stimulates insulin production and secretion through its metabolism to generate ATP and other signaling molecules, whereas other extracellular signals act as potentiators or inhibitors of insulin secretion through GPCR's present on the plasma membrane. Sulfonylureas and related insulin secretagogues act by blocking the ATP-dependent K+ channel in β-cells, which causes depolarization of the cell and the opening of the voltage-dependent Ca2+ channels with stimulation of insulin release. This mechanism is non-glucose dependent, and hence insulin secretion can occur regardless of the ambient glucose levels. This can cause insulin secretion even if the glucose level is low, resulting in hypoglycemia, which can be fatal in severe cases. The administration of insulin secretagogues must therefore be carefully controlled. The insulin secretagogues are often used as a first-line drug treatment for Type 2 diabetes.

Dipeptidyl peptidase IV (DPP-4) inhibitors (e.g., sitagliptin, vildagliptin, alogliptin, denagliptin, and saxagliptin) provide a new route for increasing insulin secretion in response to food consumption. Dipeptidyl peptidase IV (DPP-4) is a cell surface protein with broad tissue distribution that has been implicated in a wide range of biological functions. DPP-4 is identical to the T cell activation marker CD26 and can cleave a number of immunoregulatory, endocrine, and neurological peptides in vitro. It is well established that the incretins GLP-1 (glucagon-like peptide-1) and GIP (glucose-dependent insulinotropic peptide; also known as gastric inhibitory peptide) stimulate insulin secretion and are rapidly inactivated in vivo by DPP-4. These peptidyl hormones are secreted by endocrine cells that are located in the epithelium of the small intestine. When these endocrine cells sense an increase in the concentration of glucose in the lumen of the digestive tract, they act as the trigger for incretin release. Incretins are carried through the circulation to beta cells in the pancreas and cause the beta cells to secrete more insulin in anticipation of an increase of blood glucose resulting from the digesting meal. Studies with DPP-4(−/−)-deficient mice and clinical trials with DPP-4 inhibitors indicate that DPP-4 inhibition increases the steady state concentrations of GLP-1 and GIP, resulting in improved glucose tolerance. Inactivation of these peptides by DPP-4 may also play a role in glucose homeostasis. DPP-4 inhibitors therefore have utility in the treatment of type2 diabetes and in the treatment and prevention of the numerous conditions that often accompany type 2 diabetes, including metabolic syndrome, reactive hypoglycemia, and diabetic dyslipidemia. GLP-1 has other effects that help to lower blood glucose and contribute to glucose homeostasis. GLP-1 inhibits glucagon secretion from the liver. Glucagon is a hormone that increases blood glucose levels by stimulating glucose production from glycogen stores in the liver. GLP-1 also delays stomach emptying, which helps to spread glucose absorption out over time, and thus limit hyperglycemia. Also, studies in animals have shown that GLP-1 can increase the number of beta cells, either through promoting growth or by inhibiting apoptosis. Thus, potentiation of GLP-1 action by preventing its degradation offers several mechanisms to attenuate hyperglycemia associated with type 2 diabetes.

There has been a renewed focus on pancreatic islet-based insulin secretion that is controlled by glucose-dependent insulin secretion. This approach has the potential for stabilization and restoration of β-cell function. In this regard, several orphan G-protein coupled receptors (GPCR's) have recently been identified that are preferentially expressed in the β-cell and that are implicated in glucose stimulated insulin secretion (GSIS). GPR40 is a cell-surface GPCR that is highly expressed in human (and rodent) islets as well as in insulin-secreting cell lines. Several naturally-occurring medium to long-chain fatty acids (FA's) as well as synthetic compounds, including several members of the thiazolidinedione class of PPARγ agonists, have recently been identified as ligands for GPR40 (Itoh, Y. et al., Nature. 422: 173 [2003]; Briscoe, C. P. et al., J. Biol. Chem. 278: 11303 [2003]; Kotarsky, K. et al., Biochem. Biophys. Res. Comm. 301: 406 [2003]. Under hyperglycemic conditions, GPR40 agonists are capable of augmenting the release of insulin from islet cells. The specificity of this response is suggested by results showing that the inhibition of GPR40 activity by siRNA attenuates FA-induced amplification of GSIS. These findings indicate that, in addition to the intracellular generation of lipid-derivatives of FA's that are thought to promote insulin release, FA's (and other synthetic GPR40 agonists) may also act as extracellular ligands that bind to GPR40 in mediating FA-induced insulin secretion. There are several potential advantages of GPR40 as a potential target for the treatment of type 2 diabetes. First, since GPR40-mediated insulin secretion is glucose dependent, there is little or no risk of hypoglycemia. Second, the limited tissue distribution of GPR40 (mainly in islets) suggests that there would be less chance for side effects associated with GPR40 activity in other tissues. Third, GPR40 agonists that are active in the islets may have the potential to restore or preserve islet function. This would be highly advantageous, because long term diabetes therapy often leads to the gradual diminution of islet activity, so that after extended periods of treatment, it is often necessary to treat type 2 diabetic patients with daily insulin injections. By restoring or preserving islet function, GPR40 agonists may delay or prevent the diminution and loss of islet function in a type 2 diabetic patient.

SUMMARY OF THE INVENTION

The class of compounds described herein is a new class of GPR40 agonists. The compounds are useful in the treatment of diseases that are modulated by GPR40 agonists, including type 2 diabetes, hyperglycemia that may be associated with type 2 diabetes or pre-diabetic insulin resistance, and also obesity.

The present invention is directed to a compound of formula I, or a pharmaceutically acceptable salt thereof, including individual diastereomers and enantiomers thereof, and mixtures of diastereomers and/or enantiomers thereof:

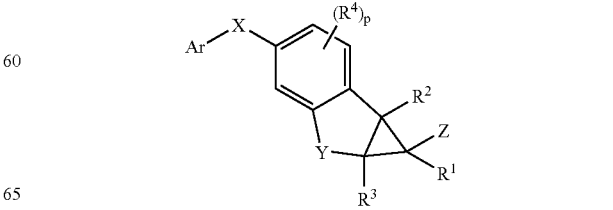

In Formula I, Ar is selected from the group consisting of phenyl, naphthyl, a 5-6 membered monocyclic heteroaromatic ring having 1-3 heteroatoms independently selected from N, O, and S, and a benzoheteroaromatic group comprising a phenyl ring fused to a 5-6 membered heteroaromatic ring having 1-3 heteroatoms independently selected from N, O and S.

Ar in Formula I is optionally substituted with 1-2 aromatic groups independently selected from phenyl, phenoxy, benzyl, and a 5-6 membered heteroaromatic ring having 1-3 heteroatoms independently selected from N, O and S and is optionally substituted with 1-5 substituents independently selected from halogen, —CN, —NO$_2$, —OH, —C(=O)H, —C(=O)OH, $C_{1-6}$alkyl, —$C_{3-6}$cycloalkyl, —O$C_{1-6}$alkyl, —S$C_{1-6}$alkyl, —C(=O)$C_{1-6}$alkyl, —OC(=O)$C_{1-6}$alkyl, —C(=O)O$C_{1-6}$alkyl, —S(O)$_2C_{1-6}$alkyl, —NR$^{13}$R$^{14}$, —C(=O)N(R$^{13}$)(R$^{14}$), —S(O)$_2$NR$^{13}$R$^{14}$, and —O$C_{3-6}$cycloalkyl, wherein (a) $C_{1-6}$alkyl in all instances is optionally substituted with 1-5 halogens and optionally 1 group selected from —OH and —O$C_{1-4}$alkyl optionally substituted with 1-5 halogens, (b) —$C_{3-6}$cycloalkyl in all instances is optionally substituted with 1-2 substituents independently selected from halogen and CH$_3$, and (c) the aromatic substituent groups phenyl, phenoxy, benzyl, and the 5-6 membered heteroaromatic ring having 1-3 heteroatoms independently selected from N, O and S are optionally substituted with 1-5 groups independently selected from halogen, —CN, —NO$_2$, —OH, —C(=O)H, —C(=O)OH, $C_{1-6}$alkyl, —O$C_{1-6}$alkyl, —S$C_{1-6}$ alkyl, —C(=O)$C_{1-6}$alkyl, —OC(=O)$C_{1-6}$alkyl, —C(=O)O$C_{1-6}$alkyl, —S(O)$_2C_{1-6}$alkyl, NR$^{13}$R$^{14}$, —C(=O)N(R$^{13}$)(R$^{14}$), —S(O)$_2$NR$^{13}$R$^{14}$, and —O(CH$_2$)$_q$ (4-6 membered heterocycle having 1-2 heteroatoms independently selected from O, S and N), wherein $C_{1-6}$alkyl in all instances is optionally substituted with 1-5 halogens and optionally 1 group selected from —OH and —O$C_{1-4}$alkyl optionally substituted with 1-5 halogens, and the 4-6 membered heterocycle having 1-2 heteroatoms independently selected from O, S and N is optionally substituted with 1-2 groups independently selected from halogen, CH$_3$, and CF$_3$;

X is selected from the group consisting of —O—, —S—, —S(O)—, —S(O)$_2$—, —NR$^5$—, —OCR$^{10}$R$^{11}$—, —SCR$^{10}$R$^{11}$, —NR$^5$CR$^{10}$R$^{11}$—, —CR$^{10}$R$^{11}$—, —CR$^{10}$R$^{11}$S—, —CR$^{10}$R$^{11}$NR$^5$—, and —CR$^6$R$^7$CR$^8$R$^9$O—;

Y is selected from the group consisting of —O—, —S—, —S(O)—, —S(O)$_2$—, —NR$^5$—, —C(=O)—, —CR$^6$R$^7$—, —OCR$^6$R$^7$—, —SCR$^6$R$^7$—, and —CR$^6$R$^7$CR$^8$R$^9$—;

Z is selected from the group consisting of —C(=O)OR$^{12}$, C(=O)NR$^{13}$R$^{14}$, and 5-tetrazolyl;

R$^1$, R$^2$, and R$^3$ are each independently selected from the group consisting of H, halogen, $C_{1-3}$alkyl, and —O$C_{1-3}$alkyl, wherein $C_{1-3}$alkyl, and —O$C_{1-3}$alkyl are each optionally substituted with 1-3 halogens;

R$^4$ is selected from the group consisting of halogen, —CN, —NO$_2$, —OH, —C(=O)H, —C(=O)OH, $C_{1-6}$alkyl, —O$C_{1-6}$alkyl, —S$C_{1-6}$alkyl, —C(=O)$C_{1-6}$alkyl, —OC(=O)$C_{1-6}$alkyl, —C(=O)O$C_{1-6}$alkyl, —S(O)$_2C_{1-6}$alkyl, —NR$^{13}$R$^{14}$, —C(=O)N(R$^{13}$)(R$^{14}$), and —S(O)$_2$NR$^{13}$R$^{14}$, wherein $C_{1-6}$alkyl in all instances is optionally substituted with 1-5 halogens;

R$^5$, R$^{13}$ and R$^{14}$ are each independently selected from the group consisting of H, $C_{1-5}$alkyl, —C(=O)$C_{1-5}$alkyl, and —S(O)$_2C_{1-5}$alkyl, wherein $C_{1-5}$alkyl in all instances is optionally substituted with 1-5 halogens;

R$^6$, R$^7$, R$^8$, R$^9$, R$^{10}$, and R$^{11}$ are each independently selected from the group consisting of H, halogen, —OH, and $C_{1-3}$alkyl which is optionally substituted with 1-5 halogens;

R$^{12}$ is selected from the group consisting of H and $C_{1-7}$alkyl which is optionally substituted with 1-5 halogens;

p is an integer from 0-3; and q is 0 or 1.

Alkyl groups, including the alkyl portion of other substituent groups, such as alkoxy, are linear or branched, unless otherwise defined.

DETAILED DESCRIPTION OF THE INVENTION

Figure 1:
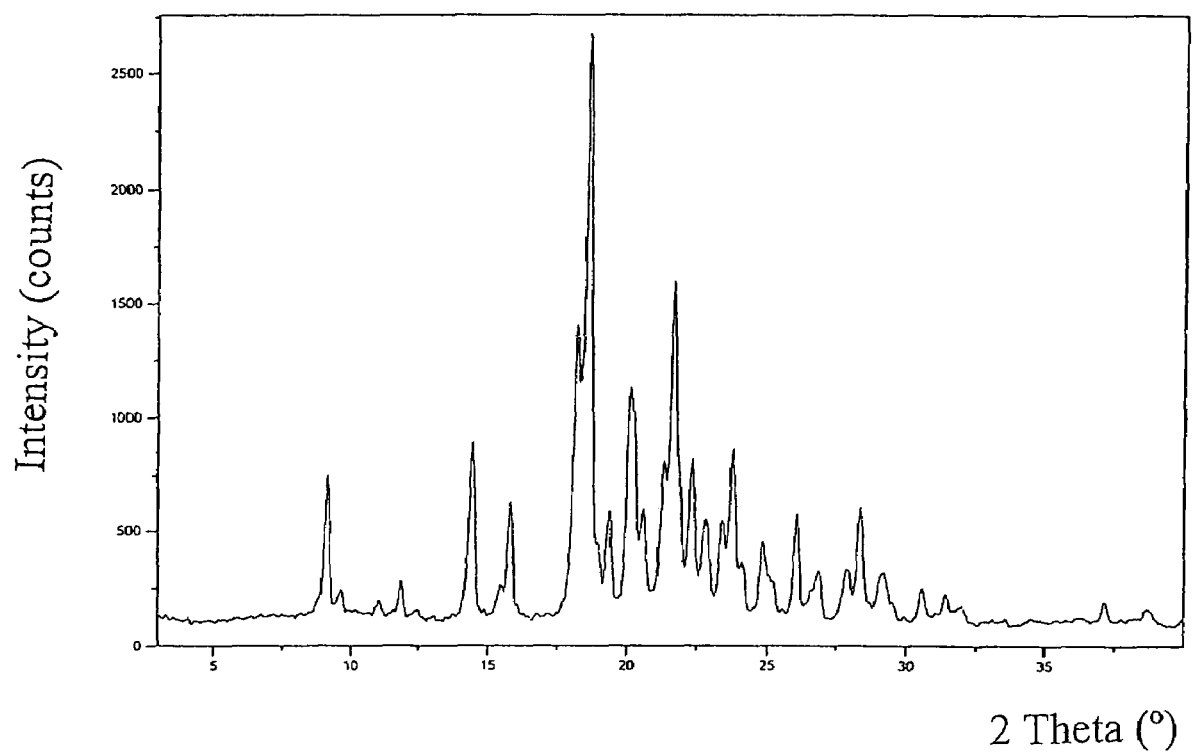
FIG. 1 is a characteristic X-ray diffraction pattern of the crystalline anhydrous free acid of Example 3.

The invention has numerous embodiments, which are summarized below. The invention includes the compounds as shown, and also includes individual diastereomers, enantiomers, and epimers of the compounds, and mixtures of diastereomers and/or enantiomers thereof including racemic mixtures. The invention also includes pharmaceutically acceptable salts of the compounds, and pharmaceutical compositions comprising the compounds and a pharmaceutically acceptable carrier. The compounds are especially useful in treating insulin resistance, type 2 diabetes, and dyslipidemia that is associated with type 2 diabetes and insulin resistance.

One embodiment relates to the compound of Formula I, or a pharmaceutically acceptable salt thereof, wherein Ar is selected from the group consisting of phenyl, naphthyl, and a 5-6 membered monocyclic heteroaromatic ring having 1-3 heteroatoms independently selected from N, O, and S, wherein Ar is optionally substituted with one aromatic group selected from phenyl, phenoxy, and a 5-6 membered heteroaromatic ring having 1-3 heteroatoms independently selected from N, O and S and is optionally substituted with 1-3 substituents independently selected from halogen, —CN, —NO$_2$, —OH, —C(=O)H, —C(=O)OH, $C_{1-5}$alkyl, —$C_{3-6}$cycloalkyl, —O$C_{1-3}$alkyl, —S$C_{1-3}$alkyl, —C(=O)$C_{1-3}$alkyl, —OC(=O)$C_{1-3}$alkyl, —C(=O)O$C_{1-3}$alkyl, —S(O)$_2C_{1-3}$alkyl, —NR$^{13}$R$^{14}$, —C(=O)N(R$^{13}$)(R$^{14}$), —S(O)$_2$NR$^{13}$R$^{14}$, and —O$C_{3-6}$cycloalkyl, wherein (a) $C_{1-3}$alkyl in all instances is optionally substituted with 1-5 halogens and optionally 1 group selected from —OH and —O$C_{1-3}$alkyl optionally substituted with 1-5 halogens, (b) $C_{1-5}$alkyl is optionally substituted with 1-5 halogens, (c) —$C_{3-6}$cycloalkyl in all instances is optionally substituted with 1-2 substituents independently selected from halogen and CH$_3$, and (d) the aromatic substituent group selected from phenyl, phenoxy, and the 5-6 membered heteroaromatic ring having 1-3 heteroatoms independently selected from N, O and S is optionally substituted with 1-3 groups independently selected from halogen, —CN, —NO$_2$, —OH, —C(=O)H, —C(=O)OH, $C_{1-5}$alkyl, —O$C_{1-3}$alkyl, —S$C_{1-3}$alkyl, —C(=O)$C_{1-3}$alkyl, —OC(=O)$C_{1-3}$alkyl, —C(=O)O$C_{1-3}$alkyl, —S(O)$_2C_{1-3}$alkyl, NR$^{13}$R$^{14}$, —C(=O)N(R$^{13}$)(R$^{14}$), —S(O)$_2$NR$^{13}$R$^{14}$, and —O(CH$_2$)$_q$(4-6 membered heterocycle having 1-2 heteroatoms independently selected from O, S and N), wherein $C_{1-3}$alkyl in all instances is optionally substituted with 1-5 halogens and optionally 1 group selected from —OH and —O$C_{1-3}$alkyl optionally substituted with 1-5 halogens, $C_{1-5}$alkyl is optionally substituted with 1-5 halogens, and the 4-6 membered heterocycle having 1-2 heteroatoms independently selected from O, S and N is optionally substituted with 1-2 groups independently selected from halogen, $CH_3$, and $CF_3$.

Another embodiment relates to the compound of Formula I, or a pharmaceutically acceptable salt thereof, wherein Ar is selected from the group consisting of phenyl, naphthyl, quinolyl, pyridyl, and thiazolyl, which is optionally substituted with one aromatic group selected from phenyl, phenoxy, and oxadiazolyl, and is optionally substituted with 1-3 groups independently selected from halogen, —CN, —$NO_2$, $C_{1-4}$alkyl, —$OC_{1-2}$alkyl, and —$OC_{3-6}$cycloalkyl, wherein $C_{1-4}$alkyl and —$OC_{1-2}$alkyl are optionally substituted with 1-5 halogens, and the substituents phenyl, phenoxy, and oxadiazolyl are optionally substituted with 1-3 groups independently selected from halogen, —CN, —$NO_2$, —OH, —C(=O)OH, $C_{1-4}$alkyl, —$OC_{1-4}$alkyl, and —$O(CH_2)_q$(4-6 membered cyclic ether), wherein $C_{1-4}$alkyl in all instances is optionally substituted with 1-5 halogens and is optionally substituted with 1 group selected from —OH and —$OC_{1-3}$alkyl optionally substituted with 1-5 halogens, and the 4-6 membered cyclic ether is optionally substituted with 1-2 groups independently selected from halogen, $CH_3$, and $CF_3$. A 4-6-membered cyclic ether means a monoether. Examples are oxetane, tetrahydrofuran, and tetrahydropyran.

In subgroups of the compound as described above, $R^1$, $R^2$, and $R^3$ are each independently selected from the group consisting of H, F, Cl, $C_{1-3}$alkyl, and $CF_3$.

In subgroups of the compound as described above, $R^4$ is selected from the group consisting of halogen, —CN, —$NO_2$, —OH, —C(=O)H, —C(=O)OH, $C_{1-4}$alkyl, —$OC_{1-4}$alkyl, —C(=O)$C_{1-4}$alkyl, and —$NR^{13}R^{14}$, wherein $C_{1-4}$alkyl in all instances is optionally substituted with 1-5 halogens.

In subgroups of the compound as described above, $R^5$ is selected from the group consisting of H, $C_{1-3}$alkyl, and —C(=O)$C_{1-3}$alkyl, wherein $C_{1-3}$alkyl and —C(=O)$C_{1-3}$alkyl are optionally substituted with 1-5 F.

In subgroups of the compound as described above, $R^6$, $R^8$, and $R^{10}$ are each independently selected from the group consisting of H, —OH, and $CH_3$.

In subgroups of the compound as described above, $R^7$, $R^9$, and $R^{11}$ are each independently selected from the group consisting of H and $CH_3$.

In subgroups of the compound as described above, $R^{13}$ and $R^{14}$ are each independently selected from the group consisting of H, $C_{1-5}$alkyl, and —$S(O)_2C_{1-5}$alkyl.

In subgroups of the compound as described above, p is 0 or 1.

In subgroups of the compound of Formula I, or a pharmaceutically acceptable salt thereof, X is selected from the group consisting of —O—, —S—, —S(O)—, —$S(O)_2$—, —$CHR^{11}O$—, —$CH_2NH$—, —$CH_2CH_2O$—, and —$OCH_2$—.

In subgroups as described above, Y is selected from the group consisting of —S—, —S(O)—, —$S(O)_2$—, —O—, —$OCH_2$—, —C(=O)—, —$CHR^6$—, —$NR_5$—, and —$CH_2CH_2$—.

In subgroups as described above, Z is selected from the group consisting of —C(=O)$OR^{12}$ and —C(=O)$NR^{13}R^{14}$.

In subgroups as described above, $R^1$, $R^2$, and $R^3$ are each independently selected from the group consisting of H, $CH_3$, and $CF_3$.

In subgroups as described above, $R^4$ is selected from the group consisting of halogen, $CH_3$, and $CF_3$.

In subgroups as described above, $R^5$ is selected from the group consisting of H and $CH_3$.

In subgroups as described above, $R^6$ is selected from the group consisting of H and —OH.

In subgroups as described above, $R^{11}$ is selected from H and $CH_3$.

In subgroups as described above, $R^{12}$ is selected from the group consisting of H and $C_{1-5}$alkyl which is optionally substituted with 1-5 halogens.

In subgroups as described above, $R^{13}$ is selected from the group consisting of H, $C_{1-3}$alkyl, and —$S(O)_2C_{1-3}$alkyl.

In subgroups as described above, $R^{14}$ is H.

In subgroups as described above, p is 0.

A preferred subgroup comprises compounds of Formula I, wherein Ar is selected from the group consisting of phenyl, naphthyl, pyridyl, and thiazolyl, and Ar is optionally substituted with one aromatic group selected from phenyl, phenoxy, and oxadiazolyl, and is optionally substituted with 1-3 groups independently selected from halogen, —CN, —$NO_2$, $C_{1-4}$alkyl, —$OC_{1-2}$alkyl, and —$OC_{3-6}$cycloalkyl, wherein $C_{1-4}$alkyl and —$OC_{1-2}$alkyl are optionally substituted with 1-5 halogens, and the substituents phenyl, phenoxy, and oxadiazolyl are optionally substituted with 1-3 groups independently selected from halogen, —CN, —$NO_2$, —OH, $C_{1-3}$alkyl, —$OC_{1-3}$alkyl, and —$O(CH_2)_q$(4-6 membered cyclic ether), wherein $C_{1-3}$alkyl is optionally substituted with 1-3 halogens, and —$OC_{1-3}$alkyl is optionally substituted with 1-3 halogens and is optionally substituted with 1 group selected from —OH and —$OC_{1-3}$alkyl optionally substituted with 1-3 halogens, and the 4-6 membered cyclic ether is optionally substituted with 1-2 groups independently selected from halogen, $CH_3$, and $CF_3$;

X is selected from the group consisting of —O—, —$CHR^{11}O$—, —$CH_2NH$—, —$OCH_2$—, and —$CH_2CH_2O$—;

Y is selected from the group consisting of —S—, —$S(O)_2$—, —O—, —$OCH_2$—, —C(=O)—, —$CHR^6$—, and —$CH_2CH_2$—;

Z is selected from the group consisting of —C(=O)$OR^{12}$, —C(=O)$NR^{13}R^{14}$, and 5-tetrazolyl;

$R^1$, $R^2$, and $R^3$ are each independently selected from the group consisting of H and $CH_3$;

$R^6$ is selected from the group consisting of H and —OH;

$R^{11}$ is selected from H and $CH_3$;

$R^{12}$ is H;

$R^{13}$ is selected from the group consisting of H, $C_{1-3}$alkyl, and —$S(O)_2C_{1-3}$alkyl;

$R^{14}$ is H;

p is 0; and q is 0 or 1.

In subgroups of the compounds described herein, Z is selected from the group consisting of —C(=O)$OR^{12}$ and —C(=O)$NR^{13}R^{14}$.

In preferred subgroups of compounds, Ar is substituted with 1-3 substituent groups.

In preferred subgroups of compounds, p is 0.

In subgroups of the compounds described herein, Ar is selected from the group consisting of (a) phenyl, which is optionally substituted with 1-3 groups independently selected from halogen, —CN, —$NO_2$, $C_{1-4}$alkyl, —$OC_{1-2}$alkyl, and —$OC_{3-6}$cycloalkyl, wherein $C_{1-4}$alkyl and —$OC_{1-2}$alkyl are optionally substituted with 1-3 halogens; and is optionally substituted with one group selected from (i) phenyl, which is optionally substituted with 1-3 substituents independently selected from halogen, —CN, —$NO_2$, $CH_3$, —$OCH_3$, $CF_3$, —$OCF_3$, —$OCHF_2$, —$OCH_2CH_2OC_{1-2}$alkyl, and —$O(CH_2)_q$(4-6 membered cyclic ether selected from oxetane and tetrahydropyran), wherein the 4-6 membered cyclic ether is optionally substituted with 1 group selected from halogen, $CH_3$, and $CF_3$; (ii) phenoxy, which is optionally substituted with 1-3 groups independently selected from $CH_3$, $CF_3$, and halogen; and (iii) 1,2,4-oxadiazol-3-yl, which is optionally substituted with 1-2 $CH_3$ groups;

(b) naphthyl, which is optionally substituted with 1-2 groups independently selected from $CH_3$, $CF_3$, halogen, and —CN;

(c) pyridyl, which is optionally substituted with 1-2 groups independently selected from $CH_3$, $CF_3$, and halogen; and (d) 1,3-thiazol-5-yl, which is optionally substituted with 1-2 substituents independently selected from phenyl, $CH_3$, and halogen.

In subgroups of the compounds described herein, X is selected from the group consisting of —O—, —$CH_2O$—, —$CH(CH_3)O$—, —$CH_2CH_2O$—, —$CH_2NH$—, and —$OCH_2$—.

In subgroups of the compounds described herein, Y is selected from the group consisting of —S—, —$S(O)_2$—, —O—, —$OCH_2$—, —C(=O)—, —CH(OH)—, —$CH_2$—, and —$CH_2CH_2$—.

In subgroups of the compounds described herein, Z is selected from the group consisting of —C(=O)OH, —C(=O)$NR^{13}R^{14}$, and 5-tetrazolyl.

In subgroups of the compounds described herein, Z is selected from the group consisting of —C(=O)OH and —C(=O)$NR^{13}R^{14}$.

In subgroups of the compounds described herein, $R^1$, $R^2$, and $R^3$ are each independently selected from the group consisting of H and $CH_3$.

In subgroups of the compounds described herein, $R^{13}$ is selected from the group consisting of H, $C_{1-3}$alkyl, and —$S(O)_2C_{1-3}$alkyl.

In subgroups of the compounds described herein, $R^{14}$ is H.

In subgroups of the compounds described herein, p is 0.

In a subgroup of the compounds described herein, Ar is phenyl, which is optionally substituted with 1-3 groups independently selected from halogen, —CN, —$NO_2$, $C_{1-4}$alkyl, $CF_3$, —$OCF_3$, —$OCHF_2$, —$OC_{1-2}$alkyl, and —O-cyclopropyl; and is optionally substituted with one group selected from (i) phenyl, which is optionally substituted with 1-3 substituents independently selected from halogen, —CN, —$NO_2$, $CH_3$, —$OCH_3$, $CF_3$, —$OCF_3$, —$OCH_2CH_2OC_{1-2}$alkyl, and —$O(CH_2)_q$(4-6 membered cyclic ether selected from oxetane and tetrahydropyran), wherein the 4-6 membered cyclic ether is optionally substituted with 1 group selected from $CH_3$, and $CF_3$; (ii) phenoxy, which is optionally substituted with 1-3 groups independently selected from $CH_3$, $CF_3$, and halogen; and (iii) 1,2,4-oxadiazol-3-yl, which is optionally substituted with 1-2 $CH_3$ groups.

In subgroups of the compounds described herein, X is selected from the group consisting of —O— and —$CH_2O$—. In other subgroups, X is 0.

In subgroups of the compounds described herein, Y is 0.

In subgroups of the compounds described herein, Z is selected from the group consisting of —C(=O)OH and —C(=O)$NR^{13}R^{14}$. In other subgroups, Z is —C(=O)OH.

In subgroups of the compounds described herein, $R^{13}$ is selected from the group consisting of H, $CH_3$, and —$S(O)_2CH_3$.

In subgroups of the compounds described herein, $R^{14}$ is H.

In subgroups of the compounds described herein, Ar is phenyl, which is optionally substituted with 1-3 groups independently selected from halogen, —CN, —$NO_2$, $C_{1-4}$alkyl, $CF_3$, —$OCF_3$, —$OCHF_2$, —$OC_{1-2}$alkyl, and —O-cyclopropyl, and is optionally substituted with one phenyl group, which is optionally substituted with 1-3 substituents independently selected from halogen, —CN, —$NO_2$, $CH_3$, —$OCH_3$, $CF_3$, —$OCF_3$, —$OCH_2CH_2OC_{1-2}$alkyl, and —$O(CH_2)_q$(4-6 membered cyclic ether selected from oxetane and tetrahydropyran), wherein the 4-6 membered cyclic ether is optionally substituted with 1 group selected from $CH_3$, and $CF_3$.

Although the specific stereochemistries described above are preferred, other stereoisomers, including diastereomers, enantiomers, epimers, and mixtures of these may also have utility in treating GPR40 mediated diseases. Inactive or less active diastereoisomers and enantiomers are useful for scientific studies relating to the receptor and the mechanism of activation.

Structures of specific compounds and synthetic methods and Schemes for making the compounds are disclosed in the following Examples. Where synthetic details are not provided in the examples, the compounds are readily made by a person of ordinary skill in the art of medicinal chemistry or synthetic organic chemistry by applying the Schemes and synthetic information provided herein. Where a stereochemical center is not defined, the structure represents a mixture of stereoisomers at that center. For such compounds, the individual stereoisomers, including enantiomers, diastereomers, and mixtures of these are also compounds of the invention. The compounds of the invention include pharmaceutically acceptable salts.

The compounds of this invention may be used in pharmaceutical compositions comprising (a) the compound(s) or pharmaceutically acceptable salts thereof, and (b) a pharmaceutically acceptable carrier. The compounds of this invention may be used in pharmaceutical compositions that include one or more other active pharmaceutical ingredients. The compounds of this invention may also be used in pharmaceutical compositions in which the compound of Formula I or a pharmaceutically acceptable salt thereof is the only active ingredient.

A compound of Formula I, or a pharmaceutically acceptable salt thereof, may be used in the manufacture of a medicament for the treatment of type 2 diabetes mellitus in a human or other mammalian patient.

A method of treating type 2 diabetes comprises the administration of a therapeutically effective amount of a compound of Formula I, or a pharmaceutically acceptable salt thereof, or a pharmaceutical composition comprising the compound, to a patient in need of treatment. Other medical uses of the compounds of Formula I are described hereinafter.

Definitions

"Ac" is acetyl, which is $CH_3C$(=O)—.

"Alkyl" means saturated carbon chains which may be linear or branched or combinations thereof, unless the carbon chain is defined otherwise. Other groups having the prefix "alk", such as alkoxy and alkanoyl, also may be linear or branched, or combinations thereof, unless the carbon chain is defined otherwise. Examples of alkyl groups include methyl, ethyl, propyl, isopropyl, butyl, sec-and tert-butyl, pentyl, hexyl, heptyl, octyl, nonyl, and the like.

"Alkenyl" means carbon chains which contain at least one carbon-carbon double bond, and which may be linear or branched, or combinations thereof, unless otherwise defined. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched, or combinations thereof, unless otherwise defined.

Examples of alkynyl include ethynyl, propargyl, 3-methyl-1-pentynyl, 2-heptynyl and the like.

"Cycloalkyl" means a saturated carbocyclic ring, having a specified number of carbon atoms. The term may also be used to describe a carbocyclic ring fused to an aryl group. Examples of cycloalkyl include cyclopropyl, cyclopentyl, cyclohexyl, cycloheptyl, and the like. Cycloalkenyl rings comprise a double bond in the ring.

"Aryl" is commonly used to refer to carbocyclic aromatic structures. The most common aryl groups are phenyl and naphthyl. Phenyl is generally the most preferred aryl group.

"Heterocycle" means a saturated or partly unsaturated ring or ring system containing at least one heteroatom selected from N, S and O, wherein the number of heteroatoms and the ring size and the degree of unsaturation (if any) are defined herein. Examples of heterocycles include tetrahydrofuran, piperazine, piperidine, morpholine, oxetane (4-membered cyclic ether), and tetrahydropyran (6-membered cyclic ether).

"Heteroaryl" means a heteroaromatic ring containing at least one ring heteroatom selected from N, O and S (including SO and $So_2$), as defined more specifically herein. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzisoxazolyl, benzoxazolyl, benzothiazolyl, benzimidazolyl, benzofuranyl, benzothiophenyl (including S-oxide and dioxide), furo(2,3-b)pyridyl, quinolyl, indolyl, isoquinolyl, quinazolinyl, dibenzofuranyl, and the like.

"Halogen" includes fluorine, chlorine, bromine and iodine.

"Me" represents methyl.

The phrase "pharmaceutically acceptable" is employed herein to refer to those compounds, materials, compositions, salts and/or dosage forms which are, using sound medical judgment, and following all applicable government regulations, safe and suitable for administration to a human being or an animal.

The term "composition," as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

The substituent "tetrazole" means a 2H-tetrazol-5-yl substituent group and tautomers thereof.

Optical Isomers—Diastereomers—Geometric Isomers—Tautomers

Compounds of Formula I may contain one or more asymmetric centers and can thus occur as racemates, racemic mixtures, single enantiomers, individual diastereomers, and mixtures of diastereomers and/or enantiomers. The invention is meant to comprehend all such isomeric forms of the compounds of Formula I. Specifically, the compounds of the instant invention have at least three asymmetric centers. Additional asymmetric centers may be present depending upon the nature of the various substituents on the molecule. It is intended that all of the possible optical isomers, stereoisomers, and diastereomers in mixtures and as pure or partially purified compounds are included within the scope of this invention (i.e. all possible combinations of the asymmetric centers as pure compounds or in mixtures).

Some of the compounds described herein may contain olefinic double bonds, and unless specified otherwise, are meant to include both E and Z geometric isomers.

Some of the compounds described herein may exist with different points of attachment of hydrogen, referred to as tautomers. An example is a ketone and its enol form, known as keto-enol tautomers. The individual tautomers as well as mixtures thereof are encompassed with compounds of Formula I.

Compounds of Formula I having one or more asymmetric centers may be separated into diastereoisomers, enantiomers, and the like by methods well known in the art.

Alternatively, enantiomers and other compounds with chiral centers may be synthesized by stereospecific synthesis using optically pure starting materials and/or reagents of known configuration.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, or when it has a basic substituent group in its structure, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, as used herein, references to the compounds of Formula I are meant to also include the pharmaceutically acceptable salts.

Metabolites—Prodrugs

The invention includes therapeutically active metabolites, where the metabolites themselves fall within the scope of the claims. The invention also includes prodrugs, which are compounds that are converted to the claimed compounds as they are being administered to a patient or after they have been administered to a patient. The claimed chemical structures of this application in some cases may themselves be prodrugs.

Utilities

The compounds described herein are potent agonists of the GPR40 receptor. The compounds, and pharmaceutically acceptable salts thereof, may be efficacious in the treatment of diseases that are modulated by GPR40 ligands, which are generally agonists. Many of these diseases are summarized below.

One or more of the following diseases may be treated by the administration of a therapeutically effective amount of a compound of Formula I, or a pharmaceutically acceptable salt thereof, to a patient in need of treatment. Also, the compounds of Formula I may be used for the manufacture of a medicament for treating one or more of these diseases:

(1) non-insulin dependent diabetes mellitus (type 2 diabetes);
(2) hyperglycemia;
(3) the metabolic syndrome;
(4) obesity;
(5) hypercholesterolemia;
(6) hypertriglyceridemia (elevated levels of triglyceride-rich-lipoproteins);
(7) mixed or diabetic dyslipidemia;
(8) low HDL cholesterol;
(9) high LDL cholesterol;
(10) hyperapoBliproteinemia; and
(11) atherosclerosis.

Preferred uses of the compounds are for the treatment of one or more of the following diseases by administering a therapeutically effective amount to a patient in need of treatment. The compounds may be used for manufacturing a medicament for the treatment of one or more of these diseases:

(1) Type 2 diabetes, and specifically hyperglycemia associated with type 2 diabetes;
(2) Metabolic syndrome;
(3) Obesity; and
(4) Hypercholesterolemia.

The compounds are expected to be effective in lowering glucose and lipids in diabetic patients and in non-diabetic patients who have impaired glucose tolerance and/or are in a pre-diabetic condition. The compounds may ameliorate hyperinsulinemia, which often occurs in diabetic or pre-diabetic patients, by modulating the swings in the level of serum glucose that often occurs in these patients. The compounds may also be effective in treating or reducing insulin resistance. The compounds may be effective in treating or preventing gestational diabetes.

The compounds, compositions, and medicaments as described herein may also be effective in reducing the risks of adverse sequelae associated with metabolic syndrome, and in reducing the risk of developing atherosclerosis, delaying the onset of atherosclerosis, and/or reducing the risk of sequelae of atherosclerosis. Sequelae of atherosclerosis include angina, claudication, heart attack, stroke, and others.

By keeping hyperglycemia under control, the compounds may also be effective in delaying or preventing vascular restenosis and diabetic retinopathy.

Impairments in insulin and insulin-like growth factor in the brain are associated with dementia and Alzheimer's disease. See de la Monte et al., *J. Alzheimer's Disease*, 10(1): 89-109, September, 2006. The compounds disclosed herein may have utility in treating, preventing, or slowing the progression of Alzheimer's disease.

The compounds of this invention may also have utility in improving or restoring β-cell function, so that they may be useful in treating type 1 diabetes or in delaying or preventing a patient with type 2 diabetes from needing insulin therapy.

The compounds generally may be efficacious in treating one or more of the following diseases: (1) type 2 diabetes (also known as non-insulin dependent diabetes mellitus, or NIDDM), (2) hyperglycemia, (3) impaired glucose tolerance, (4) insulin resistance, (5) obesity, (6) lipid disorders, (7) dyslipidemia, (8) hyperlipidemia, (9) hypertriglyceridemia, (10) hypercholesterolemia, (11) low HDL levels, (12) high LDL levels, (13) atherosclerosis and its sequelae, (14) vascular restenosis, (15) abdominal obesity, (16) retinopathy, (17) metabolic syndrome, (18) high blood pressure, and (19) insulin resistance.

One aspect of the invention provides a method for the treatment and control of mixed or diabetic dyslipidemia, hypercholesterolemia, atherosclerosis, low HDL levels, high LDL levels, hyperlipidemia, and/or hypertriglyceridemia, which comprises administering to a patient in need of such treatment a therapeutically effective amount of a compound having formula I. The compound may be used alone or advantageously may be administered with a cholesterol biosynthesis inhibitor, particularly an HMG-CoA reductase inhibitor such as lovastatin, simvastatin, rosuvastatin, pravastatin, fluvastatin, atorvastatin, rivastatin, or itavastatin. The compound may also be used advantageously in combination with other lipid lowering drugs such as cholesterol absorption inhibitors (for example stanol esters, sterol glycosides such as tiqueside, and azetidinones such as ezetimibe), ACAT inhibitors (such as avasimibe), CETP inhibitors (for example torcetrapib and those described in published applications WO2005/100298, WO2006/014413, and WO2006/014357), niacin and niacin receptor agonists, bile acid sequestrants, microsomal triglyceride transport inhibitors, and bile acid reuptake inhibitors. These combination treatments may be effective for the treatment or control of one or more related conditions selected from the group consisting of hypercholesterolemia, atherosclerosis, hyperlipidemia, hypertriglyceridemia, dyslipidemia, high LDL, and low HDL.

Administration and Dose Ranges

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of Formula I are administered orally.

The effective dosage of active ingredient employed may vary depending on the particular compound employed, the mode of administration, the condition being treated and the severity of the condition being treated. Such dosage may be ascertained readily by a person skilled in the art.

When treating or controlling diabetes mellitus and/or hyperglycemia or hypertriglyceridemia or other diseases for which compounds of Formula I are indicated, generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams. In the case of a 70 kg adult human, the total daily dose will generally be from about 1 milligram to about 500 milligrams. For a particularly potent compound, the dosage for an adult human may be as low as 0.1 mg. In some cases, the daily dose may be as high as one gm. The dosage regimen may be adjusted within this range or even outside of this range to provide the optimal therapeutic response.

Oral administration will usually be carried out using tablets or capsules. Examples of doses in tablets and capsules are 0.1 mg, 0.25 mg, 0.5 mg, 1 mg, 2 mg, 5 mg, 10 mg, 25 mg, 50 mg, 100 mg, 200 mg, 300 mg, 400 mg, 500 mg, and 750 mg. Other oral forms may also have the same or similar dosages.

Pharmaceutical Compositions

Another aspect of the present invention provides pharmaceutical compositions which comprise a compound of Formula I and a pharmaceutically acceptable carrier. The pharmaceutical compositions of the present invention comprise a compound of Formula I or a pharmaceutically acceptable salt as an active ingredient, as well as a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids. A pharmaceutical composition may also comprise a prodrug, or a pharmaceutically acceptable salt thereof, if a prodrug is administered.

The compositions include compositions suitable for oral, rectal, topical, parenteral (including subcutaneous, intramuscular, and intravenous), ocular (ophthalmic), pulmonary (nasal or buccal inhalation), or nasal administration (e.g. liquid drops or spray), although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions as oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are employed. If desired, tablets may be coated by standard aqueous or non-aqueous techniques. Such compositions and preparations should contain at least 0.1 percent of active compound. The percentage of active compound in these compositions may be varied and may conveniently be between about 2 percent to about 60 percent of the weight of the unit. The amount of active compound in such therapeutically useful compositions is such that an effective dosage will be obtained.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

In some instances, depending on the solubility of the compound or salt being administered, it may be advantageous to formulate the compound or salt as a solution in an oil such as a triglyceride of one or more medium chain fatty acids, a lipophilic solvent such as triacetin, a hydrophilic solvent (e.g. propylene glycol), or a mixture of two or more of these, also optionally including one or more ionic or nonionic surfactants, such as sodium lauryl sulfate, polysorbate 80, polyethoxylated triglycerides, and mono and/or diglycerides of one or more medium chain fatty acids. Solutions containing surfactants (especially 2 or more surfactants) will form emulsions or microemulsions on contact with water. The compound may also be formulated in a water soluble polymer in which it has been dispersed as an amorphous phase by such methods as hot melt extrusion and spray drying, such polymers including hydroxypropylmethylcellulose acetate succinate (HPMCAS), hydroxypropylmethyl cellulose (HPMC), and polyvinylpyrrolidinones, including the homopolymer and copolymers.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula I may also be administered parenterally. Solutions or suspensions of these active compounds can be prepared in water suitably mixed with a surfactant or mixture of surfactants such as hydroxypropylcellulose, polysorbate 80, and mono and diglycerides of medium and long chain fatty acids. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Combination Therapy

Compounds of Formula I may be used in combination with other drugs that may also be useful in the treatment or amelioration of the diseases or conditions for which compounds of Formula I are useful. Such other drugs may be administered, by a route and in an amount commonly used therefor, contemporaneously or sequentially with a compound of Formula I. In the treatment of patients who have type 2 diabetes, insulin resistance, obesity, metabolic syndrome, and co-morbidities that accompany these diseases, more than one drug is commonly administered. The compounds of this invention may generally be administered to a patient who is already taking one or more other drugs for these conditions. Often the compounds will be administered to a patient who is already being treated with one or more antidiabetic compound, such as metformin, sulfonylureas, and/or PPAR agonists, when the patient's glycemic levels are not adequately responding to treatment.

When a compound of Formula I is used contemporaneously with one or more other drugs, a pharmaceutical composition in unit dosage form containing such other drugs and the compound of Formula I is preferred. However, the combination therapy also includes therapies in which the compound of Formula I and one or more other drugs are administered on different overlapping schedules. It is also contemplated that when used in combination with one or more other active ingredients, the compound of the present invention and the other active ingredients may be used in lower doses than when each is used singly. Accordingly, the pharmaceutical compositions of the present invention include those that contain one or more other active ingredients, in addition to a compound of Formula I.

Examples of other active ingredients that may be administered in combination with a compound of Formula I, and either administered separately or in the same pharmaceutical composition, include, but are not limited to:

(a) PPAR gamma agonists and partial agonists, including both glitazones and non-glitazones (e.g. pioglitazone, MCC-555, rosiglitazone, netoglitazone, T-131, and compounds disclosed in WO02/08188, WO2004/020408, WO2004/020409, and WO 2006/096514;

(b) biguanides such as metformin and phenformin;

(c) protein tyrosine phosphatase-1B (PTP-1B) inhibitors;

(d) dipeptidyl peptidase IV (DP-IV) inhibitors, such as sitagliptin, saxagliptin, and vildagliptin;

(e) insulin or insulin mimetics;

(f) sulfonylureas such as tolbutamide, glimepiride, glipizide, and related materials;

(g) α-glucosidase inhibitors (such as acarbose);

(h) agents which improve a patient's lipid profile, such as (i) HMG-CoA reductase inhibitors (lovastatin, simvastatin, rosuvastatin, pravastatin, fluvastatin, atorvastatin, rivastatin, itavastatin, and other statins), (ii) bile acid sequestrants (cholestyramine, colestipol, and dialkylaminoalkyl derivatives of a cross-linked dextran), (iii) niacin receptor agonists, nicotinyl alcohol, nicotinic acid, or a salt thereof, (iv) PPARα agonists such as fenofibric acid derivatives (gemfibrozil, clofibrate, fenofibrate and bezafibrate), (v) cholesterol absorption inhibitors, such as for example ezetimibe, (vi) acyl CoA:cholesterol acyltransferase (ACAT) inhibitors, such as avasimibe, (vii) CETP inhibitors, such as the compounds disclosed in WO2006/014357, WO2005/100298, and WO2006/014413, and (viii) phenolic anti-oxidants, such as probucol;

(i) PPARα/γ dual agonists, (j) PPARδ agonists such as GW501516;

(k) antiobesity compounds such as fenfluramine, dexfenfluramine, phentiramine, subitramine, orlistat, neuropeptide Y5 inhibitors, Mc4r agonists, cannabinoid receptor 1 (CB-1) antagonists/inverse agonists, and $\beta_3$ adrenergic receptor agonists;

(l) ileal bile acid transporter inhibitors;

(m) agents intended for use in inflammatory conditions such as aspirin, non-steroidal anti-inflammatory drugs, glucocorticoids, azulfidine, and cyclo-oxygenase 2 selective inhibitors;

(n) glucagon receptor antagonists;

(o) GLP-1;

(p) GIP-1;

(q) GLP-1 analogs, such as exendins, for example exenatide (Byetta); and (r) Hydroxysterol dehydrogenase-1 (HSD-1) inhibitors.

The above combinations include combinations of a compound of the present invention not only with one other active compound, but also with two or more other active compounds. Non-limiting examples include combinations of compounds having Formula I with two or more active compounds selected from biguanides, sulfonylureas, HMG-CoA reductase inhibitors, other PPAR agonists, PTP-1B inhibitors, DP-IV inhibitors, and anti-obesity compounds.

Biological Assays

Generation of GPR40-Expressing Cells

Human and mouse GPR40 stable cell-lines were generated in CHO cells stably expressing NFAT BLA (Beta-lactamase). A human GPR40 stable cell-line was generated in HEK cells stably expressing the aequorin expressing reporter. The expression plasmids were transfected using lipofectamine (Life Technologies) following manufacturer's instructions. Stable cell-lines were generated following drug selection.

FLIPR Assays

FLIPR (Fluorimetric Imaging Plate Reader, Molecular Devices) assays were performed to measure agonist-induced calcium mobilization of the stable clones. For the FLIPR assay, one day before assay, GPR40/CHO NFAT BLA cells were seeded into black-wall-clear-bottom 384-well plates (Costar) at 1.4×10e4 cells/20 µl medium/well. The cells were incubated with 20 µl/well of the assay buffer (HBSS, 0.1% BSA, 20 mM HEPES, 2.5 mM probenecid, pH 7.4) containing 8 µM fluo-4,AM, 0.08% pluronic acid at room temperature for 100 minutes. Fluorescence output was measured using FLIPR. Compounds were dissolved in DMSO and diluted to desired concentrations with assay buffer. 13.3 µl/well of compound solution was added.

Inositol Phosphate Turnover Assay

The assay is performed in 96-well format. HEK cells stably expressing human GPR40 are plated to be 60-80% confluent within 72 hours. After 72 hours, the plates are aspirated and the cells washed with inositol-free DMEM (ICN). The wash media is replaced with 150 uL of 3H-inositol labeling media (inositol-free media containing 0.4% human albumin or 0.4% mouse albumin, 1X pen/strep antibiotics, glutamine, 25 mM HEPES to which is added 3H-myo-inositol NEN #NET114A 1 mCi/mL, 25 Ci/mmol diluted 1:150 in loading media with a final specific radioactivity of 1 uCi/150 uL). Alternatively, the human and mouse albumin can be added after the overnight labeling step before the addition of LiCl.

The assay is typically run the next day after 18 hours labeling. On the day of the assay, 5 uL of 300 mM LiCl is added to all wells and incubated at 37 degrees for 20 mins. 0.75 uL of 200X compounds are added and incubated with the cells for 60 minutes at 37 degrees. The media is then aspirated off and the assay terminated with the addition of 60 uL 10 mM formic acid. The cells are lysed for 60 mins at room temperature. 15-30 uL of lysate is mixed with 70 uL/1 mg YSi SPA beads (Amersham) in clear bottom Isoplates. The plates are shaken for 2 hours at room temperature. Beads are allowed to settle and the plates are counted in the Wallac Microbeta.

In Vivo Studies

Male C57BL/6N mice (7-12 weeks of age) are housed 10 per cage and given access to normal diet rodent chow and water ad libitum. Mice are randomly assigned to treatment groups and fasted 4 to 6 hours. Baseline blood glucose concentrations are determined by glucometer from tail nick blood. Animals are then treated orally with vehicle (0.25% methylcellulose) or test compound. Blood glucose concentration is measured at a set time point after treatment (t=0 min) and mice are then intraperitoneally-challenged with dextrose (2 g/kg). One group of vehicle-treated mice is challenged with saline as a negative control. Blood glucose levels are determined from tail bleeds taken at 20, 40, 60 minutes after dextrose challenge. The blood glucose excursion profile from t=0 to t=60 min is used to integrate an area under the curve (AUC) for each treatment. Percent inhibition values for each treatment are generated from the AUC data normalized to the saline-challenged controls.

EXAMPLES

The following Examples are provided to illustrate the invention and are not to be construed as limiting the invention in any manner. The scope of the invention is defined by the appended claims.

The compounds in these examples all have IC50 values in the range of 1 nM to 4 μM using the binding assay described above. Preferred compounds have IC50 values in the range of 1 nM to 100 nM.

Several methods for preparing the compounds of this invention are illustrated in the following Schemes and Examples. Starting materials are either commercially available or made by known procedures in the literature or as illustrated. The present invention further provides processes for the preparation of compounds of formula I as defined above. In some cases the order of carrying out the foregoing reaction schemes may be varied to facilitate the reaction or to avoid unwanted reaction products. The following examples are provided for the purpose of illustration only and are not to be construed as limitations on the disclosed invention.

General Procedures for Tricyclic Acid GPR40 Agoinsts

Scheme 1: Biaryl Ethers

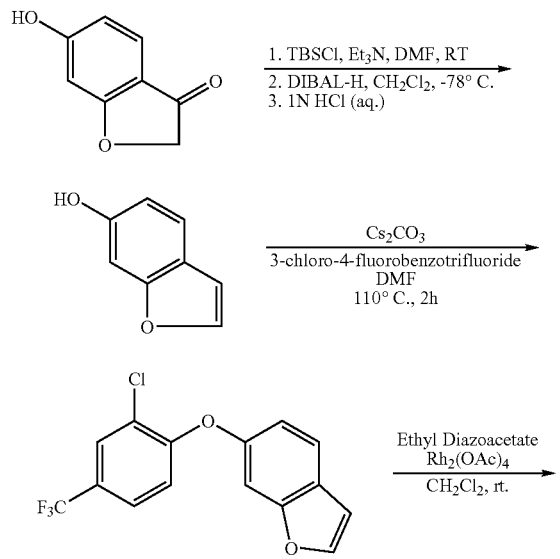

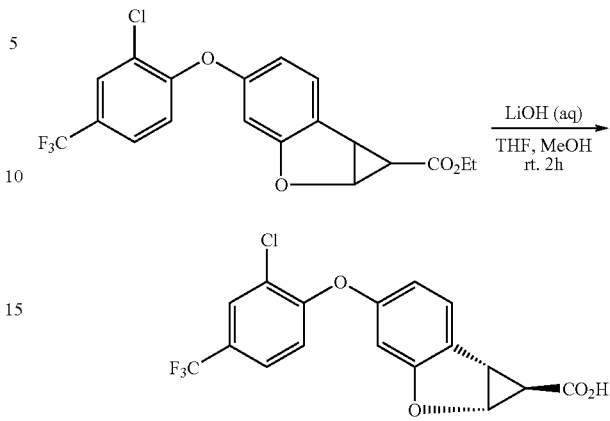

Synthesis of 1-Benzofuran-6-ol Intermediate

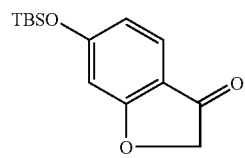

Step 1

6-tert-Butyldimethylsilyloxy-1-benzofuran-3(2H)-one

To a stirred solution of 6-hydroxy-2,3-dihydrobenzofuran-3-one (30 g, 0.2 mol) in DMF (375 mL) was added tert-butyldimethylsilyl chlroride (39.2 g, 0.26 mol) and triethylamine (42 mL, 0.3 mol). The mixture was stirred at room temperature for 2 h. It was then diluted with diethyl ether (1.5 L), washed with ammonium chloride (750 mL, aq. sat.) and brine (450 mL), dired over magnesium sulfate, filtered and concentrated. The crude product was purified on a Biotage 65i silica gel column, eluting with ethyl acetate and hexanes (3:7). The final product was collected as yellow solid.

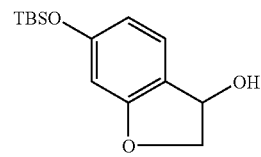

Step 2

6-tert-Butyldimethylsilyloxy-2,3-dihydro-1-benzofuran-3-ol.

To a stirred solution of 6-tert-Butyldimethylsilyloxy-2,3-dihydrobenzofuran-3-one (42 g, 158 mmol) in dichloromethane (1.4 L) at −78° C. under nitrogen was slowly added a solution of DIBAL-H (238 mL, 1.0 M, 238 mmol) in dichloromethane. The reaction was stirred at −78° C. for 1 h, and then was quenched carefully with ethyl acetate (1.0 L). Cold bath was removed, and a solution of Rochelle's salt (400 mL, 10%) was added continuously with stirring over a period of 2 h. The mixture was then diluted with MTBE (4.0 L), washed with brine, dried with magnesium sulfate, filtered and concentrated to yield the final product as yellow oil.

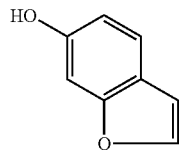

Step 3

1-Benzofuran-6-ol

To a stirred solution of 6-hydroxy-2,3-dihydrobenzofuran-3-ol (35.2 g, 0.2 mol) in THF (1.3 L) was added hydrochloric acid (323 mL, 1.0 N). The mixture was stirred at 65° C. for 2 h. After cooling to room temperature, it was diluted with brine (2.0 L), extracted with ethyl acetate (4.0 L), dried over magnesium sulfate, filtered and concentrated. The crude product was purified on a silica gel column, eluting with ethyl acetate (1-30%) in heptane. The final product was collected as light brown solid.

Alternate Synthesis of 1-Benzofuran-6-ol

1-Benzofuran-6-ol is also made using the following 3-step procedure using commercially available materials or materials easily obtained by known methods.

Step 1

2-chloro-1-(2,4-dihydroxyphenyl)ethanone 2

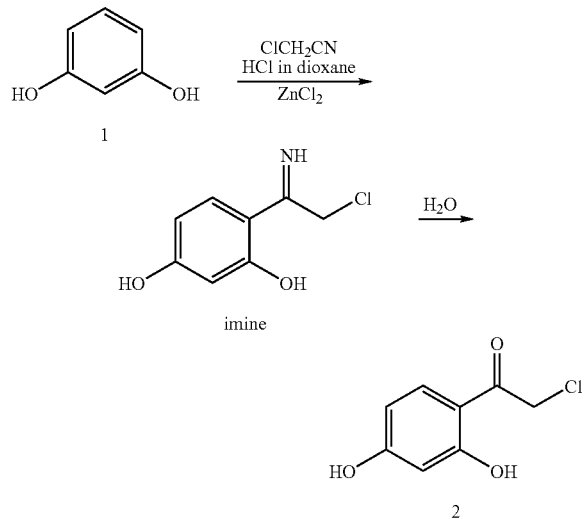

A 100L round bottomed flask (RBF) containing 34.0 L of 1,4-dioxane was charged with 5.0 kg of HCl gas through a subsurface line. Resorcinol (10.0 kg) was then added as a solid, followed by addition of solid $ZnCl_2$ (6.20 kg). A slight exotherm from 21 to 29° C. occurred after the $ZnCl_2$ addition. The mixture was cooled with an ice/water bath, and chloroacetonitrile (7.50 kg) was added in portions over 2 h while maintaining the temperature at <40° C. The reaction mixture was aged 9 h at room temperature, and then water (34 L) was charged over 0.5 h. An exotherm to 40° C. occurred at the beginning of the water addition, and the reaction eventually cooled to 27° C. by the end of the addition. The resulting slurry was aged for 11 h at room temperature. More water (14L) was added, and the slurry was cooled to 0° C. The slurry was filtered, washed with water (4×20L), and then dried under a fast flow of nitrogen. After 5 days of drying, the chloroketone 2 was isolated as a light pink solid.

Step 2

Cyclization of 2 to 6-hydroxy-1-benzofuran-3(2H)-one 3

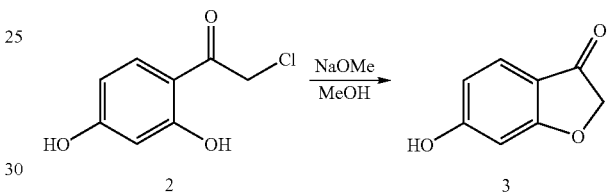

Solid NaOMe (6134 g) was added to a 0° C. solution of the chloroketone 2 (7062 g) in 49 L of methanol (MeOH) in portions over 2 h while maintaining the temperature at <20° C. The slurry was aged at room temperature for 1 h, at which time cyclization was determined to be complete by HPLC. The mixture was cooled to 0° C., and 2N HCl (49 L) was added while maintaining the temperature at <20° C. The slurry was cooled to 5-10° C., filtered, and washed first with cold 1:1 MeOH/water (5 L), and then with water (16 L). The wet filter cake was slurry washed with isopropyl alcohol (IPA) (18 L), and then was finally washed with heptane. The filter cake was then dried under a fast stream of nitrogen. Ketone 3 was isolated as a white solid.

Step 3

Ketone Reduction/Elimination to 1-Benzofuran-6-ol 4

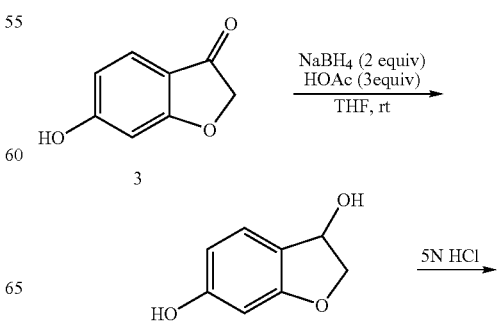

-continued

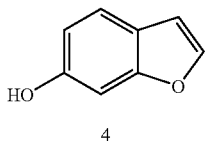

4

Acetic acid (HOAc) (3.11 L, 3 equivalents) was added to a slurry of NaBH$_4$ (1368 g) in 41.0 L of tetrahydrofuran (THF) at 23° C. over 6 h. Vigorous gas evolution occurred, and an ice/water bath was used to maintain the temperature at <30° C. The mixture was maintained for at least 8 h at ambient temperature. Ketone 3 (2715 g, 1 equivalent) was added as a solid in portions over 1 h to minimize gas evolution, and an ice/water bath was used to keep the temperature at <30° C. The resulting mixture was aged at room temperature for 6 h. Water (6 L) was added over 2 h with cooling so that the temperature was maintained at <30° C. Vigorous gas evolution occurred, especially early in the water addition. The slurry became thick during the water addition. To the slurry was added 5N HCl (5 L) over 1 h, and the mixture was aged for 0.5 h. Elimination was assayed as complete by HPLC. The reaction mixture was transferred to a 100 L extraction vessel, and 26 L of methyl t-butyl ether (MTBE) and 17 L of water were added. Then 10 N NaOH (5 L) was added, and the mixture was mixed vigorously. The dark aqueous layer (pH ~9) was separated. The organic layer was washed with 10 wt. % Na$_2$CO$_3$ (5 L). The pH of the aqueous wash was ~10. The organic layer was then washed with 20% brine (5 L). The organic layer was concentrated on a rotary evaporator, and was then rinsed from the flask with toluene (6 L). Toluene (4 L) was then added, and the resulting thin slurry was filtered to remove impurities. The filtrate was concentrated on a rotary evaporator to an oil that eventually solidified to 1-benzofuran-6-ol 4 as a pale orange solid.

Example 1

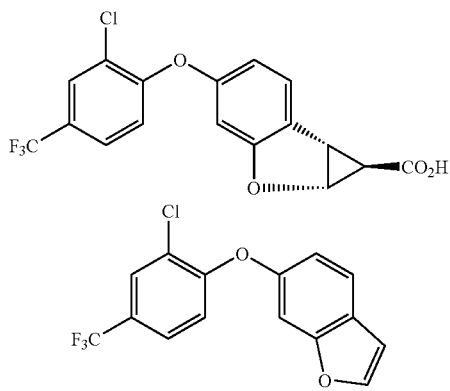

Step 1

6-[2-Chloro-4-(trifluoromethyl)phenoxy]-1-benzofuran

To a stirred solution of 1-benzofuran-6-ol (418.5 mg, 3.1 mmol) in 6 ml of DMF was added 3-Chloro-4-fluorobenzotrifluoride (681.4 mg, 3.4 mmol) and cesium carbonate (1.5 g, 4.7 mmol). The reaction mixture was heated at 80° C. for 2 hours. After cooling to room temperature, it was diluted with ethyl acetate, washed with water (2×) and brine, dried over magnesium sulfate, filtered and concentrated. The crude product was purified on a silica gel column, eluting with ethyl acetate (0-30%) in hexane. The final product was collected as colorless oil. $^1$H NMR (CDCl$_3$, δ ppm): 6.8 (s, 1H), 7.0 (two d, 2H), 7.2 (s, 1H), 7.4 (d, 1H), 7.6 (d, 1H), 7.7 (s, 1H), 7.8 (s, 1H).

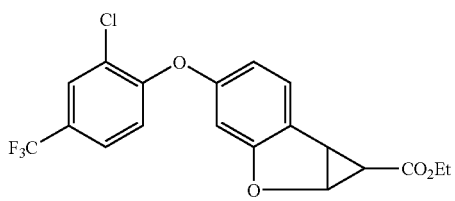

Step 2

Ethyl 4-[2-chloro-4-(trifluoromethyl)phenoxy]-1a,6b-dihydro-1H-cyclopropa[b][1]benzofuran-1-exo-carboxylate To a stirred solution of the above phenoxybenzofuran (250 mg, 0.80 mmol) in dichloromethane (4.5 ml) was added rhodium acetate dimer (42 mg, 0.1 mmol), followed by a slow addition of a solution ethyl diazoacetate (0.50 mL, 4.8 mmol) in dichloromethane (4.5 ml) through syringe pump over a period of 5.5 h. After the addition, the reaction mixture was stirred at room temperature overnight. Precipitates were filtered off and solvent was evaporated. The residue was purified by preparative TLC on silica gel plates to give the trans (or exo-) diastereomer, along with the cis (or endo-) diastereomer, as a minor product. $^1$H NMR (CDCl$_3$, δ ppm) of trans (exo) diastereomer: 1.3 (t, 3H), 1.4 (m, 1H), 3.3 (m, 1H), 4.2 (q, 2H), 5.2 (m, 1H), 6.6 (m, 2H), 7.0 (d, 1H), 7.4 (d, 1H), 7.5 (d, 1H), 7.8 (s, 1H). $^1$H NMR (CDCl$_3$, δ ppm) of cis (or endo-) diastereomer,: 1.1 (t, 3H), 1.9 (m, 1H), 3.3 (m, 1H), 4.0 (q, 2H), 5.2 (m, 1H), 6.6 (m, 2H), 7.0 (d, 1H), 7.4 (d, 1H), 7.5 (d, 1H), 7.8 (s, 1H).

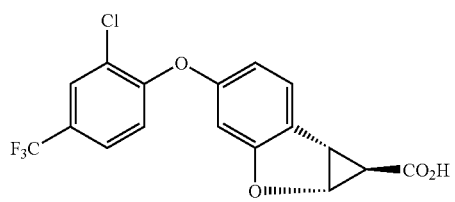

Step 3

(1R, 1aR, 6bS)-4-[2-Chloro-4-(trifluoromethyl)phenoxy]-1a,6b-dihydro-1H-cyclopropa[b][1]benzofuran-1-carboxylic acid To a stirred solution of the above trans ester (44 mg, 0.11 mmol) in THF-MeOH (1.6 ml-0.8 ml) was added LiOH (0.83 mL, 2N aq.). The reaction mixture was stirred at room temperature for 1.5h, and then was concentrated under reduced pressure. The residue was acidified with HCl (0.5N) and was extracted with ethyl acetate. The combined extracts were dried and concentrated to give a crude product, which was purified on ChiralPak AD-H semi-preparative column, eluting with 4-7% ethanol in heptane. The desired enantiomer shown above was isolated. $^1$H NMR (CDCl$_3$, δ ppm): 1.4 (m, 1H), 3.4 (m, 1H), 5.2 (m, 1H), 6.6 (m, 2H), 7.0 (d, 1H), 7.4 (d, 1H), 7.5 (d, 1H), 7.8 (s, 1H). The other enantiomer was also isolated: $^1$H NMR (CDCl$_3$, δ ppm): 1.9 (m, 1H), 3.4 (m, 1 H), 5.2 (m, 1H), 6.6 (m, 2H), 6.8 (d, 1H), 7.4 (d, 1H), 7.5 (d, 1H), 7.8 (s, 1H). MS: 369.1 (M−1).

Scheme 2: Copper Coupling

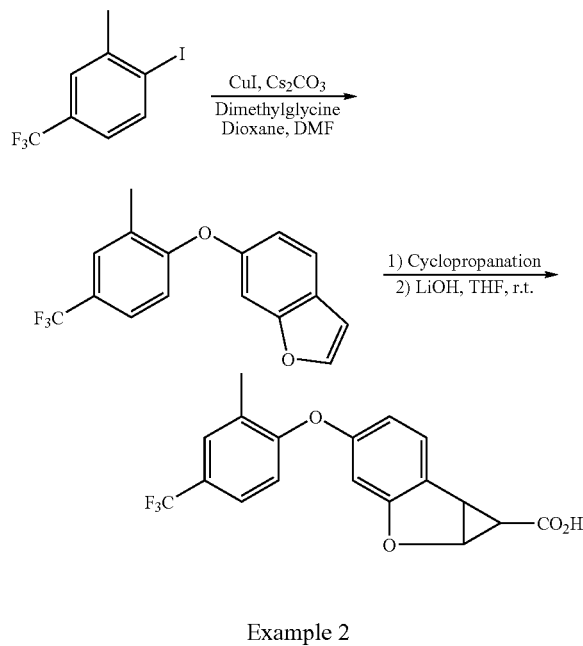

Example 2

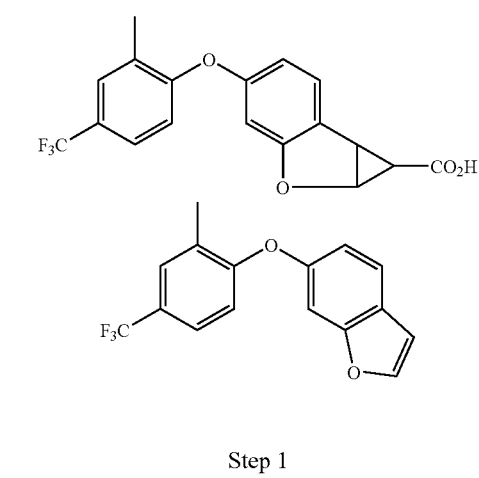

Step 1

[2-Methyl-4-(trifluoromethyl)phenoxy]-1-benzofuran

To a stirred solution of 1-benzofuran-6-ol (309 mg, 2.3 mmol) in dioxane (6 mL) and DMF (12 mL) was added 2-methyl-4-trifluoromethylphenyl iodide (600 mg, 2.3 mmol), copper iodide (108 mg, 0.57 mmol), dimethylglycine hydrochloride (243 mg, 1.7 mmol), and cesium carbonate (1.88 g, 5.8 mmol). The reaction was stirred at 110° C. for 22 h. After cooling to room temperature, solvents were removed in vacuo. The residue was dissolved in ethyl acetate, washed with water and brine, dried and concentrated. The crude product was purified on a silica gel column, eluting with ethyl acetate (0-10%) in hexanes. The final product was collected as a slightly yellow oil.

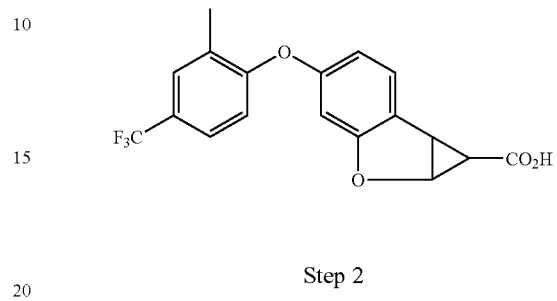

Step 2

4-[2-Methyl-4-(trifluoromethyl)phenoxy]-1a,6b-dihydro-1H-cyclopropa[b][1]benzofuran-1-exo-carboxylic acid Follows the method of Example 1, Steps 2 and 3. MS: 349.2 (M−1).

Scheme 3: Asymmetric Cyclopropanation

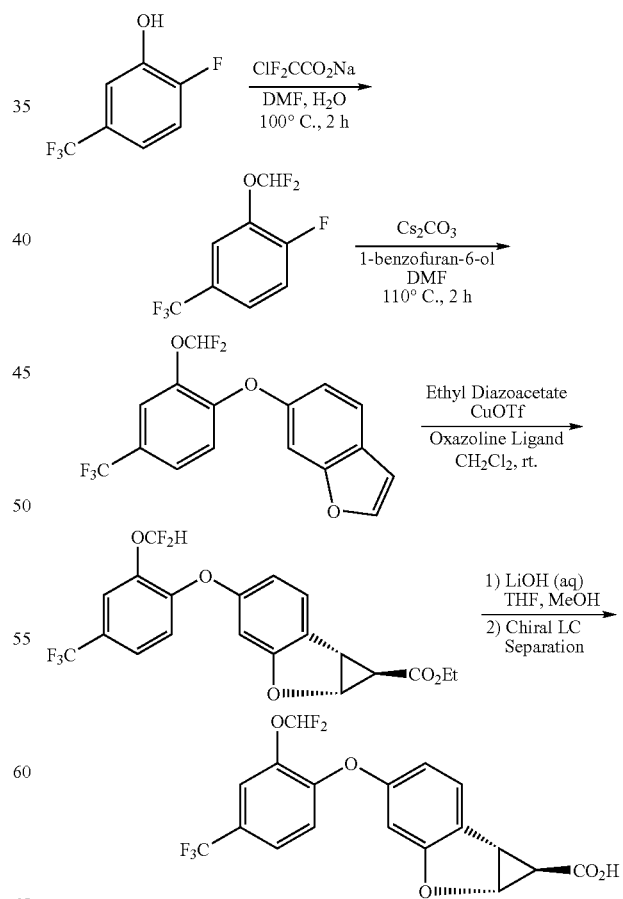

Example 3

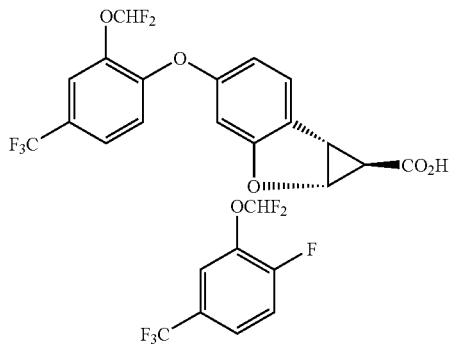

Step 1

2-(Difluoromethoxy)-1-fluoro-4-trifluoromethylbenzene

To a stirred solution of 2-fluoro-5-trifluoromethyl-1-phenol (9.9 g, 54.9 mmol) in 100 ml of DMF (100 mL) and water (10 mL) was added sodium chlorodifluoroacetate (20.9 g, 137.2 mmol) and cesium carbonate (26.8 g, 82.3 mmol). The reaction mixture was stirred at 100° C. for 2 hours. After it cooled to room temperature, it was diluted with ethyl acetate (700 ml), washed with water (3x) and brine, dried over magnesium sulfate, filtered and concentrated. The crude product (colorless oil, volatile) was used for the next step without further treatment. $^1$H NMR (CDCl$_3$, δ ppm): 6.6 (t, 1H), 7.3 (m, 1H), 7.6 (m, 2H).

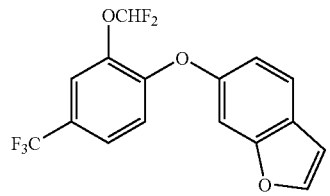

Step 2

6-[2-(Difluoromethoxy)-4-(trifluoromethyl)phenoxy]-1-benzofuran.

To a stirred solution of 1-benzofuran-6-ol (13.4 g, 100 mmol) and 2-(difluoromethoxy)-1-fluoro-4-trifluoromethylbenzene (29.9 g, 130 mmol) in DMF (300 mL) was added cesium carbonate (65.2 g, 200 mmol). The reaction mixture was stirred at 75° C. for 16 hours (or at 110° C. for 2 hours). After cooling to room temperature, it was diluted with ethyl acetate, washed with water (2x) and brine, dried over magnesium sulfate, filtered and concentrated. The crude product was purified on a silica gel column, eluting with ethyl acetate (0-20%) in hexanes. The final product was collected as a colorless oil. $^1$H NMR (CDCl$_3$, δ ppm): 6.7 (t, 1H, J=74 Hz), 6.8 (s, 1H), 7.0 (m, 2H), 7.2 (s, 1H), 7.4 (d, 1H), 7.6 (m, 3H).

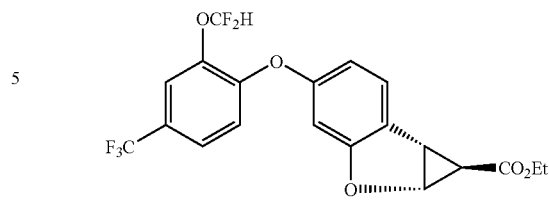

Step 3

Ethyl 4-[2-(difluoromethoxy)-4-(trifluoromethyl)phenoxy]-1a,6b-dihydro-1H-cyclopropa[b][1]benzofuran-1-exo-carboxylate A solution of Cu(1) triflate (toluene complex, Aldrich, 25 mg, 0.05 mol) and (R,R)-2,2'-isopropylidene-bis(4-tert-butyl-2-oxazoline) (DL Chiral, 35 mg, 0.12 mol) in dichloromethane (10 mL) was stirred at room temperature for 2 h. Ethyl diazoacetate (neat, 1 drop) was added, and the solution turned brown temporarily. A solution of the benzofuran from the previous step (1.0 g, 2.9 mmol) in dichloromethane (~5 mL) was added, followed by a slow addition of a solution of ethyl diazoacetate (1.25 mL, 14.3 mmol) in dichloromethane (5 mL) over a period of 8 h. The reaction was stirred at room temperature overnight after the completion of the addition. Precipitates were filtered off and solvent was evaporated. The residue was purified on a silica gel column, eluting with ethyl acetate (5-40%) in hexanes, to yield the desired trans (or exo-) diastereomer as a slightly yellow oil. $^1$H NMR (CDCl$_3$, δ ppm): 1.3 (t, 3H, J=7.1 Hz), 1.4 (m, 1H), 3.3 (m, 1H), 4.2 (q, 2H, J=7.1 Hz), 5.2 (m, 1H), 6.6 (t, 1H, J=74 Hz), 6.6 (m, 1H), 7.0 (d, 1H), 7.4 (d, 1H), 7.45 (d, 1H), 7.6 (s, 1H).

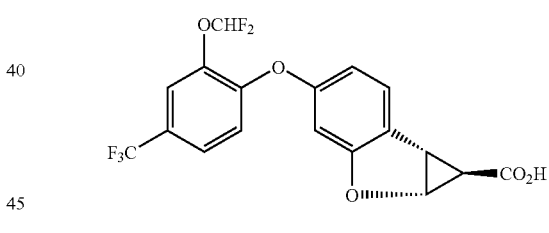

Step 4

(1R. 1aR. 6bS)-4-[2-(Difluoromethoxy)-4-(trifluoromethyl)phenoxy]-1a,6b-dihydro-1H-cyclopropa[b][1]benzofuran-1-carboxylic acid To a stirred solution of the above ester (0.7 g, 1.6 mmol) in THF (30 mL) and MeOH (10 mL) was added lithium hydroxide (16 mL, 1.0 N, 16 mmol). The reaction mixture was stirred at room temperature for 2 h, and then was concentrated under reduced pressure. The residue was acidified with HCl (2N aq) and extracted with EtOAc. The combined extracts were washed with brine, dried over magnesium sulfate, filtered and concentrated to yield the desired acid (70% ee) as a white crystalline solid. The final product was purified on ChiralPak AD-H semi-preparative column, eluting with 4-7% ethanol in heptane, yielding the desired enantiomer. The product is a crystalline anhydrate having the same crystal morphology as the product made by the process described after Example 29. $^1$H NMR (CDCl$_3$, δ ppm): 1.4 (m, 1H), 3.4 (m, 1H), 5.2 (m, 1H), 6.6 (t, 1H, J=74 Hz), 6.6 (d, 1H), 7.0 (d, 1H), 7.4 (d, 1H), 7.5 (d, 1H), 7.6 (s, 1H). MS: 401.1 (M−1).

Example 4

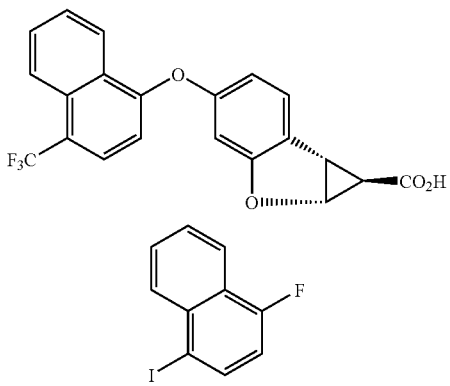

Step 1

A typical procedure is as follows: 1-bromo-4-fluoronaphthalene (1 eq.), CuI (25.0 mol %), racemic trans-N,N'-dimethylcyclohexane-1,2-diamine (50 mol %), and NaI (2.5 equivalents) were added to a sealed tube, degassed, and dioxane was then added. The reaction mixture was again degassed, flushed with nitrogen and heated at 110° C. for 24 hours. The reaction mixture was cooled to room temperature, diluted with ethyl acetate and the solid reagents were filtered off. The filtrate was concentrated to afford a residue which was purified by column chromatography (10% ethyl acetate/hexanes) to provide the desired product.

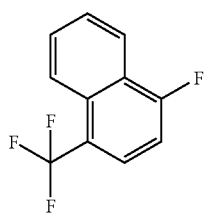

Step 2

In a typical experiment, 1-iodo-4-fluoronaphthalene (1 eq.), CuI (1.5-2.5 equiv), MFSDA (7-10 equiv), DIEA (7-10 equiv.) were added to a sealed tube, degassed, and DMF was then added. The reaction mixture was then degassed again and flushed with nitrogen and heated at 75° C. for 12 hours. The reaction mixture was then diluted with ethyl acetate and filtered. The filtrate was washed with water, and the aqueous phase was extracted with ethyl acetate (3×). The combined organic layer was washed with sodium bicarbonate and water, dried over sodium sulfate and concentrated to obtain the crude product which was purified by column chromatography (10% ethyl acetate/hexanes) to obtain the desired product.

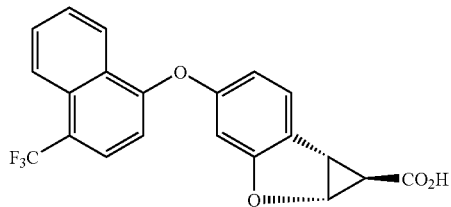

Step 3

4-{[4-(Trifluoromethyl)-1-naphthyl]oxy}-1a,6b-dihydro-1H-cyclopropa[b][1]benzofuran-1-exo-carboxylic acid Follows the method of Example 1. The final product was purified on a ChiralPak AD-H semi-preparative column, eluting with 4-7% ethanol in heptane. MS: 385.1 (M−1).

Example 5

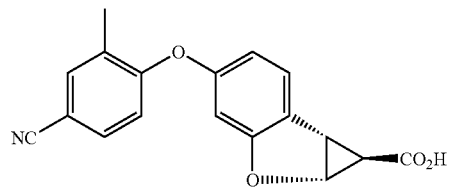

4-(4-Cyano-2-methylphenoxy)-1a,6b-dihydro-1H-cyclopropa[b][1]benzofuran-1-carboxylic acid Follows the method of Example 3. The final product was purified on ChiralPak AD-H semi-preparative column, eluting with 4-7% ethanol in heptane. MS: 308.3 (M+1).

Example 6

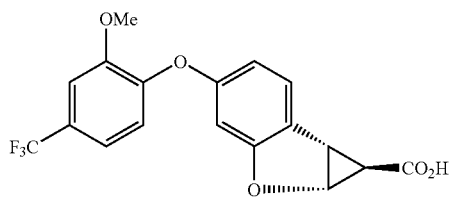

4-[2-Methoxy-4-(trifluoromethyl)phenoxy]-1a,6b-dihydro-1H-cyclopropa[b][1]benzofuran-1-exo-carboxylic acid Follows the method of Example 3. The final product was purified on ChiralPak AD-H semi-preparative column, eluting with 4-7% ethanol in heptane. MS: 365.1 (M−1).

Example 7

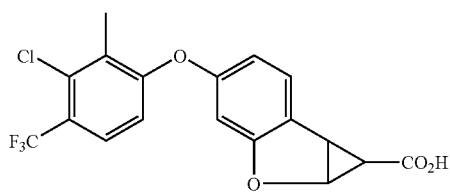

Step 1

2-Chloro-3-bromo-6-fluorotoluene (670 mg, 3 mmol), CuI (143 mg, 0.75 mmol), racemic trans-NN'-dimethylcyclohexane-1,2-diamine (213 mg, 1.5 mmol), and NaI (1.12 g, 7.5 mmol) were added to a sealed tube, degassed and dioxane (6 mL) was then added. The reaction mixture was again degassed, flushed with nitrogen and heated at 110° C. for 72 hours. The reaction mixture was cooled to room temperature, diluted with ethyl acetate and the solid reagents were filtered off. The filtrate was concentrated to afford a residue which was passed through a short silica gel column to provide the desired product.

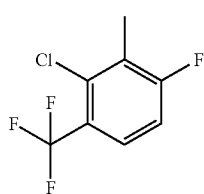

Step 2

The material obtained in Step 1 (600 mg, 2.2 mmol), CuI (628 mg, 3.3 mmol), MFSDA (2.96 g, 15.4 mmol), and DIEA (2.7 mL, 15.4 mmol) were added to a sealed tube, degassed, and DMF (2 mL) was then added. The reaction mixture was then degassed again and flushed with nitrogen and heated at 75° C. for 16 hours. The reaction mixture was then diluted with ethyl acetate and filtered. The filtrate was washed with water, and the aqueous phase was extracted with ethyl acetate (3×). The combined organic layer was washed with sodium bicarbonate and water, dried over MgSO$_4$ and concentrated to obtain the crude product which was used in the next step without further purification.

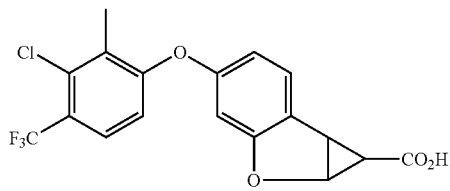

Step 3

4-[3-Chloro-2-methyl-4-(trifluoromethyl)phenoxy]-1a,6b-dihydro-1H-cyclopropa[b][r]benzofuran-1-exo-carboxylic acid Follows the method of Example 1, or Example 3. MS: 385.0 (M+1).

Example 8

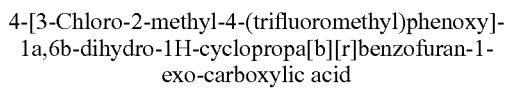

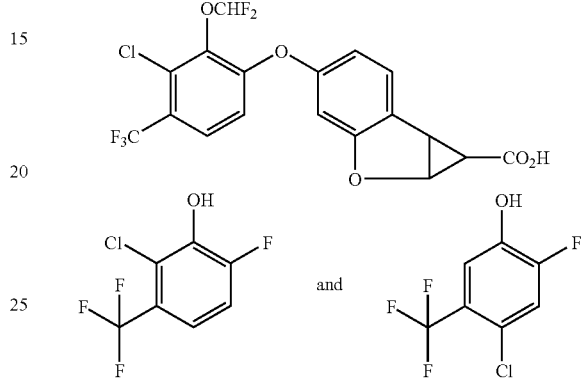

Step 1

To a solution of 2-fluoro-5-trifluoromethyl phenol (1080 mg, 6 mmol) in AcOH (12 mL) was added triflic acid (0.265 mL, 3 mmol) and NCS (881 mg, 6.6 mmol), and the mixture was heated to 60° C. for 20 hours. AcOH was removed and the residue was diluted with ethyl acetate, washed with water and brine, and concentrated. The crude products were then separated by reversed-phase HPLC with MeCN/0.5%TFA in water (20-70%) as the eluent to afford the desired products.

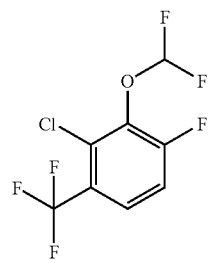

Step 2

Sodium chlorodifluoroacetate (178 mg, 1.17 mmol) and cesium carbonate (228 mg, 0.7 mmol) were added to a solution of 6-fluoro-2-chloro-3-trifluoromethylphenol in DMF containing 10 volume % water (1 mL), and the reaction mixture was heated for 1 h at 100° C. After cooling to room temperature, the reaction mixture was diluted with ethyl acetate and washed with water (3×), brine (1×). The organic layer was dried over MgSO$_4$ and concentrated to obtain the crude product which was used in the next step without further purification.

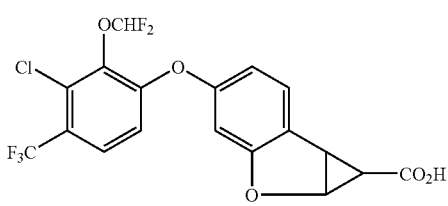

Step 3

4-[3-Chloro-2-(difluoromethoxy)-4-(trifluoromethyl)phenoxy]-1a,6b-dihydro-1H-cyclopropa[b][1]benzofuran-1-exo-carboxylic acid Follows the method of Example 1 or Example 3. MS: 437.0 (M+1).

Example 9

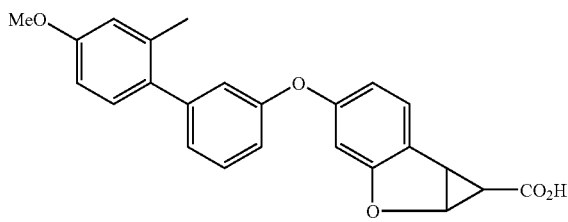

Step 1

To a solution of 3-iodo-phenylboronic acid (991 mg, 4 mmol) and 1-benzofuran-6-ol (269 mg, 2 mmol) in dichloromethane (8 mL) was added copper acetate (363 mg, 2 mmol), pyridine (0.8 mL, 10 mmol) and 4A molecular sieves (300 mg). The reaction mixture was degassed and stirred under an oxygen balloon overnight. It was then filtered and concentrated. The crude product was purified on a silica gel column, eluting with ethyl acetate (0-10%) in hexanes, to yield the desired product.

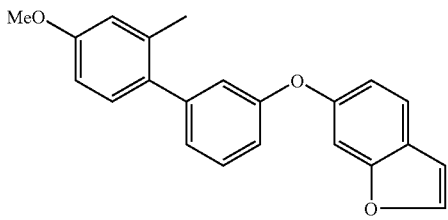

Step 2

6-[(4'-Methoxy-2'-methylbiphenyl-3-yl)oxy]-1-benzofuran

To a solution of the above phenyl iodide (318 mg, 0.95 mmol) and the corresponding boronic acid (188 mg, 1.13 mmol) in DMF (4 mL) was added PdCl$_2$dppf (77 mg, 0.9 mmol) and K$_3$PO$_4$ (502 mg, 2.36 mmol). The reaction mixture was heated at 100° C. for 20 hr. After cooling to room temperature and normal aqueous workup, the crude product was purified on a silica gel column, eluting with ethyl acetate (0-10%) in hexanes, to yield the desired product as colorless oil.

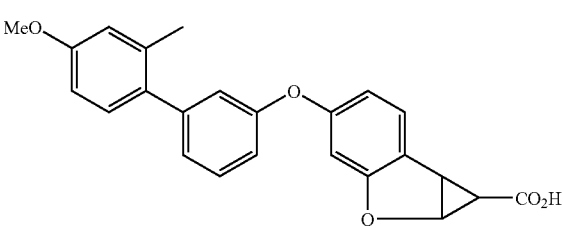

Step 3

4-[(4'-Methoxy-2'-methylbiphenyl-3-yl)oxy]-1a,6b-dihydro-1H-cyclopropa[b][1]benzofuran-1-exo-carboxylic acid See Example 1, or Example 3. MS: 387.3 (M−1).

Example 10

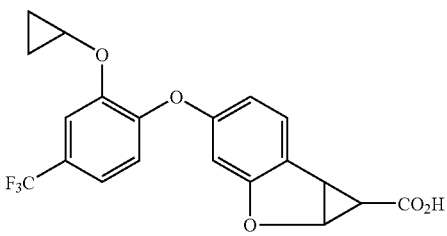

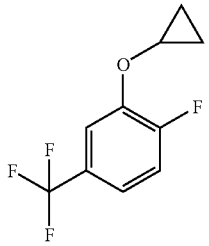

Step 1

To a solution of 2-fluoro-5-trifluoromethyl phenol in DMF (2 mL) was added cyclopropyl bromide (2 eq.), NaI (1.0 mol %) and cesium carbonate (3 eq.). The reaction mixture was heated in a pressure tube at 150° C. overnight. The completion of the reaction was confirmed by LCMS. The reaction mixture was then diluted with ethyl acetate, washed with water and extracted with ethyl acetate (3×). The combined organic layer was dried over sodium sulfate, filtered, and concentrated to yield the crude product which was used in the next step without further purification.

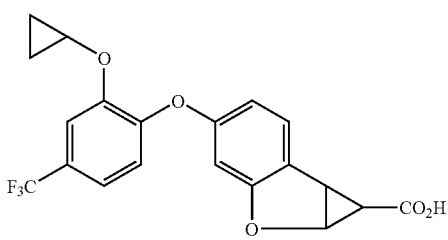

Step 2

4-[2-(Cyclopropyloxy)-4-(trifluoromethyl)phenoxy]-1a,6b-dihydro-1H-cyclopropa[b][1]benzofuran-1-exo-carboxylic acid Follows the method of Example 1 or Example 3. MS: 393.0 (M+1).

Example 11

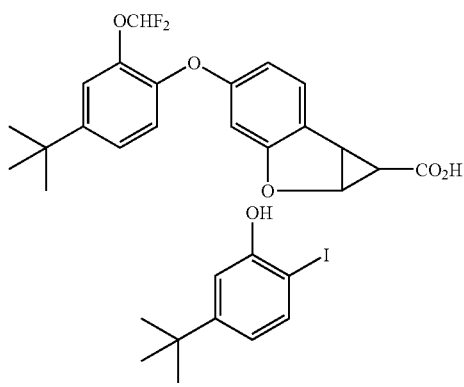

Step 1

To a solution of 3-(tert-butyl)phenol (3 g, 20 mmol) in methanol (40 mL) was added iodine (5.58 g, 22 mmol) in portions, and the mixture was stirred for 48 hours at room temperature. Solvent was removed and the residue was dissolved in ethyl acetate (200 mL). The solution was washed with $Na_2SO_3$ (3×) and brine, dried over $MgSO_4$ and concentrated. The residue was purified with a silica gel column chromatography with ethyl acetate/hexanes (10-20%) as the eluant to afford the desired product.

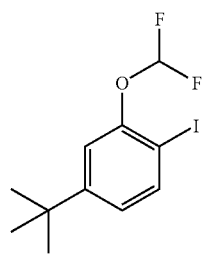

Step 2

Sodium chlorodifluoroacetate (4 g, 26.17 mmol) and cesium carbonate (5.1 g, 15.7 mmol) were added to a solution of 5-(tert-butyl)-2-iodo-1-phenol (2.89 g, 10.47 mmol) in DMF containing 10 volume % water (22 mL), and the reaction mixture was heated for 3 days at 100° C. in a sealed tube. After cooling to room temperature, the reaction mixture was diluted with ethyl acetate and washed with water (3×) and brine (1×). The organic layer was dried over $MgSO_4$ and concentrated. The residue was purified with a silica gel column chromatography with ethyl acetate/hexanes (0-10%) as the eluant to afford the desired product.

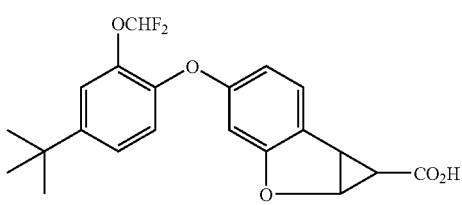

Step 3

4-[4-tert-Butyl-2-(difluoromethoxy)phenoxy]-1a,6b-dihydro-1H-cyclopropa[b][1]benzofuran-1-exo-carboxylic acid Follows the method of Example 2. MS: 391.0 (M+1).

Example 12

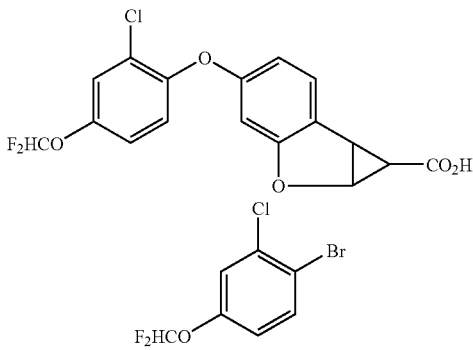

Step 1

1-Bromo-2-chloro-4-(difluoromethoxy)benzene

Follows the method of Example 3, Step 1

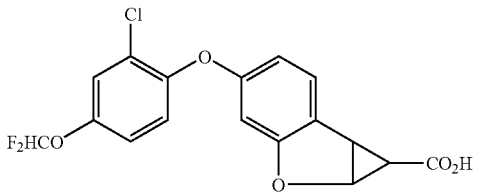

Step 2

4-[2-Chloro-4-(difluoromethoxy)phenoxy]-1a,6b-dihydro-1H-cyclopropa[b][1]benzofuran-1-exo-carboxylic acid Follows the method of Example 2. MS: 369.2 (M+1).

Example 13

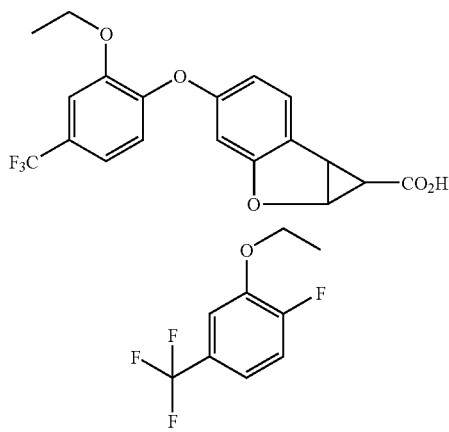

Step 1

To a solution of 2-fluoro-5-trifluoromethyl phenol in DMF (2 mL) was added iodoethane (2 eq.) and cesium carbonate (3 eq.). The reaction mixture was heated at 75° C. overnight. The completion of the reaction was confirmed by LCMS. The reaction mixture was then diluted with ethyl acetate, washed with water and extracted with ethyl acetate (3×). The combined organic layer was dried over sodium sulfate, filtered and concentrated to yield the crude product which was used in the next step without further purification.

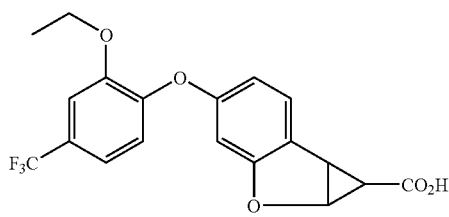

Step 2

4-[2-ethoxy-4-(trifluoromethylyphenoxy]-1a,6b-dihydro-1H-cyclopropa[b][1]benzofuran-1-exo-carboxylic acid Follows the method of Example 1 or Example 3. MS: 381.0 (M+1).

Example 14

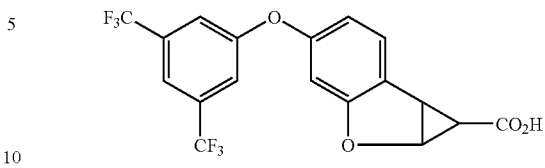

4-[3,5-Bis(trifluoromethyl)phenoxy]-1a,6b-dihydro-1H-cyclopropa[b][1]benzofuran-1-exo-carboxylic acid Follows the method of Example 2. MS: 403.9 (M+1).

Example 15

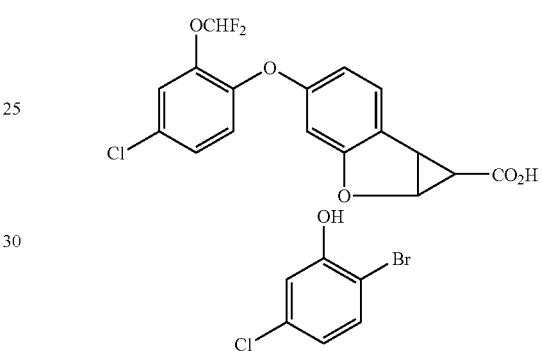

Step 1

2-Bromo-5-chloroanisole (461 mg, 2.08 mmol) was dissolved in anhydrous dichloromethane (5 mL) and cooled to 0° C. To the cooled solution was added boron tribromide solution (1M in dichloromethane, 2 eq). The reaction mixture was stirred at 0° C. for 5 minutes, warmed to room temperature and stirred at room temperature for 2 hours. The reaction mixture was then poured into ice-water and extracted with ethyl acetate (3×). The combined organic layer was then dried over sodium sulfate, filtered and concentrated to get the crude phenol which was used in the next step without further purification.

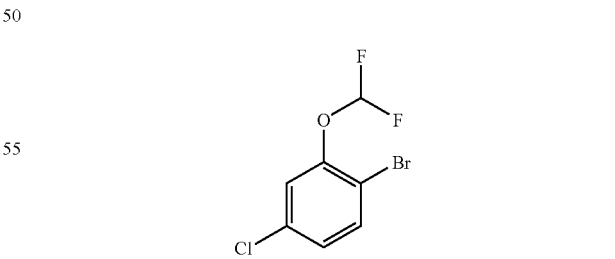

Step 2

Sodium chlorodifluoroacetate (2.5 eq.) and cesium carbonate (1.5 eq.) were added to a solution of 2-bromo-5-chlorophenol in DMF containing 10 volume % water, and the reaction mixture was heated for 3h at 100° C. After cooling to room temperature, the reaction mixture was diluted with ethyl acetate and washed with water (3×), then with brine (1×). The organic layer was dried over sodium sulfate and concentrated to obtain the crude product which was used in the next step without further purification.

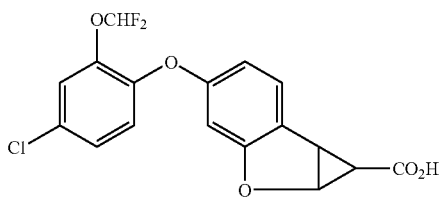

Step 3

4-[4-Chloro-2-(difluoromethoxy)phenoxy]-1a,6b-dihydro-1H-cyclopropa[b][1]benzofuran-1-exo-carboxylic acid Follows the method of Example 2. MS: 369.2 (M+1).

Example 16

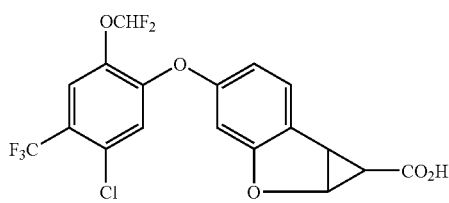

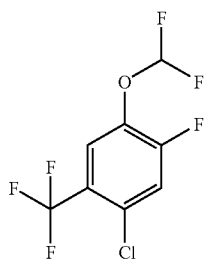

Step 1

Sodium chlorodifluoroacetate (692 mg, 4.54 mmol) and cesium carbonate (888 mg, 2.73 mmol) were added to a solution of 6-fluoro-3-trifluoromethyl-4-chlorophenol in DMF containing 10 volume % water (3 mL), and the reaction mixture was heated for 1 h at 100° C. After cooling to room temperature, the reaction mixture was diluted with ethyl acetate and washed with water (3×), brine (1×). The organic layer was dried over MgSO$_4$ and concentrated to obtain the crude product which was used in the next step without further purification.

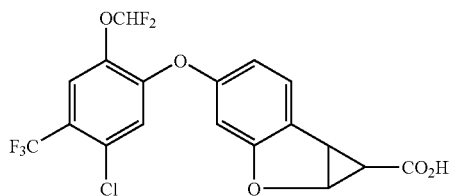

Step 2

4-[5-Chloro-2-(difluoromethoxy)-4-(trifluoromethyl)phenoxy]-1a,6b-dihydro-1H-cyclopropa [b][1]benzofuran-1-exo-carboxylic acid Follows the method of Example 1 or Example 3. MS: 437.1 (M+1).

Example 17

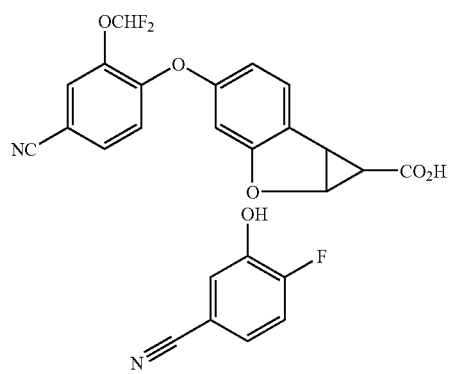

Step 1

4-fluoro-3-methoxybenzonitrile (1 g, 6.62 mmols) was dissolved in anhydrous dichloromethane (10 mL) and cooled to 0° C. (ice-bath). To the cooled solution was added boron tribromide solution in dichloromethane (1 M, 2 eq.). The reaction mixture was stirred at 0° C. for 5 minutes, warmed to room temperature and stirred at room temperature overnight. LCMS of the reaction mixture showed some starting material was still present. Two more equivalents of boron tribromide solution was added and the reaction was stirred at RT overnight. LCMS showed that the reaction had progressed, but some starting material was still present. The reaction mixture was then heated at 45° C. overnight to complete the reaction, as confirmed by LCMS. The reaction mixture was then poured into ice-water, warmed to RT, and extracted with ethyl acetate (3×). The combined organic layer was dried over sodium sulfate, filtered and concentrated to give the crude phenol which was used in the next step without further purification.

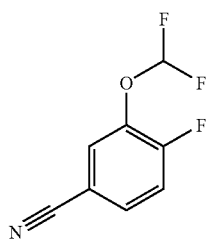

Step 2

Sodium chlorodifluoroacetate (2.5 eq.) and cesium carbonate (1.5 eq.) were added to a solution of 2-fluoro-5-cyanophenol in DMF containing 10 volume % water, and the reaction mixture was heated for 3 h at 100° C. After cooling to room temperature, the reaction mixture was diluted with ethyl acetate and washed with water (3x), then with brine (1x). The organic layer was dried over sodium sulfate and concentrated to obtain the crude product which was used in the next step without further purification.

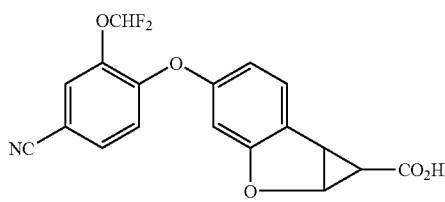

Step 3

4-[4-Cyano-2-(difluoromethoxy)phenoxy]-1a,6b-dihydro-1H-cyclopropa[b][1]benzofuran-1-exo-carboxylic acid Follows the method of Example 1 or Example 3. MS: 359.9 (M+1).

Example 18

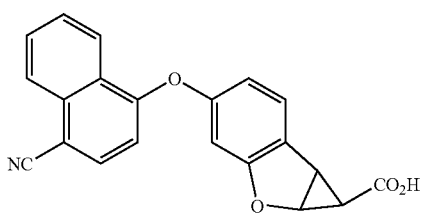

4-[(4-Cyano-1-naphthyl)oxy]1-1a,6b-dihydro-1H-cyclopropa[b][1]benzofuran-1-exo-carboxylic acid Follows the method of Example 1. MS: 344.0 (M+1).

Example 19

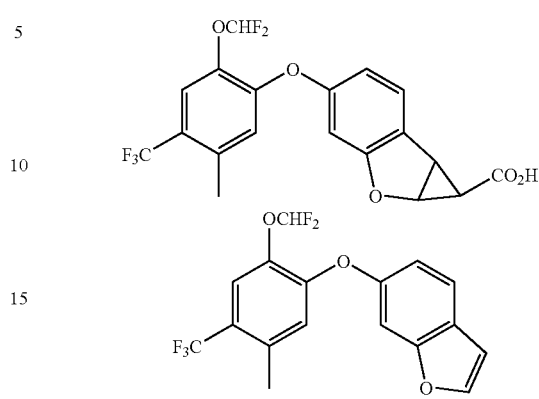

Step 1

6-[2-(Difluoromethoxy)-5-methyl-4-(trifluoromethyl)phenoxy]-1-benzofuran

To a solution of the material obtained from step 2 of Example 16 (50 mg, 0.132 mmol) in DMF (1 mL) were added methyl boronic acid (12 mg, 0.2 mmol), cesium carbonate (129 mg, 0.4 mmol), and Pd(PPh$_3$)$_4$ (30.5 mg, 0.026 mmol). The mixture was degassed, flushed with nitrogen, and heated to 120° C. for 5 hours. Solvent was removed and the residue was purified with silica gel column chromatography using hexanes/ethyl acetate as the eluant (10/1) to afford the desired compound.

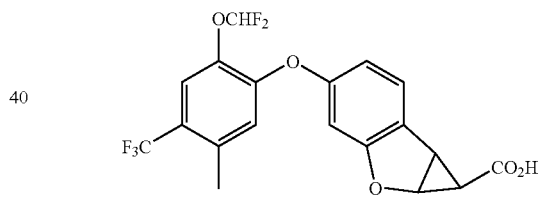

Step 2

4-[2-(Difluoromethoxy)-5-methyl-4-(trifluoromethyl)phenoxy]-1a,6b-dihydro-1H-cyclopropa[b][1]benzofuran-1-exo-carboxylic acid Follows the methods of Example 1, steps 2 and 3, and Example 3, steps 3 and 4. MS: 417.0 (M+1).

Example 20

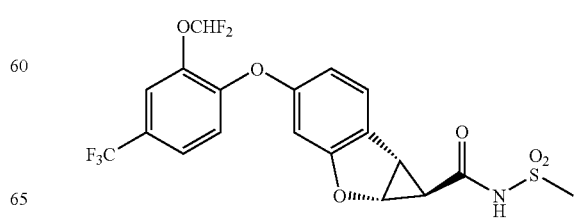

(1R,1aR,6bS)-4-[2-(difluoromethoxy)-4-(trifluoromethyl)phenoxy]-N-(methylsulfonyl)-1a,6b-dihydro-1H-cyclopropa[b][1]benzofuran-1-carboxamide To a stirred solution of the corresponding acid (Example 3, 30 mg, 0.075 mmol) in acetonitrile (1.5 mL) was added N-hydroxysuccinimide (9.5 mg, 0.082 mmol) and EDC (15.7 mg, 0.081 mmol). The mixture was stirred at room temperature for 3 days, and the N-hydroxysuccinimide ester intermediate (30 mg) was isolated. It was dissolved in dichloromethane (1 mL) and treated with DMAP (catalytic amount) and methanesulfonamide (11.4 mg, 0.12 mg). The reaction was stirred at 50° C. overnight. The final product was isolated by reverse phase LC on a C18 column, followed by preparative TLC on silica gel plates, which were developed in 10% MeOH in dichloromethane. MS: 480.1 (M+1).

Example 21

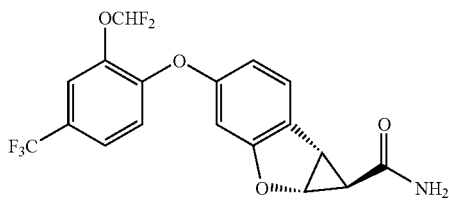

(1R,1aR,6bS)-4-[2-(Difluoromethoxy)-4-(trifluoromethyl)phenoxy]-1a,6b-dihydro-1H-cyclopropa[b][1]benzofuran-1-carboxamide To a stirred solution of the corresponding acid (Example 3, 402 mg, 1.0 mmol) in acetonitrile (15 mL) was added N-hydroxysuccinimide (126.6 mg, 1.1 mmol) and EDC (210.9 mg, 1.1 mmol). The mixture was stirred at room temperature for 16 h, and then ammonium hydroxide (0.2 mL, 3 mmol) was added. The reaction was stirred at room temperature for 3 h. After precipitates were filtered off, the crude product was purified on a silica gel column, eluting with methanol (0-10%) in dichloromethane. The final product was collected as white solid. MS: 402.3 (M+1).

Example 22

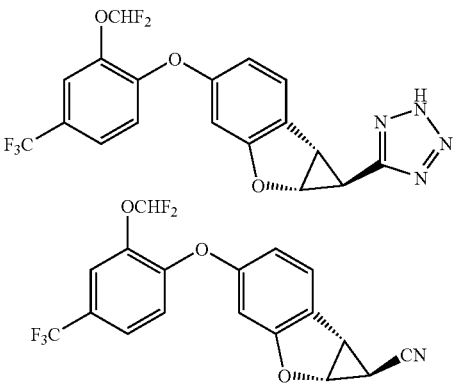

Step 1

5-{(1S,1aR,6bS)-4-[2-(difluoromethoxy)-4-(trifluoromethyl)phenoxy]-1a,6b-dihydro-1H-cyclopropa[b][1]benzofuran-1-carbonitrile To a stirred solution of the corresponding amide (Example 21, 386 mg, 0.96 mmol) in DMF (5 mL) was added cyanuric chloride (89 mg, 0.48 mmol). The reaction was stirred at room temperature for 2h. After aqueous workup, the crude product was purified on a silica gel column, eluting with ethyl acetate (0-30%) in hexanes. The final product was collected as colorless oil.

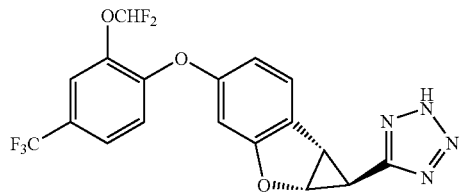

Step 2

5-{(1S,1aR,6bS)-4-[2-(Difluoromethoxy)-4-(trifluoromethyl)phenoxy]-1a,6b-dihydro-1H-cyclopropa[b][1]benzofuran-1-yl}-2H-tetrazole To a stirred solution of the above nitrile (82.8 mg, 0.216 mmol) in 2-propanol (1.25 mL) and water (2.5 mL) was added sodium azide (70.2 mg, 1.08 mmol) and zinc bromide (73 mg, 0.32 mmol). The reaction was stirred at 100° C. overnight. The crude product was collected by filtration as yellowish precipitates. The pure product was isolated by reverse phase LC on a C18 column as white solid.

Scheme 4: 2-Methyl Benzofuran Derivatives

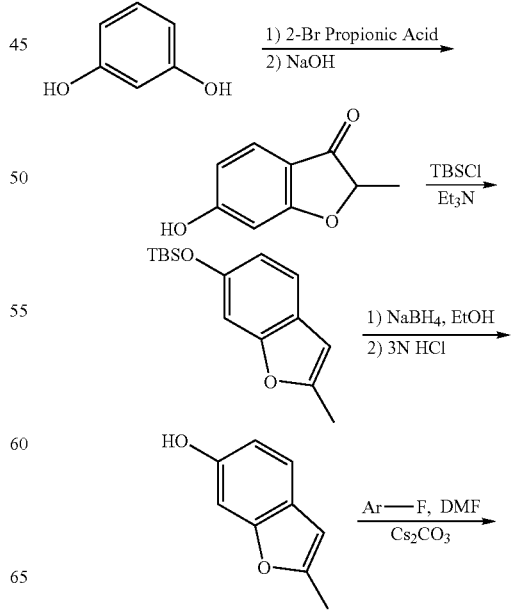

-continued

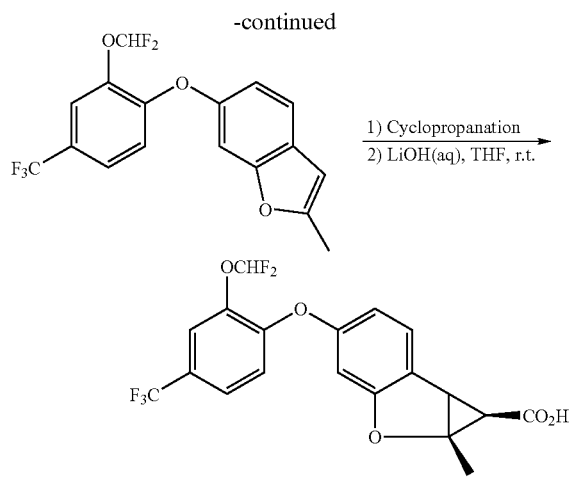

Example 23

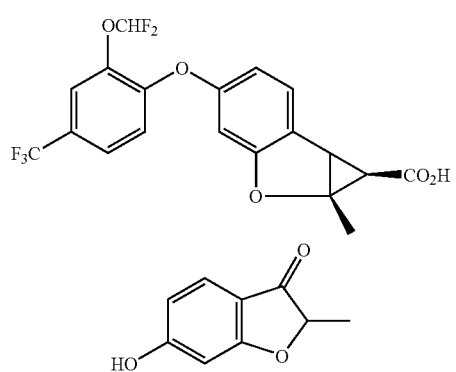

Step 1

6-Hydroxy-2-methyl-1-benzofuran-3(2H)-one

To a stirred solution of resorcinol (5.5 g, 50 mmol) in methanesulfonic acid (75 mL) was added 2-bromopropionic acid (4.7 mL, 50 mmol) and $P_2O_5$ (4.0 g, 28 mmol). The resulting mixture was stirred for 30 min at 80° C. After cooling to room temperature, the reaction mixture was poured onto ice and extracted with chloroform (2×). The combined organic extracts were washed with brine, dried with sodium sulfate, and concentrated. The orange colored crude product (~12 g) was carefully taken up into aqueous sodium hydroxide (2N, 245 mL) at 0-5° C., and the resulting mixture was stirred at room temperature overnight. The dark brown solution was cooled to 0° C., and carefully acidified to with concentrated HCl to pH ~3. It was then extracted with ethyl acetate (3×). The combined organic extracts were washed with brine, dried with sodium sulfate, and concentrated. The crude material was purified on a silica gel column, eluting with ethyl acetate (20-75%) in hexanes. The final product was obtained as a crystalline solid upon standing at room temperature. The NMR showed a mixture of tautomers (mostly the enol form).

Step 2

6-tert-Butyldimethylsiloxy-2-methyl-1-benzofuran-3 (2H)-one

To a stirred solution of the above ketone (3.6 g, 21 mmol) in acetonitrile (40 mL) was added tert-butyldimethylsilyl chloride (3.4 g, 22.5 mmol) and triethylamine (3.5 mL, 25 mmol). The mixture was stirred at room temperature for 18 h. After normal aqueous workup, the crude product was purified on a silica gel column, eluting with ethyl acetate (10-50%) in hexanes. The final product was collected as colorless oil.

Step 3

2-Methyl-1-benzofuran-6-ol

To a stirred solution of the above ketone (250 mg, 0.9 mmol) in ethanol (5 mL) was added sodium borohydride (100 mg, 2.6 mmol). The mixture was stirred at room temperature overnight. Hydrochloric acid (5 mL, 3N) was carefully added, and the reaction was stirred at room temperature for another day. After normal aqueous workup, the crude product was purified on a silica gel column, eluting with ethyl acetate (5-45%) in hexanes. The final product was collected as crystalline solid.

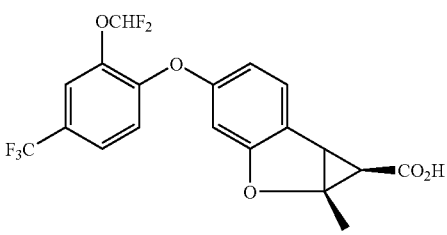

Step 4

4-[2-(Difluoromethoxy)-4-(trifluoromethyl)phenoxy]-1a-methyl-1a,6b-dihydro-1H-cyclopropa[b][1] benzofuran-1-exo-carboxylic acid Follows the method of Example 3. The final product was purified on a ChiralPak AD-H semi-preparative column, eluting with 4-7% ethanol in heptane. MS: 417.3 (M+1).

47

Scheme 5: 3-Methyl Benzofuran Derivatives

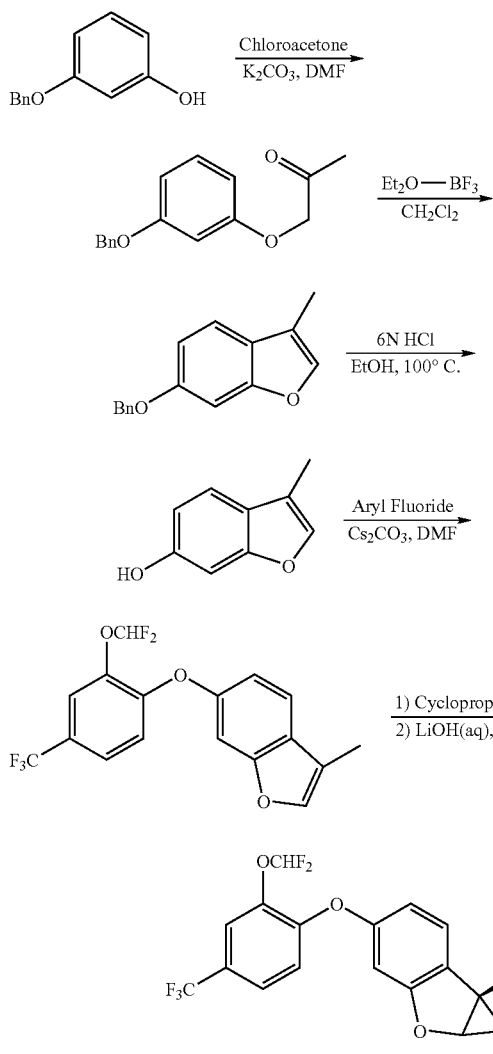

Example 24

48

Step 1

1-[3-(benzyloxy)phenoxy]acetone

Follows the method of Example 1, step 1.

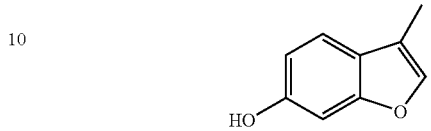

Step 2

3-Methyl-1-benzofuran-6-ol

To a stirred solution of the above ketone (1.6 g, 6.2 mmol) in dichloromethane (250 mL) was slowly added a solution of boron trifluride etherate (0.95 mL, 7.5 mmol) in dichloromethane (50 mL) over a period of 1 h. The resulting dark blue solution was stirred at room temperature for another hour. The reaction was carefully quenched with sodium bicarbonate (aq, sat.). After normal aqueous workup, the crude product was purified on a silica gel column, eluting with ethyl acetate (5-25%) in hexanes. The final product was collected as white solid.

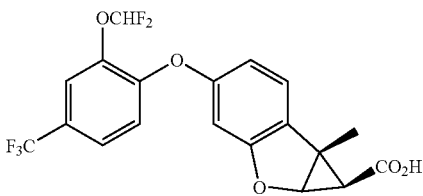

Step 3

4-[2-(Difluoromethoxy)-4-(trifluoromethyl)phenoxy]-6b-methyl-1a,6b-dihydro-1H-cyclopropa[b][1]benzofuran-1-exo-carboxylic acid Follows the method of Example 3. The final product was purified on ChiralPak AD-H semi-preparative column, eluting with 4-7% ethanol in heptane. MS: 417.2 (M+1).

Example 25

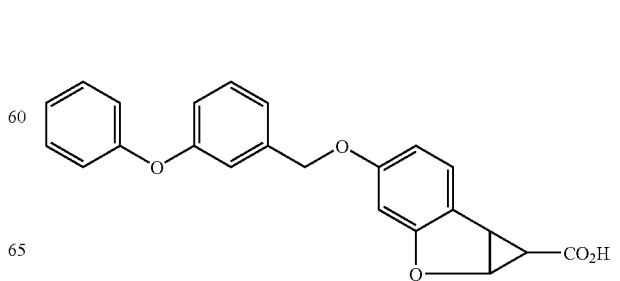

4-[(3-Phenoxybenzyl)oxy]-1a,6b-dihydro-1H-cyclopropa[b][1]benzofuran-1-exo-carboxylic acid Follows the method of Example 1. MS: 375.3 (M+1).

Example 26

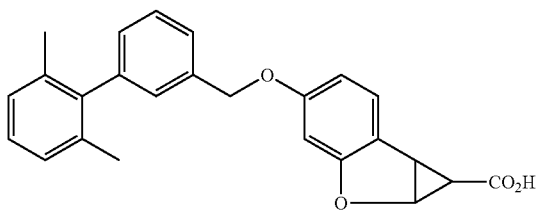

4-[(2',6'-Dimethylbiphenyl-4-yl)oxy]-1a,6b-dihydro-1H-cyclopropa[b][1]benzofuran-1-exo-carboxylic acid Follows the method of Example 1. The final product was purified on ChiralPak AD-H semi-preparative column, eluting with 4-7% ethanol in heptane. MS: 387.2 (M+1).

Example 27

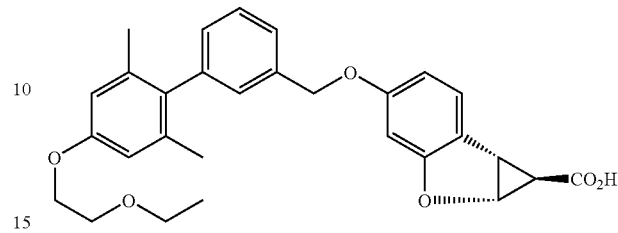

4-1[4'-(2-Ethoxyethoxy)-2',6'-dimethylbiphenyl-3-yl]methoxyl-1a,6b-dihydro-1H-cyclopropa[b][1]benzofuran-1-exo-carboxylic acid Follows the method of Example 3. The final product was purified on ChiralPak AD-H semi-preparative column, eluting with 4-7% ethanol in heptane. MS: 473.3 (M−1).

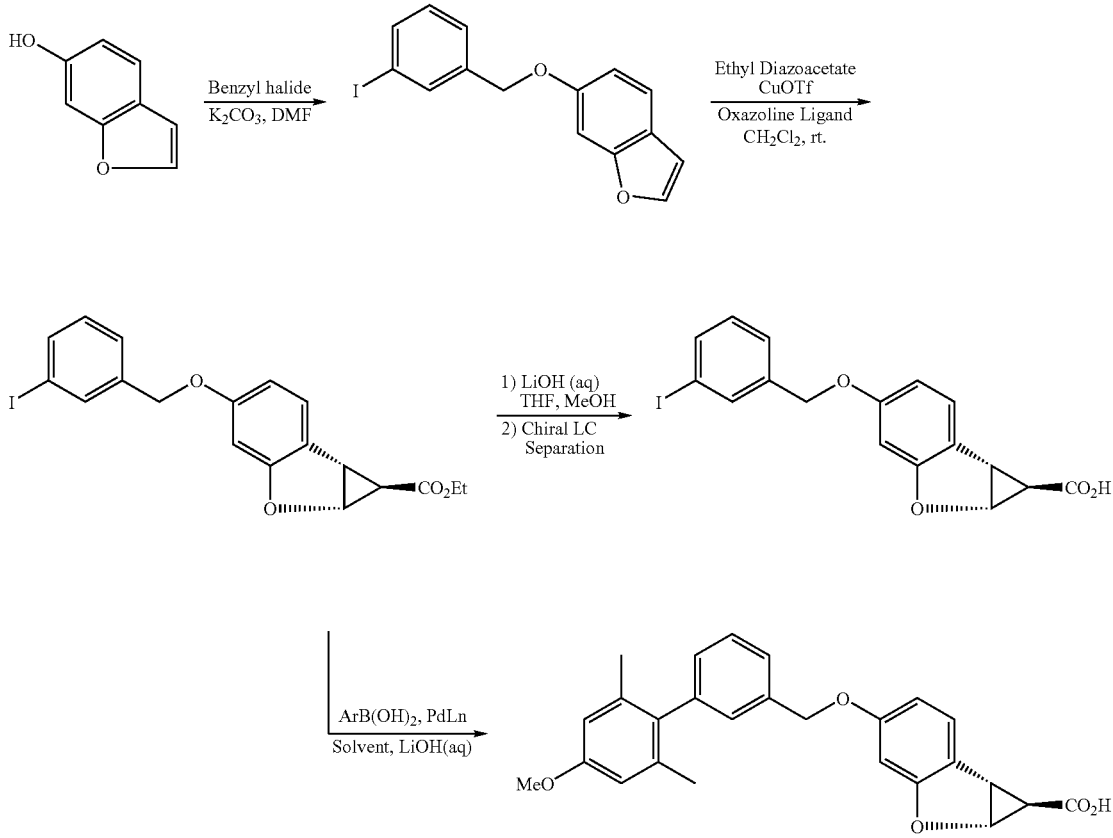

Example 28

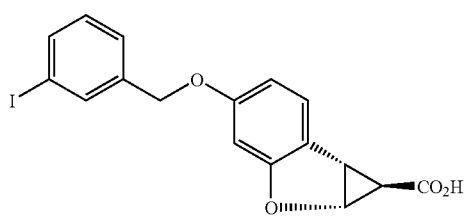

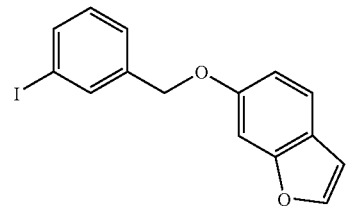

Step 1

6-[(3-iodobenzyl)oxy]-1-benzofuran

To a stirred solution of 1-benzofuran-6-ol (1.0 g, 7.5 mmol) and 3-iodobenzylbromide (2.7 g, 9.0 mmol) in DMF (10 mL) was added potassium carbonate (1.5 g, 11.0 mmol). The reaction mixture was stirred under nitrogen at room temperature for 3 days. The reaction was diluted with ethyl acetate, washed with water (2×) and brine, dried over magnesium sulfate, filtered and concentrated. The crude product was purified on a silica gel column, eluting with ethyl acetate (10-50%) in hexane. The final product was collected as a slightly yellow viscous oil.

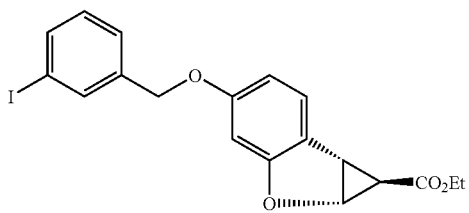

Step 2

Ethyl 4-[(3-iodobenzyl)oxy]-1a,6b-dihydro-1H-cyclopropa[b][1]benzofuran-1-exo-carboxylate (Intermediate A)

Follows the method of Example 3, Step 3. The desired trans (or exo-) diastereomer was obtained as slightly yellow crystalline solid.

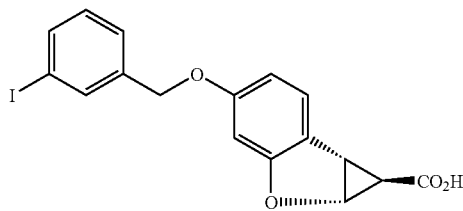

Step 3

4-[(3-Iodobenzal)oxy]-1a,6b-dihydro-1H-cyclopropa[b][1]benzofuran-1-exo-carboxylic acid Follows the method of Example 1, Step 3. The final product was obtained as a slightly colored solid. MS: 409.1 (M+1).

Example 29

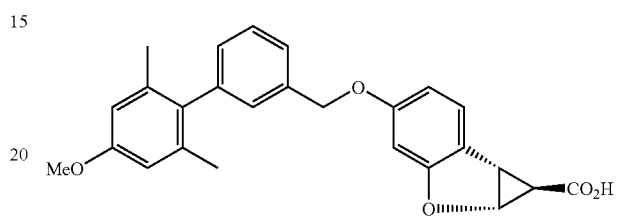

(1R,1aR,6bS)-4-[(4'-methoxy-2',6'-dimethylbiphenyl-3-yl)methoxy]-1a,6b-dihydro-1H-cyclopropa[b][1]benzofuran-1-carboxylic acid To a solution of the ethyl ester from Step 2, Example 28 (Intermediate A) (50 mg, 0.11 mmol) in dioxane (2 mL) was added dppf (10 mg, 0.011 mmol) and 2,6-dimethyl-4-methoxybenzene boronic acid (20 mg, 0.12 mmol), followed by LiOH (0.6 mL, 2 N, 0.12 mmol). The reaction was sealed and stirred at 80° C. overnight. After cooling to room temperature, the reaction was quenched with ammonium chloride (aq. sat.). Organic layer was separated and injected directly onto a C18 reverse phase column, eluting with acetonitrile and 0.1% TFA in water. The desired product was isolated as a light blue solid after lyophilization. MS: 417.3 (M+1).

Alternate Synthesis of 2-(Difluoromethoxy)-1-fluoro-4-trifluoromethylbenzene

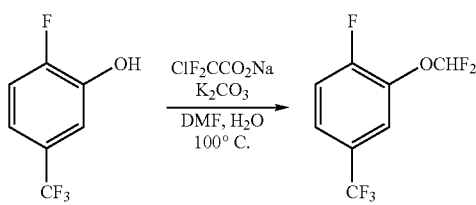

A 100-L round bottom flask equipped with overhead stirrer, thermocouple, nitrogen inlet, condenser and steam bath was charged with 2-fluoro-5-(trifluoromethyl)phenol (5.50 kg), sodium chlorodifluoroacetate (9.31 kg), and DMF (4 L). There was an exotherm to 46.7° C. when the 4 L of DMF was charged to the flask. The temperature of the reaction was immediately reduced to 19° C. by rapid cooling with an ice/water bath. An additional 37.3 L of DMF (total DMF, 41.3 L) was then slowly charged, maintaining the internal temperature below 30° C. After cooling to ambient temperature, water (5.5 L) was charged, resulting in a 10° C. exotherm. Potassium carbonate (5.28 kg) was then added. The ice water bath was removed and the batch was heated to 97° C. using a steam bath. The reaction was complete after aging for 2 h at 97° C., as evidenced by HPLC assay, with <1% starting material remaining. The reaction was cooled to ambient temperature, and water (42 L) was slowly added. The batch was transferred to a 170-L extractor and extracted with MTBE (2×18 L). The organic layers were combined and washed with water (1×11 L) and brine (1×11 L). The MTBE solution was pumped into a 22-L flask equipped with a thermocouple, distillation apparatus, and a heating mantle. The MTBE was distilled off at 55-118° C. and atmospheric pressure. The desired product was purified by distillation at 120-157° C. and atmospheric pressure, and was isolated as a clear oil.

Alternate Synthesis of 6-[2-(Difluoromethoxy)-4-(trifluoromethyl)phenoxy]-1-benzofuran

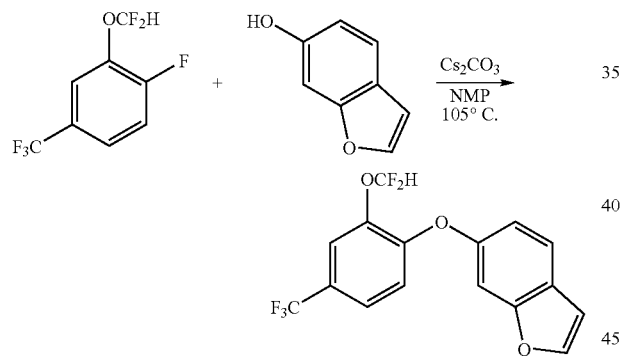

2-(Difluoromethoxy)-1-fluoro-4-trifluoromethylbenzene (5207 g), 1-benzofuran-6-ol (2767 g), and $Cs_2CO_3$ (13.44 kg) in 13.8L of N-methylpyrrolidinone (NMP) were charged to a 100L RBF. An exotherm to 40° C. occurred after they were mixed. The mixture was warmed to 105° C. and aged for 7 h at that temperature. The mixture was cooled to ambient temperature, and then toluene (34 L) and water (34 L) were added. The organic layer was washed first with 1N NaOH (7.5 L) and then with 15 wt. % brine (6 L). The organic layer was concentrated to ~28 L. The amount of water by Karl-Fischer titration was <200 ug/mL. The toluene solution was filtered through a plug of $SiO_2$ (5.0 kg). The silica was washed with toluene (14.2 L). The filtrate was concentrated on a rotary evaporator to yield 6-[2-(difluoromethoxy)-4-(trifluoromethyl)phenoxy]-1-benzofuran biaryl ether as a light orange oil.

Alternate Synthesis of (1R,1aR,6bS)-4-[2-(difluoromethoxy)-4-(trifluoromethyl)phenoxy]-1a,6b-dihydro-1H-cyclopropa[b][1]benzofuran-1-carboxylic acid Step 1

Asymmetric Cyclopropanation to give Ethyl (1R,1aR,6bS)-4-[2-(difluoromethoxy)-4-(trifluoromethyl)phenoxy]-1a,6b-dihydro-1H-cyclopropa[b][1]benzofuran-1-carboxylate

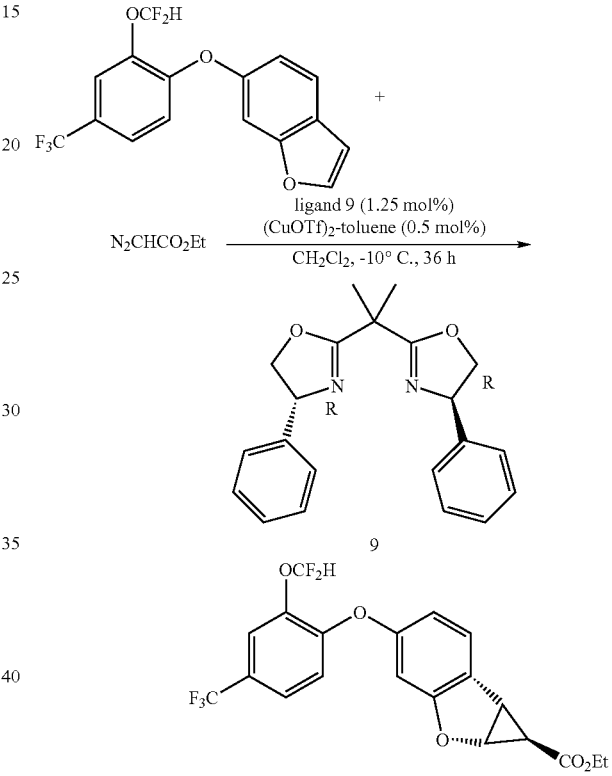

Dichloromethane (18 L), the ligand (R)-(+)-2,2'-isopropylidene-bis-(4R)-4-phenyl-2-oxazoline (66.8 g), and (CuOTf)2.toluene complex (41.3 g) were charged to a 100 L cylinder, which was equipped with an overhead stirrer, thermocouple, dropping funnel, and nitrogen inlet. The reaction mixture was aged at 23° C. until it became an almost homogeneous green solution with a small amount of solid on the bottom (typically 2-6 h is needed). The phenoxybenzofuran (6.031 kg, 91.35 wt %, 92.0 Assay % purity, 26.9 ppm water by Karl Fischer titration) was rinsed into the reactor with dichloromethane (4 L). The reaction mixture was aged at rt for 0.5 h, and was then cooled to −9 to −12° C. Ethyl diazoacetate in dichloromethane (85 wt %, 5.64 kg, 2.63 equiv) was slowly added to the reaction mixture at −9° C. to −12° C. over 30 h, resulting in 96A % conversion to the desired product with a ratio of exo:endo of about 29.3:1. The reaction mixture was slowly warmed to ambient temperature, and aged for 0.5 h. EDTA disodium salt solution (0.05M, 18 L) was added, and the reaction mixture was aged for 1 h at 20° C. The phases were separated, and the organic layer was washed with additional 0.05 M EDTA sodium salt solution (8 L). The desired exo product in the organic layer was assayed to be 6.17 kg (90% yield, 92.1% ee). The solution was concentrated and the solvent was switched to methanol (25 L, total volume) for the next step.

Step 2

Ester Hydrolysis Isolation as a cis-Aminoindanol (CAI) salt

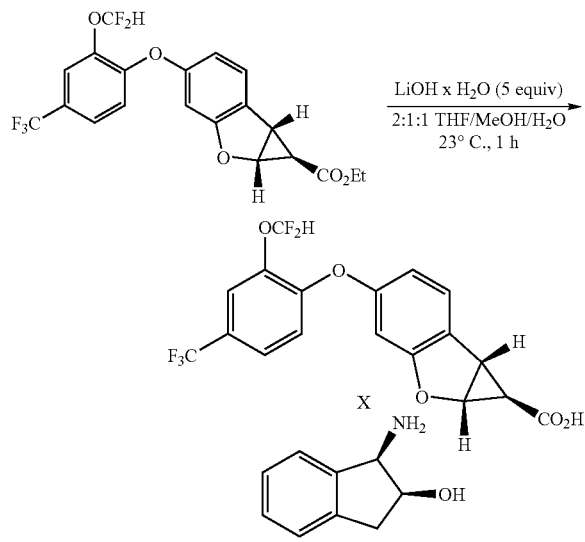

THF (30 L), water (15 L), and LiOH (5 equiv.) were added to a 100 L RBF containing the solution of the ester from the previous step in MeOH. The mixture immediately became dark and exothermed to 38° C. The reaction was aged for 3 h at ambient temperature and was then transferred to a cylindrical reaction vessel. Toluene (30 L) and 5 N HCl (1.1 equiv.) were added, and the layers were separated. The organic layer was washed with water (2×30 L). The organic layer was then concentrated to ~29L with azeotropic removal of water. LiCl precipitate formed during the concentration. Ecosorb C905 (50 wt %, 2.89 kg) was added to the thin slurry, and the mixture was then aged at ambient temperature for 2 h, filtered through solka floc, and rinsed with toluene (23 L). The filtrate was concentrated to 29 L, and (R,S)-CAI, (R,S)-cis-aminoindanol (0.96 equivalents compared with the assayed amount of hydrolyzed ester) was added. The mixture was warmed to 85° C. to dissolve all solids. The mixture was then cooled to 75° C., and the CAI salt began to crystallize. The mixture was aged 15 min at 75° C., and then heptane (13.5 L) was added over 1 h. The mixture was allowed to slowly cool to rt. The mixture was filtered. The solid product was washed with 2:1 toluene/heptane (18 L), and was then dried under nitrogen for 5 days. The isolated product was 98.6% pure solid, 98.0% ee.

The CAI salt (5900 g of 98.6 wt.% product from above) was dissolved in toluene (53 L) at 85° C. and was then cooled to 70° C. to give a thin slurry. Heptane (18L) was added over 1 h while maintaining the temperature at 65-70° C. The mixture was allowed to cool to rt over 3 h and was then filtered. The filter cake was dried under nitrogen for 2 days. The isolated product purity was >99A % and 98.8% ee.

Step 3

(1R,1aR,6bS)-4-[2-(difluoromethoxy)-4-(trifluoromethyl)phenoxy]-1a,6b-dihydro-1H-cyclopropa[b][1]benzofuran-1-carboxylic acid

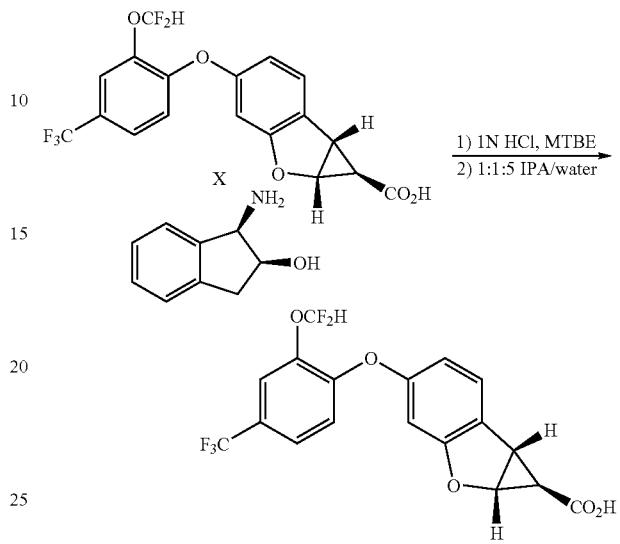

The CAI salt from the previous step (5463 g) was added to a 100 L cylindrical vessel which contained a mixture of MTBE (27.3 L) and 10.9 L of IN HCl (1.1 equiv.). After being stirred vigorously for 15 min, the aqueous layer was allowed to settle, and the layers were separated. The organic layer was washed with 11.8 L of water. The organic layer was then solvent switched to IPA (16 L). Water (8 L) was added in one portion, and then 1% seed (obtained from earlier batches) was added. (The product crystallizes without seed if none is available.) After 15 min, water (32 L) was added over 1 h. The mixture was aged 14 h, and then was filtered, washed with 2:3 IPA/water (15 L), and dried under nitrogen for 20 h. The product purity was 99.78 A %, 98.6% ee. The product is a crystalline anhydrous free acid which is characterized by the methods described below. The crystalline product has the same crystal morphology as the product isolated in Example 3.

Characterization of the Crystalline Free Acid of Example 3.

X-ray powder diffraction studies are widely used to characterize molecular structures, crystallinity, and polymorphism. The X-ray powder diffraction pattern of the crystalline anhydrous free acid of Example 3 made by the process described above was generated on a Philips Analytical X'Pert PRO X-ray Diffraction System with PW3040/60 console. A PW3373/00 ceramic Cu LEF X-ray tube K-Alpha radiation was used as the source.

FIG. 1 shows the X-ray diffraction pattern of the crystalline anhydrous free acid of Example 3 made by the process described above. The crystalline anhydrous free acid exhibited characteristic diffraction peaks corresponding to d-spacings of 9.7, 6.1, and 5.6 angstroms. It was further characterized by d-spacings of 4.8, 4.4 and 4.1 angstroms. It was even further characterized by d-spacings of 3.7, 3.4, and 3.2 angstroms.

The crystalline anhydrous free acid of Example 3 made by the process described above was further characterized by its solid-state carbon-13 nuclear magnetic resonance (NMR) spectra. The solid-state carbon-13 NMR spectrum was obtained on a Bruker DSX 500WB NMR system using a Bruker 4 mm H/X/Y CPMAS probe. The carbon-13 NMR spectrum utilized proton/carbon-13 cross-polarization magic-angle spinning with variable-amplitude cross polarization, total sideband suppression, and SPINAL decoupling at 100 kHz. The sample was spun at 10.0 kHz, and a total of 512 scans were collected with a recycle delay of 30 seconds. A line broadening of 10 Hz was applied to the spectra before FT was performed. Chemical shifts are reported on the TMS scale using the carbonyl carbon of glycine (176.03 p.p.m.) as a secondary reference.

Figure 2:
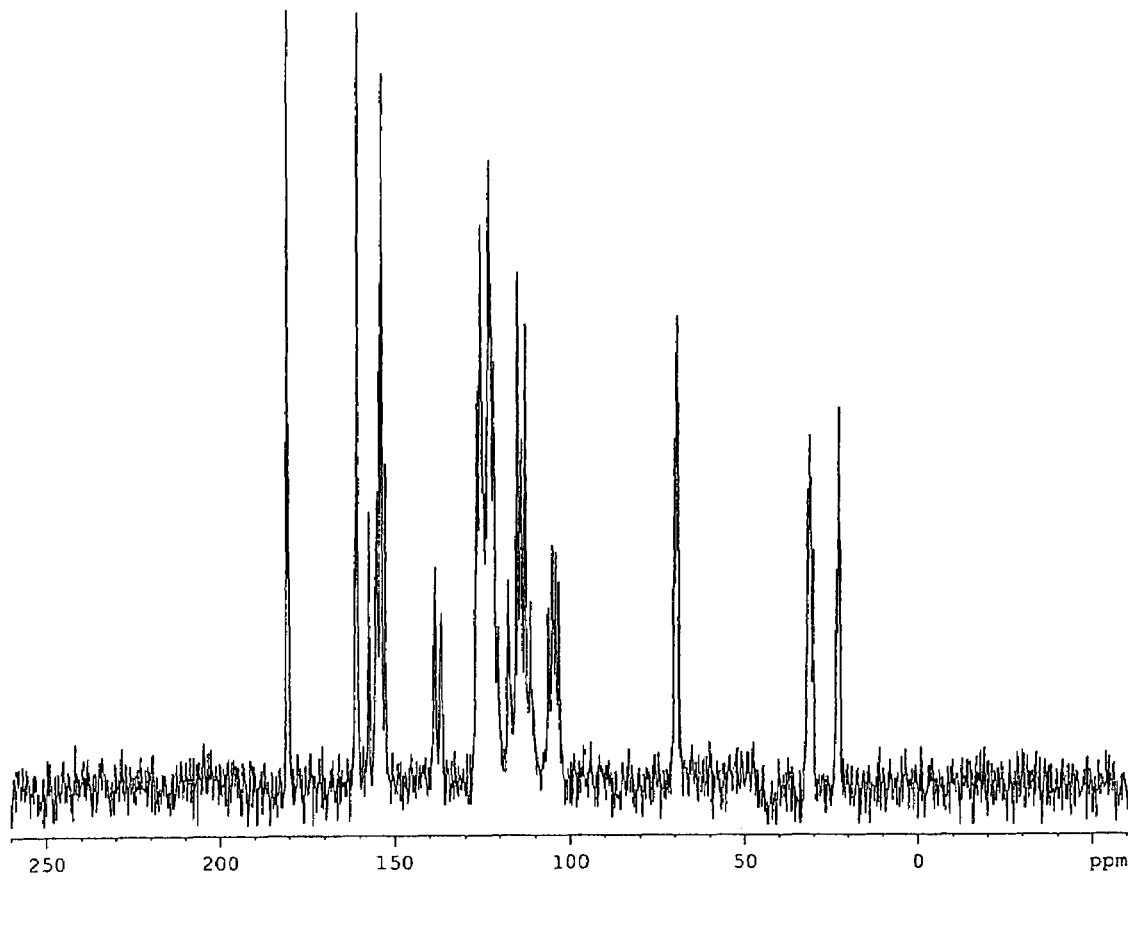
FIG. 2 is a typical carbon-13 cross-polarization magic-angle spinning (CPMAS) nuclear magnetic resonance (NMR) spectrum of the crystalline anhydrous free acid of Example 3.

FIG. 2 shows the solid-state carbon-13 CPMAS NMR spectrum of the crystalline anhydrous free acid of the product made by the process described above. The crystalline anhydrous free acid exhibited characteristic signals with chemical shift values of 180.9, 153.7, 69.7, and 23.0 p.p.m. Further characteristic of the crystalline free acid are the signals with chemical shift values of 160.9, 123.5, and 31.5 p.p.m. The crystalline free acid is even further characterized by signals with chemical shift values of 125.8, 112.9, and 115.2 p.p.m.

DSC data for the crystalline free acid of Example 3 made by the process described above were acquired at a heating rate of 10° C./min under nitrogen atmosphere in a closed pan using TA Instruments DSC 2910 or equivalent instrumentation.

Figure 3:
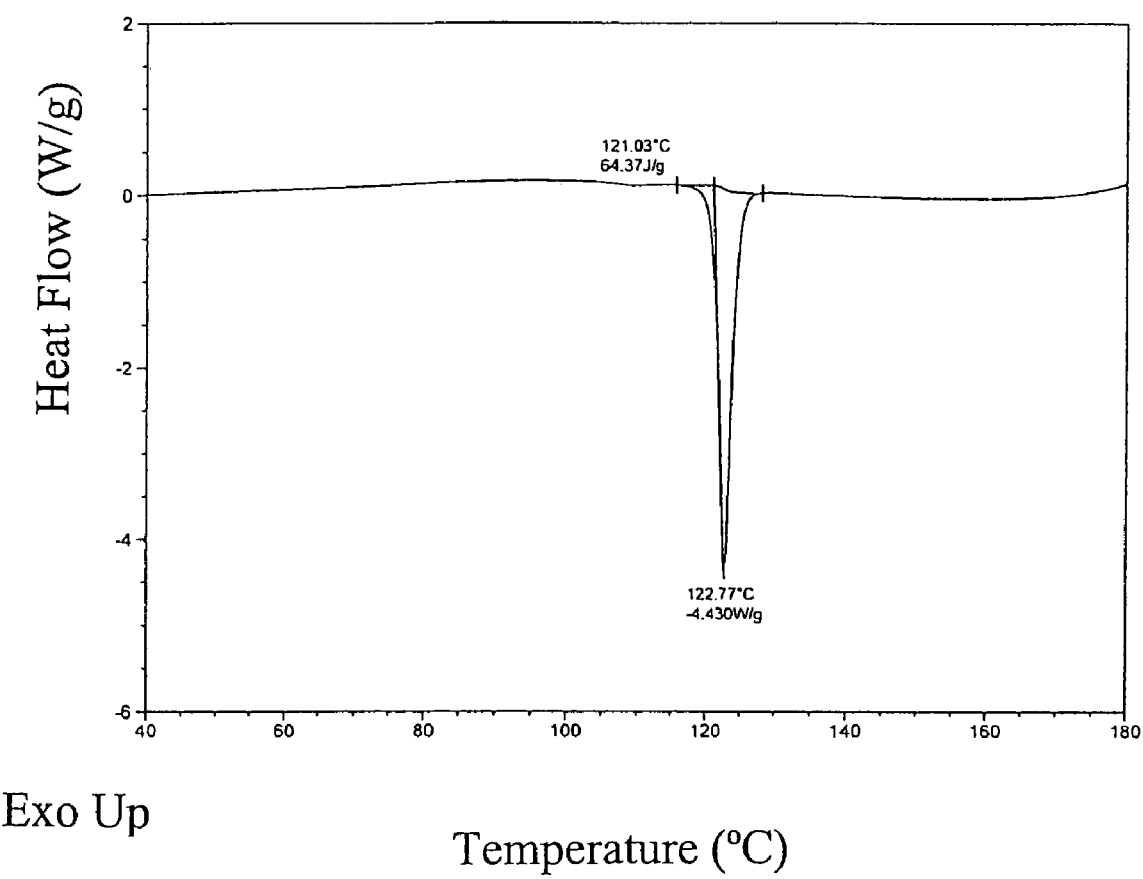
FIG. 3 is a typical DSC curve of the crystalline anhydrous free acid of Example 3.

FIG. 3 shows the differential calorimetry scan of the crystalline anhydrous free acid. The crystalline anhydrous free acid exhibited an endotherm due to melting with an onset temperature of 121.0° C., a peak temperature of 122.8° C., and an enthalpy change of 64.4 J/g.

Example 30

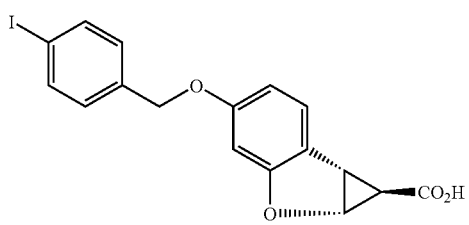

4-[(4-Iodobenzyl)oxy]-1a,6b-dihydro-1H-cyclopropa[b][1]benzofuran-1-exo-carboxylic acid See Example 28. MS: 409.2 (M+1).

Example 31

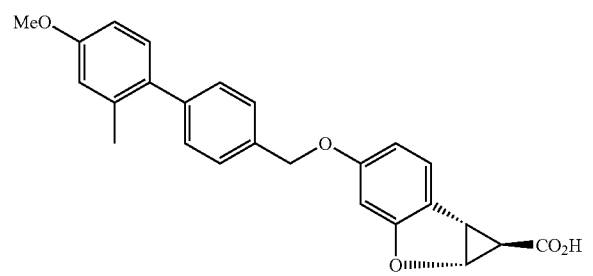

4-[(4'-Methoxy-2'-methylbiphenyl-4-yl)methoxy]-1a,6b-dihydro-1H-cyclopropa[b][1]benzofuran-1-exo-carboxylic acid See Example 29. MS: 403.1 (M+1)

Example 32

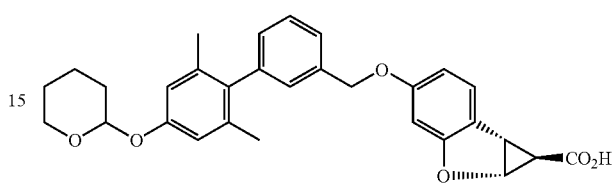

4-{[2',6'-Dimethyl-4'-(tetrahydro-2H-pyran-2-yloxy)biphenyl-3-yl]methoxy}-1a,6b-dihydro-1H-cyclopropa[b][1]benzofuran-1-exo-carboxylic acid See Example 3, step 3 and 4. The final product was purified on ChiralPak AD-H semi-preparative column, eluting with 4-7% ethanol in heptane. MS: 485.4 (M−1).

Example 33

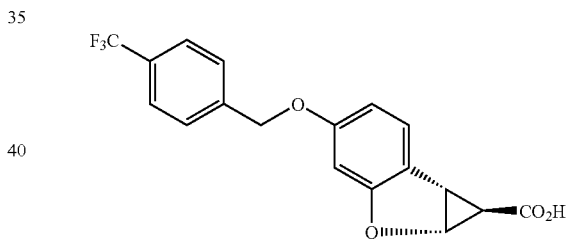

4-{[4-(trifluoromethyl)benzyl]oxy}-1a,6b-dihydro-1H-cyclopropa[b][1]benzofuran-1-exo-carboxylic acid See Example 28. MS: 351.2 (M+1).

Example 34

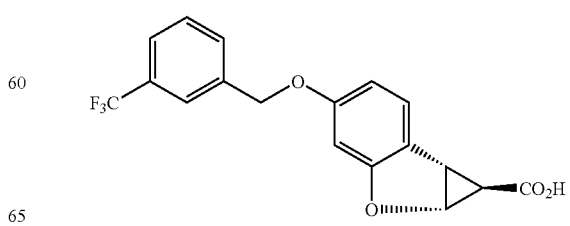

4-{[3-(Trifluoromethyl)benzyl]oxy}-1a,6b-dihydro-1H-cyclopropa[b][1]benzofuran-1-exo-carboxylic acid See Example 28. MS: 351.3 (M+1).

Example 35

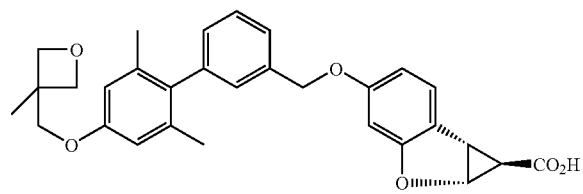

4-({2',6'-Dimethyl-4'-[(3-methyloxetan-3-yl)methoxy]biphenyl-3-yl}methoxy)-1a,6b-dihydro-1H-cyclopropa[b][1]benzofuran-1-exo-carboxylic acid See Example 3, step 3 and 4. The final product was purified on ChiralPak AD-H semi-preparative column, eluting with 4-7% ethanol in heptane. MS: 487.3 (M+1).

Example 36

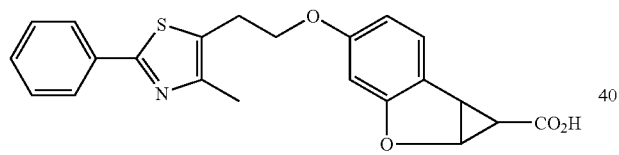

4-[2-(4-Methyl-2-phenyl-1,3-thiazol-5-yl)ethoxy]-1a,6b-dihydro-1H-cyclopropa[b][1]benzofuran-1-exo-carboxylic acid See Example 3. MS: 394.0 (M+1).

Example 37

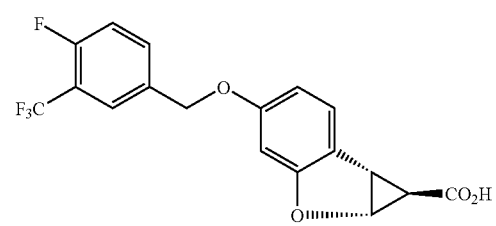

4-{[4-Fluoro-3-(trifluoromethyl)benzyl]oxy}-1a,6b-dihydro-1H-cyclopropa[b][1]benzofuran-1-exo-carboxylic acid See Example 28. MS: 369.0 (M+1).

Example 38

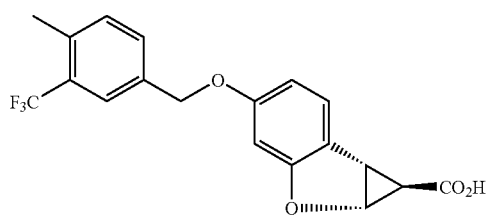

4-{[4-Methyl-3-(trifluoromethyl)benzyl]oxy}-1a,6b-dihydro-1H-cyclopropa[b][1]benzofuran-1-exo-carboxylic acid See Example 28. MS: 365.0 (M+1).

Example 39

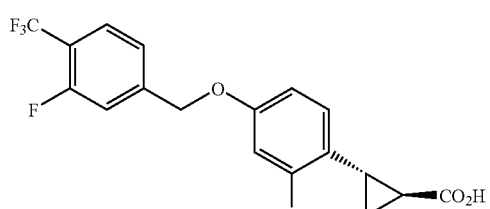

4-{[3-Fluoro-4-(trifluoromethyl)benzyl]oxy}-1a,6b-dihydro-1H-cyclopropa[b][1]benzofuran-1-exo-carboxylic acid See Example 28. MS: 369.3 (M+1).

Example 40

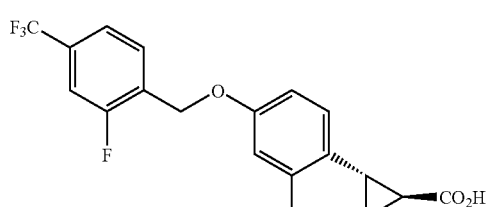

4-{[2-Fluoro-4-(trifluoromethyl)benzyl]oxy}-1a,6b-dihydro-1H-cyclopropa[b][1]benzofuran-1-exo-carboxylic acid See Example 28. MS: 369.3 (M+1).

Example 41

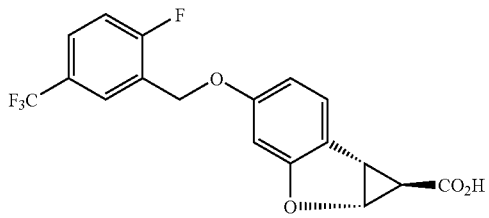

4-{[2-Fluoro-3-(trifluoromethyl)benzyl]oxy}-1a,6b-dihydro-1H-cyclopropa[b][1]benzofuran-1-exo-carboxylic acid See Example 28. MS: 369.3 (M+1).

Example 42

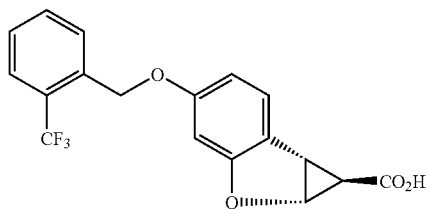

4-{[3-(trifluoromethyl)benzyl]oxy}-1a,6b-dihydro-1H-cyclopropa[b][1]benzofuran-1-exo-carboxylic acid See Example 28. MS: 351.3 (M+1).

Example 43

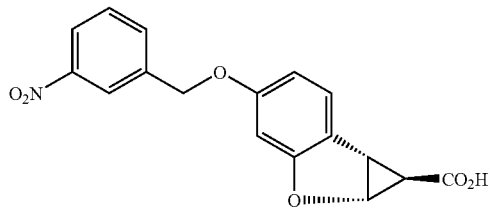

4-[(3-Nitrobenzyl)oxy]-1a,6b-dihydro-1H-cyclopropa[b][1]benzofuran-1-exo-carboxylic acid See Example 28. MS: 328.3 (M+1).

Example 44

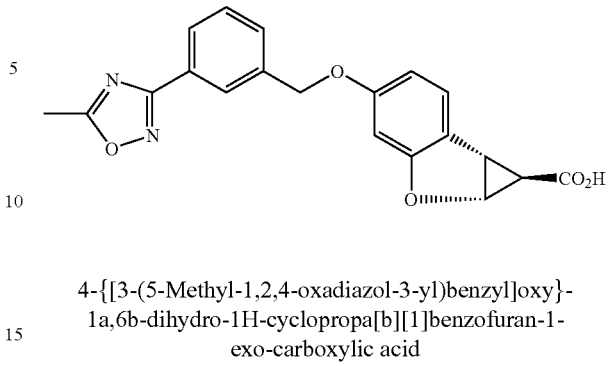

4-{[3-(5-Methyl-1,2,4-oxadiazol-3-yl)benzyl]oxy}-1a,6b-dihydro-1H-cyclopropa[b][1]benzofuran-1-exo-carboxylic acid See Example 28. MS: 365.1 (M+1).

Example 45

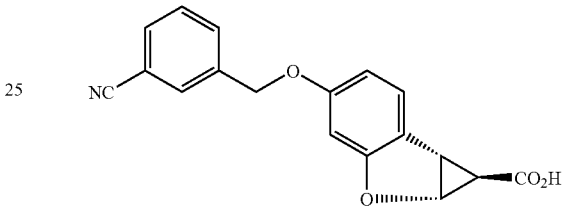

4-[(3-Cyanobenzyl)oxy]-1a,6b-dihydro-1H-cyclopropa[b][1]benzofuran-1-exo-carboxylic acid See Example 28. MS: 308.1 (M+1).

Example 46

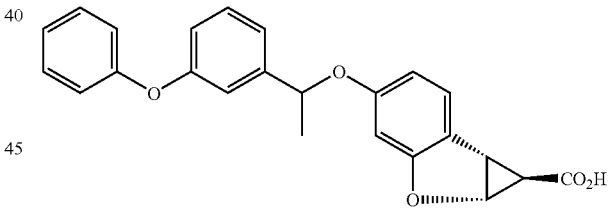

Step 1

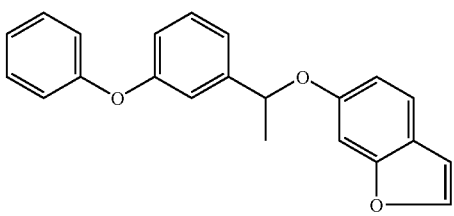

6-[1-(3-Phenoxyphenyl)ethoxy]-1-benzofuran

See Example 62, Step 2.

Step 2

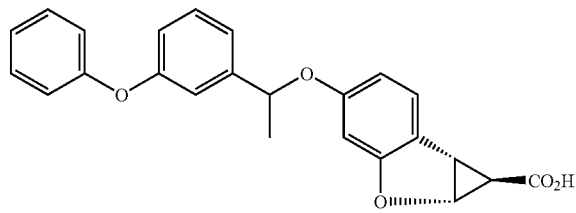

4-[1-(3-Phenoxyphenyl)ethoxy]-1a,6b-dihydro-1H-cyclopropa[b][1]benzofuran-1-exo-carboxylic acid See Example 3, step 3 and 4. MS: 389.1 (M+1).

Example 47

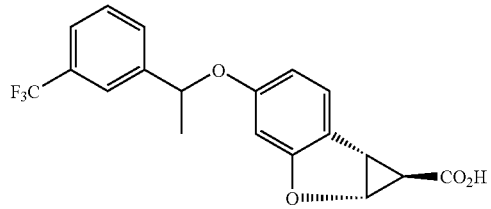

4-{1-[3-(Trifluoromethyl)phenyl]ethoxy}-1a,6b-dihydro-1H-cyclopropa[b][1]benzofuran-1-exo-carboxylic acid See Example 46. MS: 365.0

Example 48

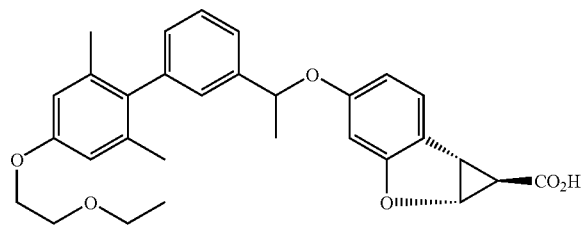

4-{1-[4'-(2-Ethoxyethoxy)-2',6'-dimethylbiphenyl-3-yl]ethoxy}-1a,6b-dihydro-1H-cyclopropa[b][1]benzofuran-1-exo-carboxylic acid See Example 46. MS: 489.1 (M+1).

Scheme 7: Indane Derivatives

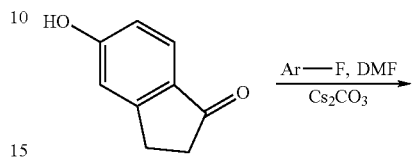

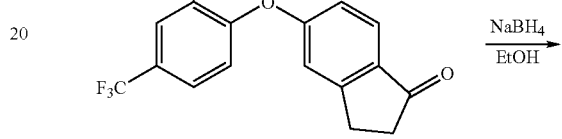

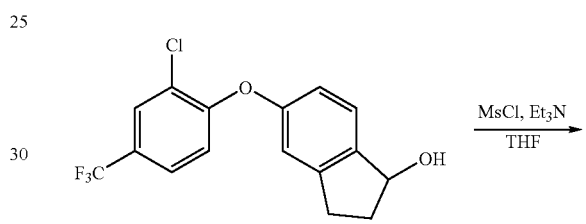

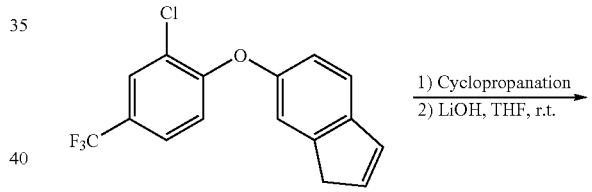

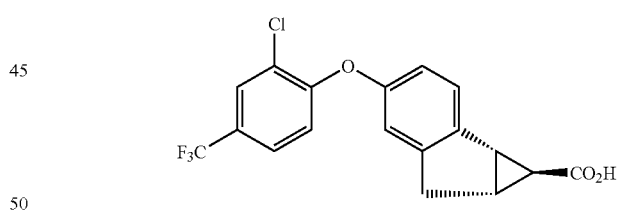

Example 49

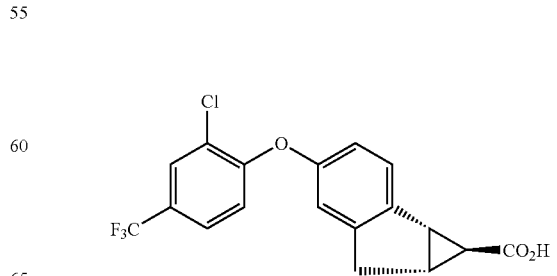

Step 1

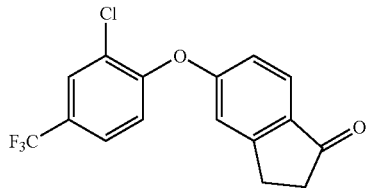

5-[2-Chloro-4-(trifluoromethyl)phenoxy]indan-1-one

See Example 1, Step 1.

Step 2

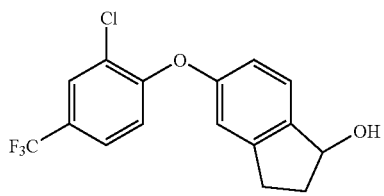

5-[2-Chloro-4-(trifluoromethyl)phenoxy]indan-1-ol

To a stirred solution of the above indanone (2.0 g, 6 mmol) was added sodium borohydride in several portions. After 30 min, the reaction was quenched carefully with hydrochlorid acid (2N). The crude product was extracted with ethyl acetate, and purified on a silica gel column, eluting with ethyl acetate (0-40%) in hexanes to yield the final product as colorless oil.

Step 3

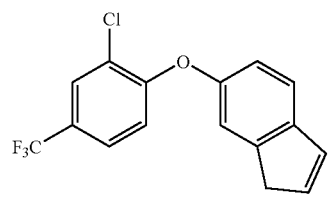

2-Chloro-4-(trifluoromethyl)phenyl 1H-inden-6-yl ether

To a stirred solution of the above indanol (1.05 g, 3.2 mmol) in dichloromethane (30 mL) at 0° C. was added methanesulphonyl choride (0.3 mL, 3.8 mmol) and triehtylamine (1.1 mL, 8.0 mmol). The reaction was warmed up to room temperature over a course of 2 h, and stirred overnight. After usual aqueous workup, the crude product was purified on a silica gel column, eluting with ethyl acetate (0-30%) in hexane. The final product was collected as slight yellowed oil.

Step 4

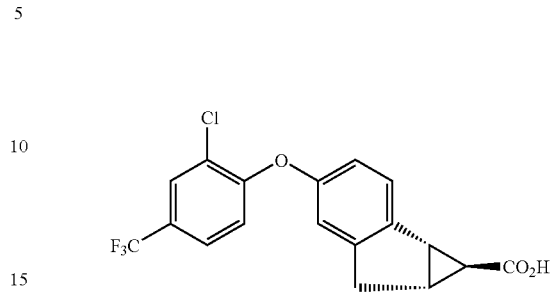

The final product was obtained from the indenyl ether from Step 3, using the method of Example 1, step 2 and step 3. MS: 367.1 (M−1).

Example 50

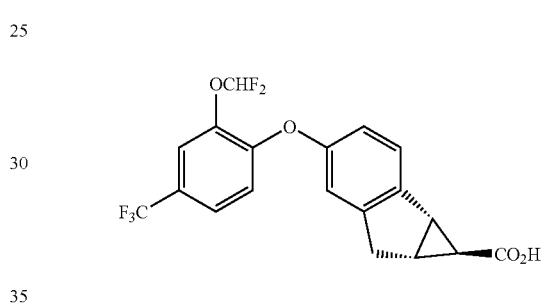

4-[2-(difluoromethoxy)-4-(trifluoromethyl)phenoxy]-1,1a,6,6a-tetrahydrocyclopropa[a]indene-1-exo-carboxylic acid See Example 3 and 49. The final product was purified on ChiralPak AD-H semi-preparative column, eluting with 4-7% ethanol in heptane. MS: 401.3 (M+1).

Example 51

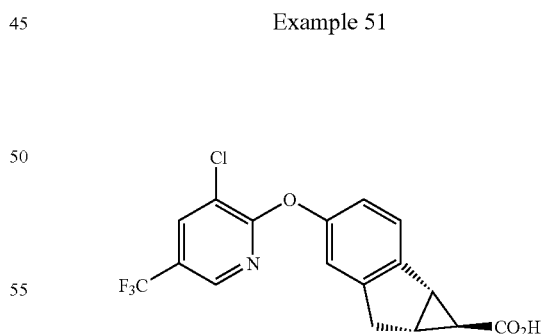

4-{[3-Chloro-5-(trifluoromethyl)pyridin-2-yl]oxy}-1a,6b-dihydro-1H-cyclopropa[b][1]benzofuran-1-exo-carboxylic acid See Example 3 and 49. The final product was purified on ChiralPak AD-H semi-preparative column, eluting with 4-7% ethanol in heptane. MS: 370.1 (M−1).

Scheme 8: Biaryl Indanones

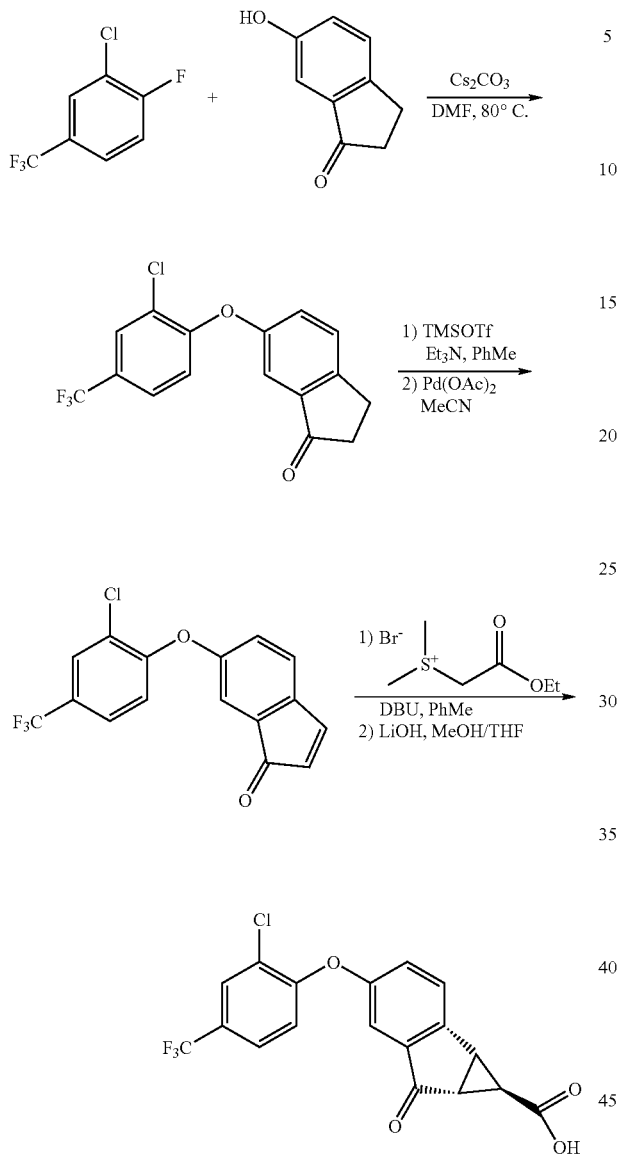

Example 52

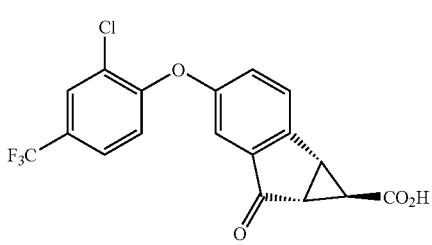

Step 1

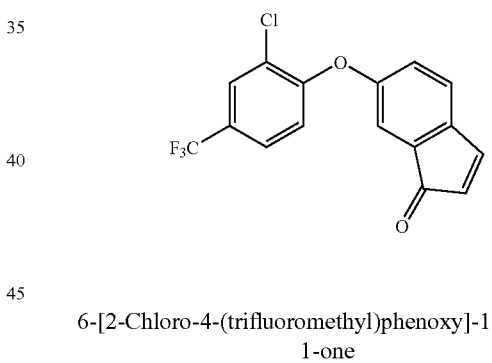

6-[2-Chloro-4-(trifluoromethyl)phenoxy]indan-1-one

To a stirred solution of 6-hydroxyindan-1-one (1.48 g, 10 mmol) in 30 ml of DMF was added 3-chloro-4-fluorobenzotrifluoride (2.46 g, 12 mmol) and cesium carbonate (8.40 g, 25 mmol). The reaction mixture was heated at 80° C. for 12 h. After cooling to room temperature, the reaction mixture was diluted with ethyl acetate, washed with water (2×) and brine, dried over sodium sulfate, filtered and concentrated. The crude product was purified by silica gel chromatography, eluting with ethyl acetate (2-40%) in hexane. The final product was collected as brownish yellow oil.

Step 2

6-[2-Chloro-4-(trifluoromethyl)phenoxy]-1H-inden-1-one

To a stirred solution of 6-[2-chloro-4-(trifluoromethyl)phenoxy]indan-1-one (200 mg, 0.612 mmol) in toluene (5.0 mL) at 0° C. under nitrogen was added triethylamine (0.104 mL, 0.734 mmol) followed by trimethylsilyl trifluoromethanesulfonate (0.140 g, 0.612 mmol). The reaction warmed to room temperature and stirred for 10 min, then was diluted with diethyl ether and saturated sodium bicarbonate. The aqueous layer was extracted with diethyl ether and the combined organic layers were washed with brine, dried with magnesium sulfate, filtered and concentrated. The resulting residue was dissolved in dichloromethane (1.0 mL) and added via canula at room temperature in the dark to a suspension of Pd(OAc)$_2$ (134 mg, 0.60 mmol) in acetonitrile (4.0 mL). The resulting reaction mixture stirred 1.25 h, then was diluted with diethyl ether, filtered through celite and concentrated to provide the final product as yellow oil which was carried forward without further purification.

Step 3

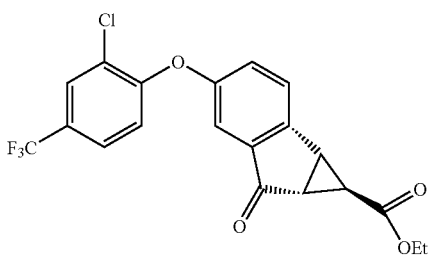

Ethyl 4-[2-chloro-4-(trifluoromethyl)phenoxy]-6-oxo-1,1a,6,6a-tetrahydrocyclopropa[a]indene-1-exo-carboxylate To a stirred suspension of ethyl (dimethylsulfuranylidene)acetate (J. Med. Chem. 1997, 40, 528, 168 mg, 0.73 mmol) in toluene (2.0 mL) was added DBU (0.111 g, 0.73 mmol) at room temperature. The mixture was stirred for 1 h, after which a solution of 6-[2-chloro-4-(trifluoromethyl)phenoxy]-1H-inden-1-one (0.188 g, 0.58 mmol) in toluene (0.5 mL) was added in the dark. The reaction mixture stirred 12 h at room temperature, then was quenched with saturated ammonium chloride and extracted with ethyl acetate. The combined organic layers were washed with brine, dried with sodium sulfate, filtered and concentrated. The resulting residue was purified on a silica gel column, eluting with ethyl acetate (4-60%) in hexane. The product was collected as clear oil.

Step 4

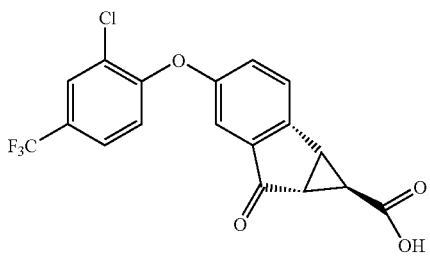

4-[2-Chloro-4-(trifluoromethyl)phenoxy]-6-oxo-1,1a,6,6a-tetrahydrocyclopropa[a]indene-1-exo-carboxylic acid See Example 1. Purification by reverse phase HPLC (0.1% TFA/H$_2$O/Acetonitrile gradient) provided product as white solid. MS: 383.0 (M+1).

Example 53

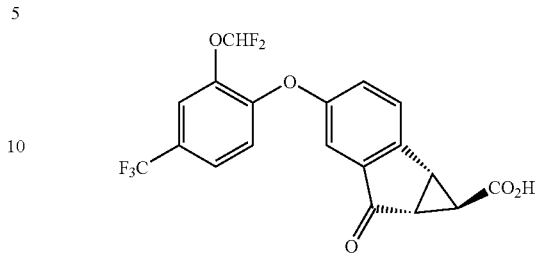

4-[2-(Difluoromethoxy)-4-(trifluoromethyl)phenoxy]-6-oxo-1,1a,6,6a-tetrahydrocyclopropa[a]indene-1-exo-carboxylic acid See Example 52. MS: 414.0 (M+1).

Example 54

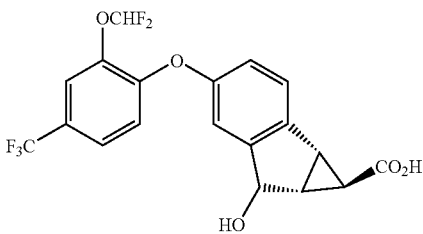

Step 1

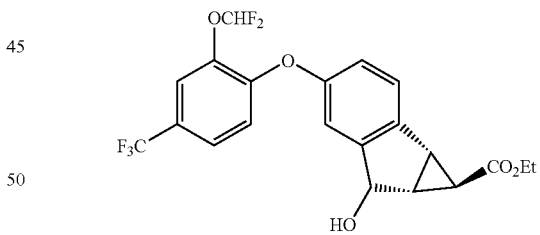

Ethyl 4-[2-(difluoromethoxy)-4-(trifluoromethyl)phenoxy]-6-hydroxy-1,1a,6,6a-tetrahydrocyclopropa[a]indene-1-exo-carboxylate To a stirred solution of corresponding keto ester (24 mg, 0.054 mmol) in THF (0.5 mL) was added lithium borohydride solution in THF (2.0 M, 0.065 mL) at 0 C. After 1 h, the reaction was quenched with saturated sodium bicarbonate and extracted with ethyl acetate. The combined organics were washed with brine, dried over sodium sulfate, filtered and concentrated. Silica gel chromatography eluting with ethyl acetate (4%-60%) in hexane provided product (4:1 mixture of diastereomers) as colorless oil.

Step 2

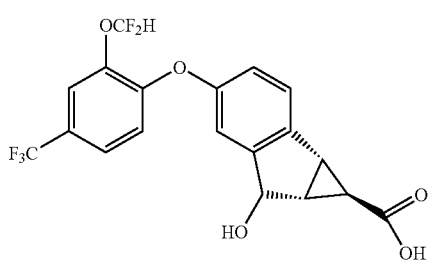

4-[2-(difluoromethoxy)-4-(trifluoromethyl)phenoxy]-6-hydroxy-1,1a,6,6a-tetrahydrocyclopropa[a]indene-1-exo-carboxylic acid See Example 1. Final product (4:1 mixture of diastereomers) was collected as white solid. MS: 416.1 (M+1).

Scheme 9: Aminoindane Derivatives

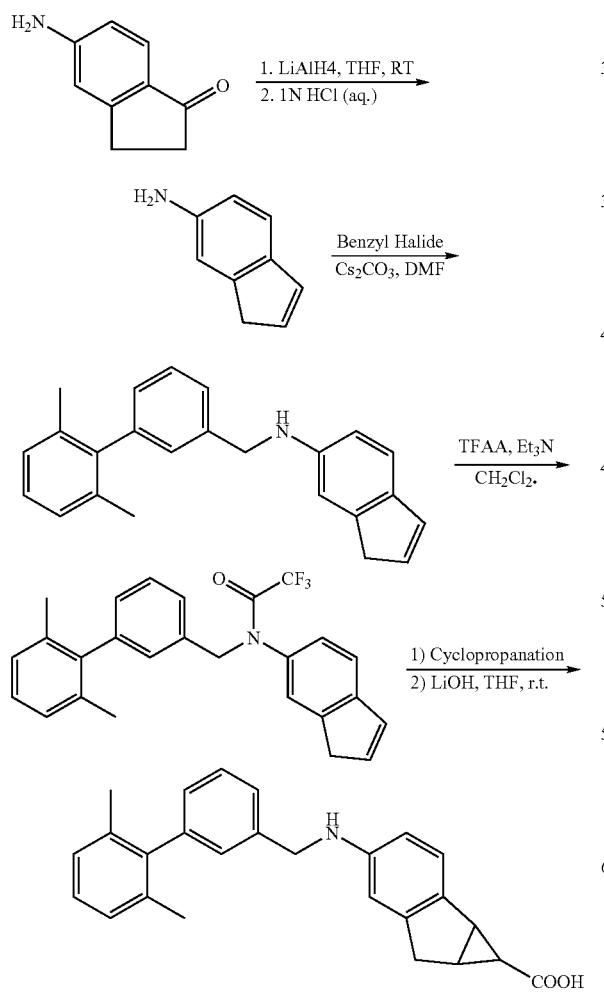

Example 55

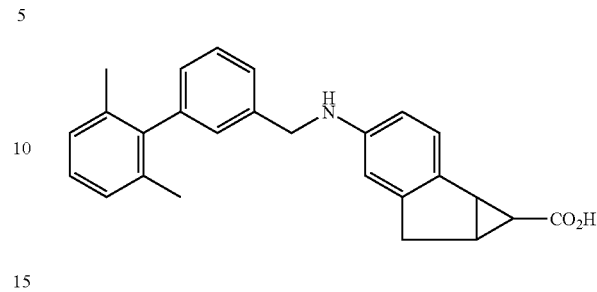

Step 1

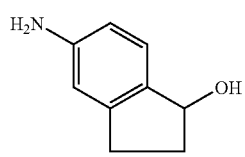

5-Aminoindan-1-ol

To a stirred solution of 5-hydroxyindane-1-one (4 g, 0.27 mol) in THF (100 mL) was added 1 M solution of lithium aluminum hydride in THF (20 ml, 0.2 mol) dropwise in about 20 min. with ice bath cooling. The mixture was then stirred at room temperature for 2-4 h. It was then quenched with 1.0 N NaOH solution until no more gas evolves, and left stir at room temperature for 30 minutes. The suspension was filtered, residue washed with ethyl acetate. The organic phase was combined, dried over magnesium sulfate, filtered and concentrated to obtain the product as an oil. The crude product was used in the next step without further purification.

Step 2

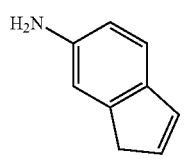

1H-inden-6-amine

To a stirred solution of 5-amino-1-hydroxyindane (4.2 g, 0.26 mol) in methanol (100 mL) was added hydrochloric acid (100 mL, 1.0 N). The mixture was stirred at 40° C. for 2 h, and then was concentrated to dryness under vacuum to the product as gray powder.

Step 3

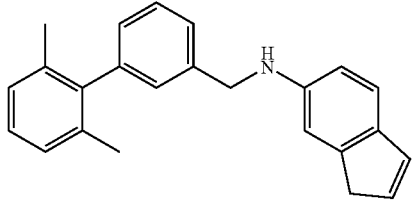

N-1H-inden-6-yl-2',6'-dimethylbiphenyl-4-amine

See Example 1, Step 1. The final product was collected as colorless oil.

Step 4

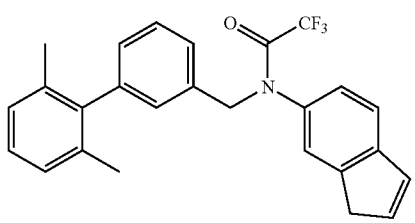

N-(2',6'-dimethylbiphenyl-4-yl)-2,2,2-trifluoro-N-1H-inden-6-ylacetamide

To a stirred solution of 4-[(2',6'-dimethylbiphenyl-3-yl) methylamino]-indene (170 mg, 0.52 mmol) in dichloromethane (4.0 ml) was added trifluoroacetic anhydride (100 mg, 5.3 mmol) in an ice bath. The mixture was stirred at 0° C. for 4 hours, concentrated to dryness and purified on a silica gel column, eluting with ethyl acetate (0-30%) in hexane. The final product was collected as colorless oil.

Step 5

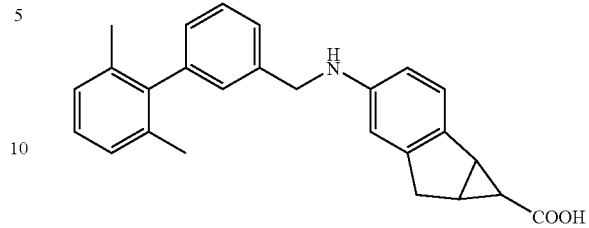

4-[(2',6'-dimethylbiphenyl-4-yl)amino]-1,1a,6,6a-tetrahydrocyclopropa[a]indene-1-exo-carboxylic acid See Example 1, Step 2 and 3. Cyclopropanation was carried out in dichloroethane at 80° C. MS: 384.2 (M+1).

Example 56

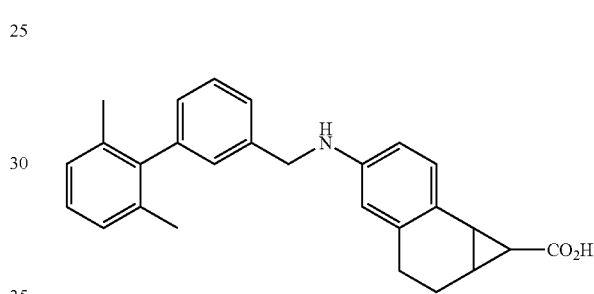

5-[(2',6'-Dimethylbiphenyl-3-yl)methoxy]-1a,2,3,7b-tetrahydro-1H-cyclopropa[a]naphthalene-1-exo-carboxylic acid See Example 55. MS: 398.2 (M+1).

Scheme 10: Benzothiophene Derivatives

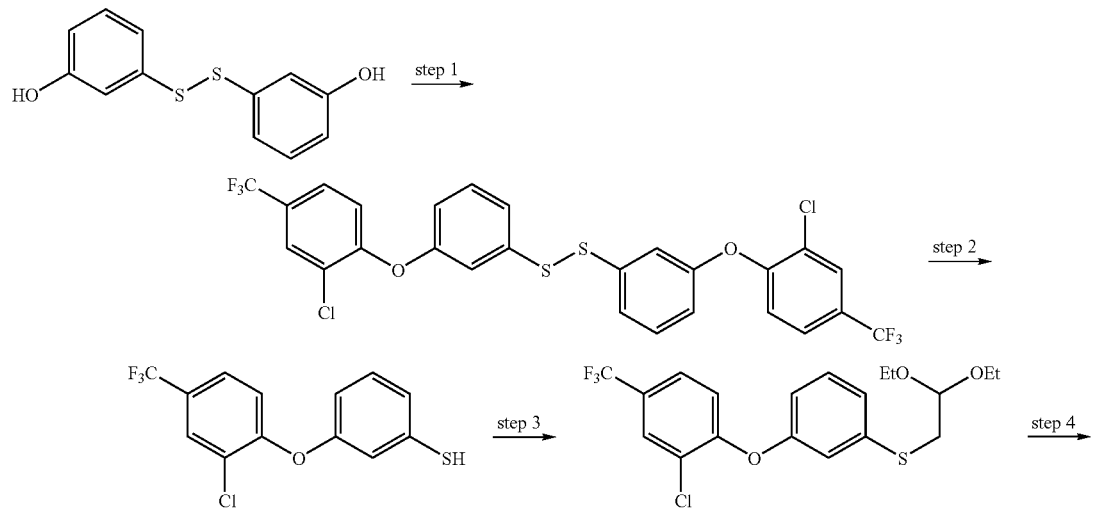

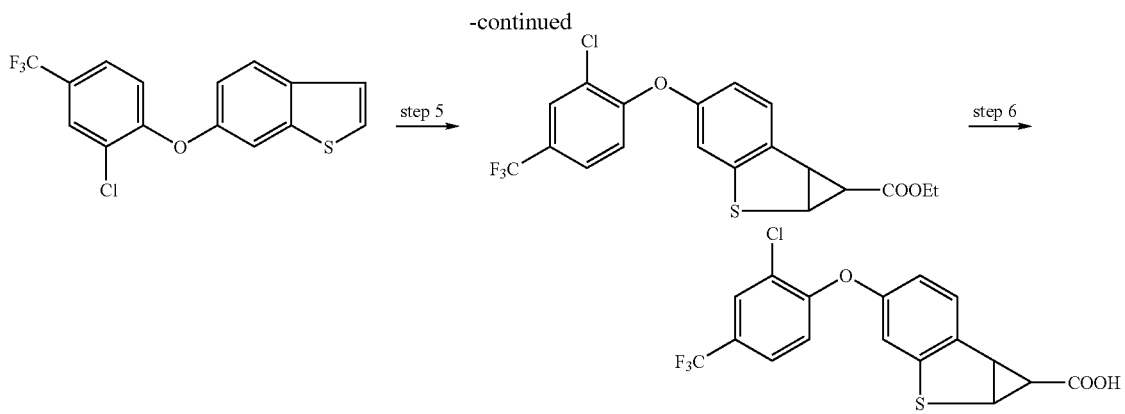

Example 57

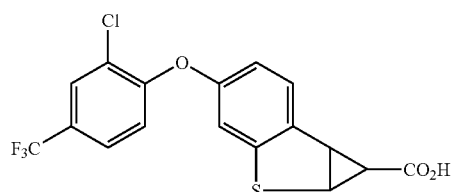

Step 1

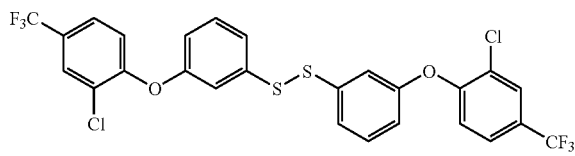

To a suspension of 3,3'-dihydroxydiphenyl disulfide (1.01 g, 4.03 mmol) and Cs₂CO₃ (3.3 g, 10 mmol) in DMF (20 mL) was added 3-chloro-4-fluorobenzotrifluoride (2 g, 10 mmol). The reaction was heated at 100° C. overnight. The mixture was then cooled and partitioned between ether (200 mL) and water (200 mL). The aqueous layer was further extracted with ether (2×100 mL). The organic layers were combined, washed with water (1×100 mL), Brine (1×100 mL), dried with anhydrous sodium sulfate, filtered and concentrated. The resulting oil was used in the next step directly.

Step 2

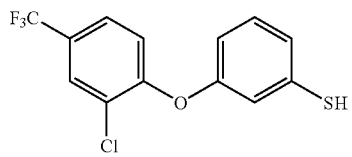

A solution of the product from Step 1 (~3.6 mmol) in THF (30 mL) was degassed by bubbling through nitrogen for 30 minutes. n-Bu₃P (896 μL, 3.6 mmol) was then added. The reaction was stirred at room temperature for 1 hour. The completed reaction was partitioned between EtOAc (200 mL) and water (150 mL). The aqueous layer was further extracted with EtOAc (2×100 mL). The organic layers were combined, washed with water (1×100 mL), Brine (1×100 mL), dried with anhydrous sodium sulfate, filtered and concentrated. The mixture was then purified by flash chromatography (0% to 50% EtOAc/hexanes) to give the desired thiol.

Step 3

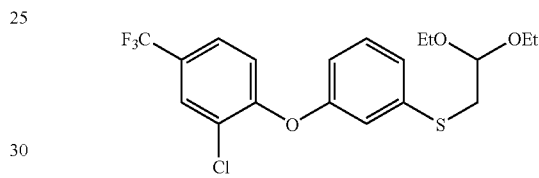

To the product from Step 2 (2.4 g, 8 mmol) in DMF (40 mL) was added NaH (60% in mineral oil, 345 mg). After being stirred for 30 minutes at room temperature, a clear solution was obtained. Bromoacetaldehyde ditheyl acetal (10 mmol, 1.55 mL) was then added to the reaction. The reaction was completed after 1 hour at room temperature. The completed reaction was partitioned between MTBE (200 mL) and water (150 mL). The aqueous layer was further extracted with MTBE (2×100 mL). The organic layers were combined, washed with water (1×100 mL), Brine (1×100 mL), dried with anhydrous sodium sulfate, filtered and concentrated. The mixture was then purified by flash chromatography (0% to 15% EtOAc/hexanes) to give the desired product.

Step 4

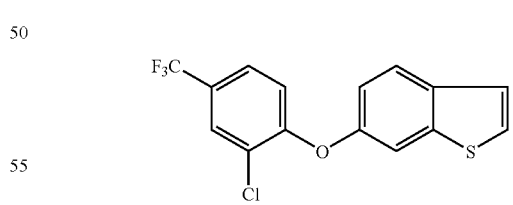

To a stirred solution of BF₃·Et₂O (3.55 mmol, 0.45 mL) in CH₂Cl₂ (40 mL) was added a solution of the product from Step 3 (1.36 g, 3.32 mmol) in CH₂Cl₂ (15 mL) slowly over 1 hour at room temperature. After addition, the reaction was stirred at room temperature overnight before quenching with saturated aqueous NaHCO₃ solution (100 mL). The organic layer was separated and the aqueous layer was further extracted with CH₂Cl₂ (2×50 mL). The organic layers were combined, washed with water (1×100 mL), Brine (1×100 mL), dried with anhydrous sodium sulfate, filtered and concentrated. The mixture was then purified by flash chromatography (0% to 15% EtOAc/hexanes) to give the desired product.

Step 5

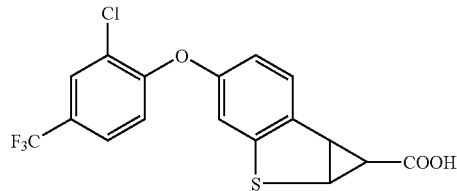

4-[2-Chloro-4-(trifluoromethyl)phenoxy]-1a,6b-dihydro-1H-cyclopropa[b][1]benzothiophene-1-exo-carboxylic acid See Example 1, Step 2 and 3. Cyclopropanation was carried out in dichloroethane at 80° C. MS: 387.0 (M+1).

Example 58

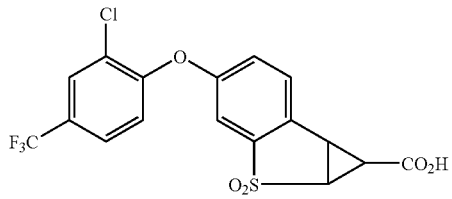

4-[2-Chloro-4-(trifluoromethyl)phenoxy]-1a,6b-dihydro-1H-cyclopropa[b][1]benzothiophene-1-exo-carboxylic acid 2,2-dioxide To a solution of Example 57 (3 mg) in $CH_2Cl_2$ (0.5 mL) was added m-CPBA (10 mg). After 1 hour at room temperature, the organic solvent was removed in vacuo and the residue was purified by reverse phase HPLC (C18, 5 micron, 20% to 80% $CH_3CN/H_2O/0.1\%$ TFA). The combined pure fractions were lyophilized overnight to give the desired product. MS: 418.7 (M+1).

Example 59

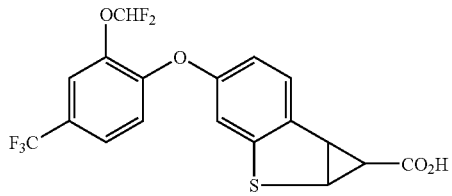

4-[2-(Difluoromethoxy)-4-(trifluoromethyl)phenoxy]-1a,6b-dihydro-1H-cyclopropa[b][1]benzothiophene-1-exo-carboxylic acid See Example 57. The final product was purified on Chiral-Pak AD-H semi-preparative column, eluting with 4-7% ethanol in heptane. MS: 418.9 (M+1).

Example 60

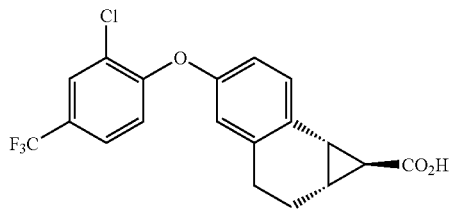

(1S,1aR,7bS)-5-[2-Chloro-4-(trifluoromethyl)phenoxy]-1a,2,3,7b-tetrahydro-1H-cyclopropa[a]naphthalene-1-carboxylic acid See Example 49. The final product was purified on Chiral-Pak AD-H semi-preparative column, eluting with 4-7% ethanol in heptane. MS: 363.3 (M+1).

Example 61

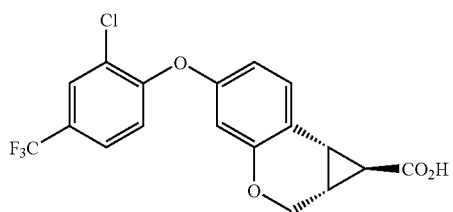

(1R,1aR,7bS)-5-[2-Chloro-4-(trifluoromethyl)phenoxy]-1,1a,2,7b-tetrahydrocyclopropa[c]chromene-1-carboxylic acid See Example 49. The final product was purified on Chiral-Pak AD-H semi-preparative column, eluting with 4-7% ethanol in heptane. MS: 385.1 (M+1).

Scheme 11: Reverse Benzyl Ethers

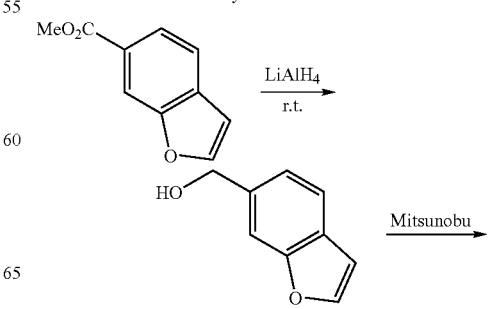

-continued

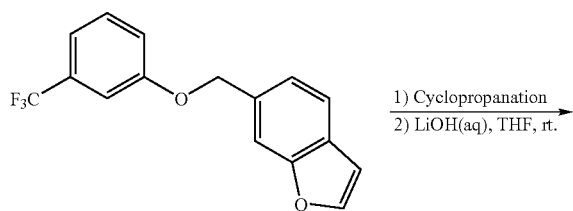

1) Cyclopropanation
2) LiOH(aq), THF, rt.

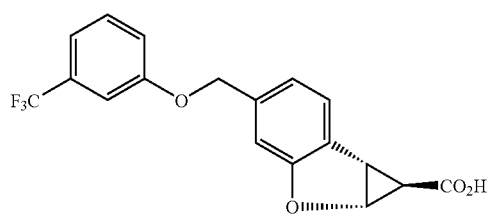

Example 62

Step 1

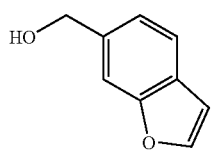

1-Benzofuran-6-ylmethanol

A solution of methyl 1-benzofuran-6-carboxylate (J. Med. Chem. 1995, 38, 3094; 142 mg, 0.8 mmol) in THF (5 ml) was added dropwise to a stirred suspension of lithium aluminum hydride (92 mg, 2.4 mmol) in THF (2 mL) at −10° C. The mixture was stirred at room temperature for 30 min, cooled to 0° C. and treated slowly with water (1 mL). The mix was brought to pH 1 with 2N HCl and extracted with ethyl acetate (3×). The combined extracts were washed with water, brine, dried (MgSO$_4$) and concentrated to give the final product.

Step 2

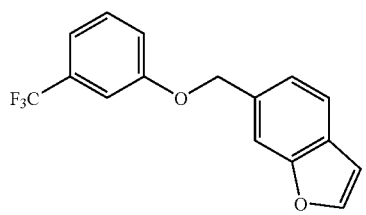

6-{[3-Trifluoromethyl)phenoxy]methyl}-1-benzofuran 1,1'-[(E)-diazene-1,2-diyldicarbonyl]diperidine, (304 mg, 1.2 mmol) was added to a stirred solution of 1-benzofuran-6-ylmethanol (119 mg, 0.8 mmol), tri-n-butylphosphine (0.3 mL, 1.2 mmol) and 3-(trifluoromethyl)phenol (0.1 mL, 0.8 mmol) in toluene (11 mL) at 0° C. The mix was stirred at room temp for 18 h, diluted with hexane (6 mL) and filtered. The filtrate was concentrated and the residue purified on a silica gel column eluting with a 1-4% EtOAc/hexane gradient to give the final product as white solid.

Step 3

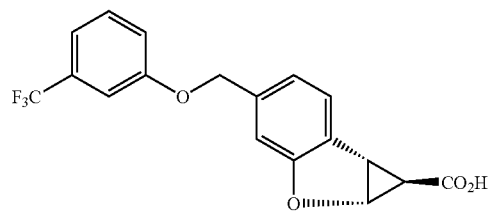

4-[(3-tert-butylphenoxy)methyl]-1a,6b-dihydro-1H-cyclopropa[b][1]benzofuran-1-exo-carboxylic acid See Example 3, step 3 and 4.

Example 63

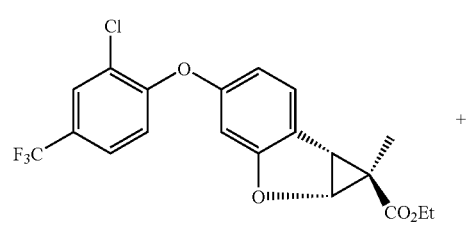

+

-continued

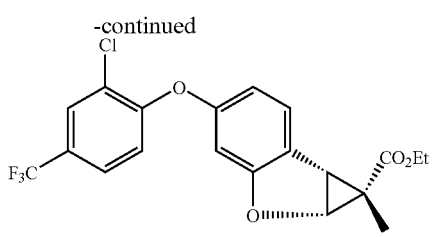

Scheme 11: Methylation of Benzofuran Derivatives

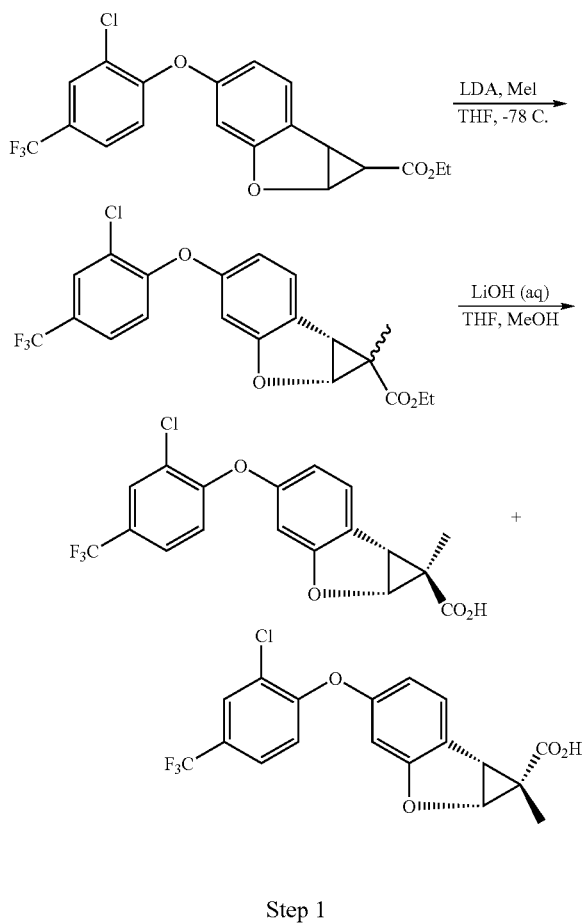

Step 1

Methylation to Yield (1R, 1aR, 6bS)-Ethyl 4-[2-chloro-4-(trifluoromethyl)phenoxy]-1a,6b-dihydro-1H-cyclopropa[b][1]benzofuran-1-methyl-1-carboxylate and (1S, 1aR,6bS)-Ethyl 4-[2-chloro-4-(trifluoromethyl)phenoxy]-1a,6b-dihydro-1H-cyclopropa[b][1]benzofuran-1-methyl-1-carboxylate.

Iodomethane (61.4 mg, 0.43 mmol) was added to a stirred solution of the cyclopropyl carboxylic ester in Scheme 11 (115 mg, 0.29 mmol) in THF (4 ml) at −78° C. under nitrogen, followed by a solution of LDA (0.23 mL, 1.5 M, 0.35 mmol) in cyclohexane. After the addition, the dark brown reaction solution was stirred at −78° C. for 2 h. The reaction was then quenched with aq. sat. ammonium chloride, and the resulting mixture was extracted with ethyl acetate. The combined organic solution was washed with brine, dried with magnesium sulfate, and concentrated. The residue was purified by preparative TLC on silica gel plates to give the 1R-(or exo-) diastereomer (in a mixture with the starting material), MS: 413.2 (M+1); and 1S-(or endo-) diastereomer (in a mixture with the starting material), MS: 413.1 (M+1).

Step 2A

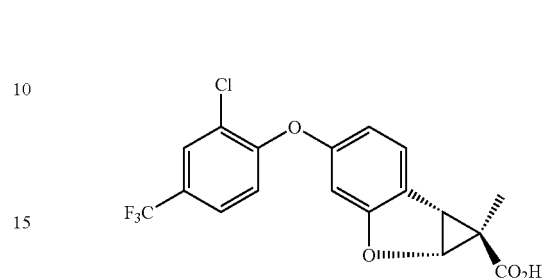

Example 63(a)

(1R, 1aR, 6bS)-4-[2-Chloro-4-(trifluoromethyl)phenoxy]-1a,6b-dihydro-1H-cyclopropa[b][1]benzofuran-1-methyl-1-carboxylic acid To a stirred solution of the above 1R ester (10 mg, 0.024 mmol) in THF-MeOH (1.5 ml-0.5 ml) was added LiOH (1 mL, 1N aq.). The reaction mixture was stirred at room temperature overnight. The reaction was quenched with formic acid (~40%). The resulting weakly acidic aqueous solution was purified on a preparative HPLC reverse phase (C-18) column, eluting with acetonitrile/water +0.1% formic acid, to give the desired product. $^1$H NMR (CDCl$_3$, δ ppm): 0.9 (s, 3H), 3.5 (d, 1H), 5.2 (d, 1H), 6.6 (m, 2H), 7.0 (d, 1H), 7.3 (m, 1H), 7.5 (m, 1H), 7.8 (s, 1H).

Step 2B

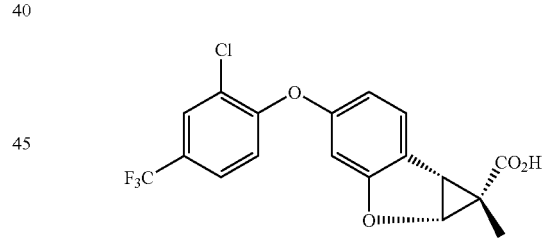

Example 63(b)

(1S, 1aR, 6bS)-4-[2-Chloro-4-(trifluoromethyl)phenoxy]-1a,6b-dihydro-1H-cyclopropa[b][1]benzofuran-1-methyl-1-carboxylic acid To a stirred solution of the above 1S ester (20 mg, 0.048 mmol) in THF-MeOH (1.5 ml-0.5 ml) was added LiOH (1 mL, 1N aq.). The reaction mixture was stirred at room temperature overnight. The reaction was quenched with formic acid (~40%). The resulting weakly acidic aqueous solution was purified on a preparative HPLC reverse phase (C-18) column, eluting with acetonitrile/water +0.1% formic acid, to give the desired product. $^1$H NMR (CDCl$_3$, δ ppm): 1.4 (s, 3H), 3.1 (m, 1H), 4.9 (m, 1H), 6.6 (m, 2H), 6.9 (d, 1H), 7.4 (d, 1H), 7.5 (m, 1H), 7.8 (m, 1H).

What is claimed is:

1. A compound of formula I, or a pharmaceutically acceptable salt thereof:

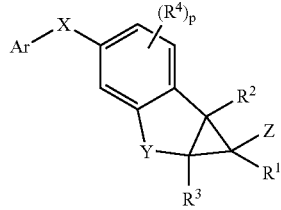

wherein Ar is selected from the group consisting of phenyl, naphthyl, a 5-6 membered monocyclic heteroaromatic group having 1-3 heteroatoms independently selected from N, O, and S, and a benzoheteroaromatic group comprising a phenyl ring fused to a 5-6 membered heteroaromatic ring having 1-3 heteroatoms independently selected from N, O and S, wherein Ar is optionally substituted with 1-2 aromatic groups independently selected from phenyl, phenoxy, benzyl, and a 5-6 membered heteroaromatic ring having 1-3 heteroatoms independently selected from N, O and S and is optionally substituted with 1-5 substituents independently selected from halogen, —CN, —NO$_2$, —OH, —C(=O)H, —C(=O)OH, C$_{1-6}$alkyl, —C$_{3-6}$cycloalkyl, —OC$_{1-6}$alkyl, —SC$_{1-6}$alkyl, —C(=O)C$_{1-6}$alkyl, —OC(=O)C$_{1-6}$alkyl, —C(=O)OC$_{1-6}$alkyl, —S(O)$_2$C$_{1-6}$alkyl, —NR$^{13}$R$^{14}$, —C(=O)N(R$^{13}$)(R$^{14}$), —S(O)$_2$NR$^{13}$R$^{14}$, and —OC$_{3-6}$cycloalkyl, wherein (a) C$_{1-6}$alkyl in all instances is optionally substituted with 1-5 halogens and optionally 1 group selected from —OH and —OC$_{1-4}$alkyl optionally substituted with 1-5 halogens, (b) —C$_{3-6}$cycloalkyl in all instances is optionally substituted with 1-2 substituents independently selected from halogen and CH$_3$, and (c) the aromatic substituent groups phenyl, phenoxy, benzyl, and the 5-6 membered heteroaromatic ring having 1-3 heteroatoms independently selected from N, O and S are optionally substituted with 1-5 groups independently selected from halogen, —CN, —NO$_2$, —OH, —C(=O)H, —C(=O)OH, C$_{1-6}$alkyl, —OC$_{1-6}$alkyl, —SC$_{1-6}$alkyl, —C(=O)C$_{1-6}$alkyl, —OC(=O)C$_{1-6}$alkyl, —C(=O)OC$_{1-6}$alkyl, —S(O)$_2$C$_{1-6}$alkyl, NR$^{13}$R$^{14}$, —C(=O)N(R$^{13}$)(R$^{14}$), —S(O)$_2$NR$^{13}$R$^{14}$, and —O(CH$_2$)q(4-6 membered heterocycle having 1-2 heteroatoms independently selected from O, S and N), wherein C$_{1-6}$alkyl in all instances is optionally substituted with 1-5 halogens and optionally 1 group selected from —OH and —OC$_{1-4}$alkyl optionally substituted with 1-5 halogens, and the 4-6 membered heterocycle having 1-2 heteroatoms independently selected from O, S and N is optionally substituted with 1-2 groups independently selected from halogen, CH$_3$, and CF$_3$;

X is selected from the group consisting of —O—, —S—, —S(O)—, —S(O)$_2$—, —NR$^5$—, —OCR$^{10}$R$^{11}$—, —SCR$^{10}$R$^{11}$—, —NR$^5$CR$^{10}$R$^{11}$—, —CR$^{10}$R$^{11}$O—, —CR$^{10}$R$^{11}$S—, —CR$^{10}$R$^{11}$NR$^5$—, and —CR$^6$R$^7$CR$^8$R$^9$O—;

Y is selected from the group consisting of —O—, —S—, —S(O)—, —S(O)$_2$—, —NR$^5$—, —C(=O)—, —CR$^6$R$^7$—, —OCR$^6$R$^7$—, —SCR$^6$R$^7$—, and —CR$^6$R$^7$CR$^8$R$^9$—;

Z is selected from the group consisting of —C(=O)OR$^{12}$, —C(=O)NR$^{13}$R$^{14}$, and 5-tetrazolyl;

R$^1$, R$^2$, and R$^3$ are each independently selected from the group consisting of H, halogen, C$_{1-3}$alkyl, and —OC$_{1-3}$alkyl, wherein C$_{1-3}$alkyl, and —OC$_{1-3}$alkyl are each optionally substituted with 1-3 halogens;

R$^4$ is selected from the group consisting of halogen, —CN, —NO$_2$, —OH, —C(=O)H, —C(=O)OH, C$_{1-6}$alkyl, —OC$_{1-6}$alkyl, —SC$_{1-6}$alkyl, —C(=O)C$_{1-6}$alkyl, —OC(=O)C$_{1-6}$alkyl, —C(=O)OC$_{1-6}$alkyl, —S(O)$_2$C$_{1-6}$alkyl, —NR$^{13}$R$^{14}$, —C(=O)N(R$^{13}$)(R$^{14}$), and —S(O)$_2$NR$^{13}$R$^{14}$, wherein C$_{1-6}$alkyl in all instances is optionally substituted with 1-5 halogens;

R$^5$, R$^{13}$ and R$^{14}$ are each independently selected from the group consisting of H, C$_{1-5}$alkyl, —C(=O)C$_{1-5}$alkyl, and —S(O)$_2$C$_{1-5}$alkyl, wherein C$_{1-5}$alkyl in all instances is optionally substituted with 1-5 halogens;

R$^6$, R$^7$, R$^8$, R$^9$, R$^{10}$, and R$^{11}$ are each independently selected from the group consisting of H, halogen, —OH, and C$_{1-3}$alkyl which is optionally substituted with 1-5 halogens;

R$^{12}$ is selected from the group consisting of H and C$_{1-7}$alkyl which is optionally substituted with 1-5 halogens;

p is an integer from 0-3; and q is 0 or 1.

2. The compound of claim 1, or a pharmaceutically acceptable salt thereof, wherein Ar is selected from the group consisting of phenyl, naphthyl, and a 5-6 membered monocyclic heteroaromatic ring having 1-3 heteroatoms independently selected from N, O, and S, wherein Ar is optionally substituted with one aromatic group selected from phenyl, phenoxy, and a 5-6 membered heteroaromatic ring having 1-3 heteroatoms independently selected from N, O and S and is optionally substituted with 1-3 substituents independently selected from halogen, —CN, —NO$_2$, —OH, —C(=O)H, —C(=O)OH, C$_{1-5}$alkyl, —C$_{3-6}$cycloalkyl, —OC$_{1-3}$alkyl, —SC$_{1-3}$alkyl, —C(=O)C$_{1-3}$alkyl, —OC(=O)C$_{1-3}$alkyl, —C(=O)OC$_{1-3}$alkyl, —S(O)$_2$C$_{1-3}$alkyl, —NR$^{13}$R$^{14}$, —C(=O)N(R$^{13}$)(R$^{14}$), —S(O)$_2$NR$^{13}$R$^{14}$, and —OC$_{3-6}$cycloalkyl, wherein (a) C$_{1-3}$alkyl in all instances is optionally substituted with 1-5 halogens and optionally 1 group selected from —OH and —OC$_{1-3}$ alkyl optionally substituted with 1-5 halogens, (b) C$_{1-5}$alkyl is optionally substituted with 1-5 halogens, (c) —C$_{3-6}$cycloalkyl in all instances is optionally substituted with 1-2 substituents independently selected from halogen and CH$_3$, and (d) the aromatic substituent group selected from phenyl, phenoxy, and a 5-6 membered heteroaromatic ring having 1-3 heteroatoms independently selected from N, O and S is optionally substituted with 1-3 groups independently selected from halogen, —CN, —NO$_2$, —OH, —C(=O)H, —C(=O)OH, C$_{1-5}$alkyl, —OC$_{1-3}$alkyl, —SC$_{1-3}$alkyl, —C(=O)C$_{1-3}$alkyl, —OC(=O)C$_{1-3}$alkyl, —C(=O)OC$_{1-3}$alkyl, —S(O)$_2$C$_{1-3}$alkyl, NR$^{13}$R$^{14}$, —C(=O)N(R$^{13}$)(R$^{14}$), —S(O)$_2$NR$^{13}$R$^{14}$, and —O(CH$_2$)q(4-6 membered heterocycle having 1-2 heteroatoms independently selected from O, S and N), wherein C$_{1-3}$alkyl in all instances is optionally substituted with 1-5 halogens and optionally 1 group selected from —OH and —OC$_{1-3}$alkyl optionally substituted with 1-5 halogens, C$_{1-5}$alkyl is optionally substituted with 1-5 halogens, and the 4-6 membered heterocycle having 1-2 heteroatoms independently selected from O, S and N is optionally substituted with 1-2 groups independently selected from halogen, CH$_3$, and CF$_3$.

3. The compound of claim 1, or a pharmaceutically acceptable salt thereof, wherein Ar is selected from the group consisting of phenyl, naphthyl, quinolyl, pyridyl, and thiazolyl, wherein Ar is optionally substituted with one aromatic group selected from phenyl, phenoxy, and oxadiazolyl, and is optionally substituted with 1-3 groups independently selected from halogen, —CN, —NO$_2$, C$_{1-4}$alkyl, —OC$_{1-2}$alkyl, and —OC$_{3-6}$cycloalkyl, wherein C$_{1-4}$alkyl and —OC$_{1-2}$ alkyl are optionally substituted with 1-5 halogens, and the substituents phenyl, phenoxy, and oxadiazolyl are optionally substituted with 1-3 groups independently selected from halogen, —CN, —NO$_2$, —OH, —C(=O)OH, C$_{1-4}$alkyl, —OC$_{1-4}$alkyl, and —O(CH$_2$)q(4-6 membered cyclic ether), wherein C1-4alkyl in all instances is optionally substituted with 1-5 halogens and is optionally substituted with 1 group selected from —OH and —OC$_{1-3}$alkyl optionally substituted with 1-5 halogens, and the 4-6 membered cyclic ether is optionally substituted with 1-2 groups independently selected from halogen, CH$_3$, and CF$_3$.

4. The compound of claim 1, or a pharmaceutically acceptable salt thereof, wherein
- Z is selected from the group consisting of —C(=O)OR$^{12}$, —C(=O)NR$^{13}$R$^{14}$, and 5-tetrazolyl;
- R$^1$, R$^2$, and R$^3$ are each independently selected from the group consisting of H, F, Cl, C$_{1-3}$alkyl, and CF$_3$;
- R$^4$ is selected from the group consisting of halogen, —CN, —NO$_2$, —OH, —C(=O)H, —C(=O)OH, C$_{1-4}$alkyl, —OC$_{1-4}$alkyl, —C(=O)C$_{1-4}$alkyl, and —NR$^{13}$R$^{14}$, wherein C$_{1-4}$alkyl in all instances is optionally substituted with 1-5 halogens;
- R$^5$ is selected from the group consisting of H, C$_{1-3}$alkyl, and —C(=O)C$_{1-3}$alkyl, wherein C$_{1-3}$alkyl and —C(=O)C$_{1-3}$alkyl are optionally substituted with 1-5 F;
- R$^6$, R$^8$, and R$^{10}$ are each independently selected from the group consisting of H, —OH, and CH$_3$;
- R$^7$, R$^9$, and R$^{11}$ are each independently selected from the group consisting of H and CH$_3$;
- R$^{13}$ and R$^{14}$ are each independently selected from the group consisting of H, C$_{1-5}$alkyl, and —S(O)$_2$C$_{1-5}$alkyl;
- p is 0 or 1; and
- q is 0 or 1.

5. The compound of claim 3, or a pharmaceutically acceptable salt thereof,
wherein X is selected from the group consisting of —O—, —S—, —S(O)—, —S(O)$_2$—, —CHR$^{11}$O—, —CH$_2$NH—, —OCH$_2$—, and —CH$_2$CH$_2$O—;
- Y is selected from the group consisting of —S—, —S(O)—, —S(O)$_2$—, —O—, —OCH$_2$—, —C(=O)—, —CHR$^6$—, —NR$^5$—, and —CH$_2$CH$_2$—;
- Z is selected from the group consisting of —C(=O)OR$^{12}$, —C(=O)NR$^{13}$R$^{14}$, and 5-tetrazolyl;
- R$^1$, R$^2$, and R$^3$ are each independently selected from the group consisting of H, CH$_3$, and CF$_3$;
- R$^4$ is selected from the group consisting of halogen, CH$_3$, and CF$_3$;
- R$^5$ is selected from the group consisting of H and CH$_3$;
- R$^6$ is selected from the group consisting of H and —OH;
- R$^{11}$ is selected from H and CH$_3$;
- R$^{12}$ is selected from the group consisting of H and C$_{1-5}$alkyl which is optionally substituted with 1-5 halogens;
- R$^{13}$ is selected from the group consisting of H, C$_{1-3}$alkyl, and —S(O)$_2$C$_{1-3}$alkyl;
- R$^{14}$ is H;
- p is 0 or 1; and
- q is 0 or 1.

6. The compound of claim 5, or a pharmaceutically acceptable salt thereof, wherein
Ar is selected from the group consisting of phenyl, naphthyl, pyridyl, and thiazolyl, wherein Ar is optionally substituted with one aromatic group selected from phenyl, phenoxy, and oxadiazolyl, and is optionally substituted with 1-3 groups independently selected from halogen, —CN, —NO$_2$, C$_{1-4}$alkyl, —OC$_{1-2}$alkyl, and —OC$_{3-6}$cycloalkyl, wherein C$_{1-4}$alkyl and —OC$_{1-2}$ alkyl are optionally substituted with 1-5 halogens, and the substituents phenyl, phenoxy, and oxadiazolyl are optionally substituted with 1-3 groups independently selected from halogen, —CN, —NO$_2$, —OH, C$_{1-3}$alkyl, —OC$_{1-3}$alkyl, and —O(CH$_2$)q(4-6 membered cyclic ether), wherein C$_{1-3}$alkyl is optionally substituted with 1-3 halogens, and —OC$_{1-3}$alkyl is optionally substituted with 1-3 halogens and is optionally substituted with 1 group selected from —OH and —OC$_{1-3}$alkyl optionally substituted with 1-3 halogens, and the 4-6 membered cyclic ether is optionally substituted with 1-2 groups independently selected from halogen, CH$_3$ and CF$_3$;
- X is selected from the group consisting of —O—, —CHR$^{11}$O—, —CH$_2$NH—, —OCH$_2$—, and —CH$_2$CH$_2$)—;
- Y is selected from the group consisting of —S—, —S(O)$_2$—, —O—, —OCH$_2$—, —C(=O)—, —CHR$^6$—, and —CH$_2$CH$_2$—;
- Z is selected from the group consisting of —C(=O)OR$^{12}$, —C(=O)NR$^{13}$R$^{14}$, and 5-tetrazolyl;
- R$^1$, R$^2$, and R$^3$ are each independently selected from the group consisting of H and CH$_3$;
- R$^6$ is selected from the group consisting of H and —OH;
- R$^{11}$ is selected from H and CH$_3$;
- R$^{12}$ is H;
- R$^{13}$ is selected from the group consisting of H, C$_{1-3}$alkyl, and —S(O)$_2$C$_{1-3}$alkyl;
- R$^{14}$ is H;
- p is 0; and
- q is 0 or 1.

7. The compound of claim 1, or a pharmaceutically acceptable salt thereof, wherein p is 0; and Ar is substituted with 1-3 substituent groups.

8. The compound of claim 7, or a pharmaceutically acceptable salt thereof, wherein
Ar is selected from the group consisting of
(a) phenyl, wherein phenyl is optionally substituted with 1-3 groups independently selected from halogen, —CN, —NO$_2$, C$_{1-4}$alkyl, —OC$_{1-2}$alkyl, and —OC$_{3-6}$cycloalkyl, wherein C$_{1-4}$alkyl and —OC$_{1-2}$alkyl are optionally substituted with 1-3 halogens, and wherein phenyl is optionally substituted with one group selected from (i) phenyl, which is optionally substituted with 1-3 substituents independently selected from halogen, —CN, —NO$_2$, CH$_3$, —OCH$_3$, CF$_3$, —OCF$_3$, —OCHF$_2$, —OCH$_2$CH$_2$OC$_{1-2}$alkyl, and —O(CH$_2$)q(4-6 membered cyclic ether selected from oxetane and tetrahydropyran), wherein the 4-6 membered cyclic ether is optionally substituted with 1 group selected from halogen, CH$_3$, and CF$_3$; (ii) phenoxy, which is optionally substituted with 1-3 groups independently selected from CH$_3$, CF$_3$, and halogen; and (iii) 1,2,4-oxadiazol-3-yl, which is optionally substituted with 1-2 CH$_3$ groups;
(b) naphthyl, which is optionally substituted with 1-2 groups independently selected from CH$_3$, CF$_3$, halogen, and —CN;
(c) pyridyl, which is optionally substituted with 1-2 groups independently selected from CH$_3$, CF$_3$, and halogen; and (d) 1,3-thiazol-5-yl, which is optionally substituted with 1-2 substituents independently selected from phenyl, $CH_3$, and halogen;

X is selected from the group consisting of —O—, —$CH_2$O—, —CH($CH_3$)O—, —$CH_2CH_2$O—, —$CH_2$NH—, and —O$CH_2$—;

Y is selected from the group consisting of —S—, —S(O)$_2$—, —O—, —O$CH_2$—, —C(=O)—, —CH(OH)—, —$CH_2$—, and —$CH_2CH_2$—;

Z is selected from the group consisting of —C(=O)OH, —C(=O)NR$^{13}$R$^{14}$, and 5-tetrazolyl;

R$^1$, R$^2$, and R$^3$ are each independently selected from the group consisting of H and $CH_3$;

R$^{13}$ is selected from the group consisting of H, $C_{1-3}$alkyl, and —S(O)$_2$C$_{1-3}$alkyl;

R$^{14}$ is H;

p is 0; and q is 0 or 1.

9. The compound of claim 8, or a pharmaceutically acceptable salt thereof, wherein Ar is phenyl, wherein phenyl is optionally substituted with 1-3 groups independently selected from halogen, —CN, —NO$_2$, $C_{1-4}$alkyl, $CF_3$, —OCF$_3$, —OCHF$_2$, —OC$_{1-2}$alkyl, and —O-cyclopropyl, and is optionally substituted with one group selected from (i) phenyl, which is optionally substituted with 1-3 substituents independently selected from halogen, —CN, —NO$_2$, $CH_3$, —OCH$_3$, CF$_3$, —OCF$_3$, —OCH$_2$CH$_2$OC$_{1-2}$alkyl, and —O(CH$_2$)q(4-6 membered cyclic ether selected from oxetane and tetrahydropyran), wherein the 4-6 membered cyclic ether is optionally substituted with 1 group selected from CH$_3$, and CF$_3$; (ii) phenoxy, which is optionally substituted with 1-3 groups independently selected from CH$_3$, CF$_3$, and halogen; and (iii) 1,2,4-oxadiazol-3-yl, which is optionally substituted with 1-2 CH$_3$ groups;

X is selected from the group consisting of —O— and —CH$_2$O—;

Y is O;

Z is selected from the group consisting of —C(=O)OH and —C(=O)NR$^{13}$R$^{14}$;

R$^{13}$ is, selected from the group consisting of H, CH$_3$, and —S(O)$_2$CH$_3$; and R$^{14}$ is H.

10. The compound of claim 8, or a pharmaceutically acceptable salt thereof, selected from the group consisting of compounds having the following structures:

Ex. 1

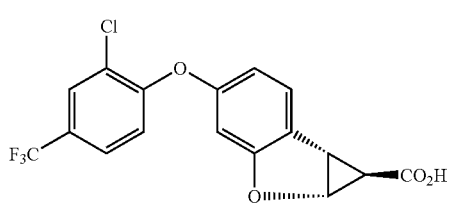

Ex. 2

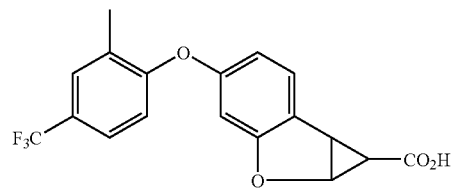

Ex. 3

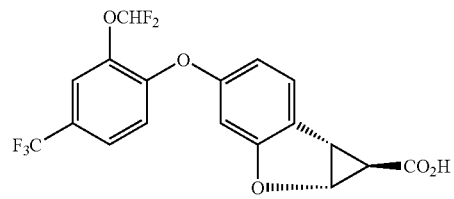

Ex. 4

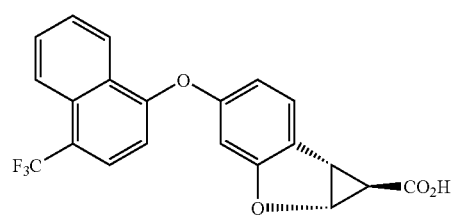

Ex. 5

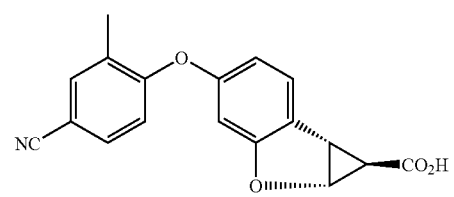

Ex. 6

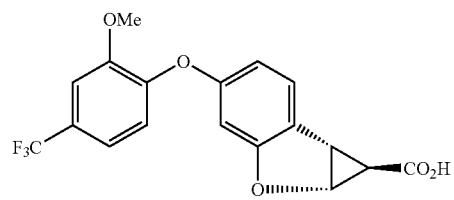

Ex. 7

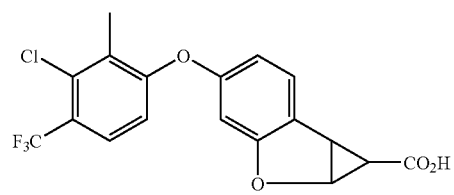

Ex. 8

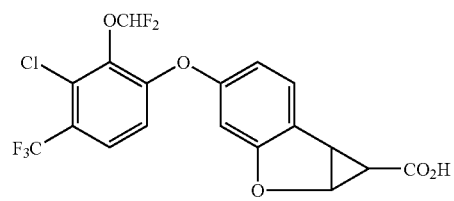

Ex. 9
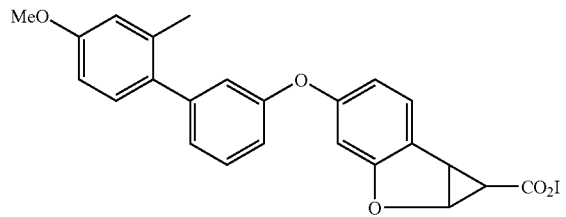
Ex. 10
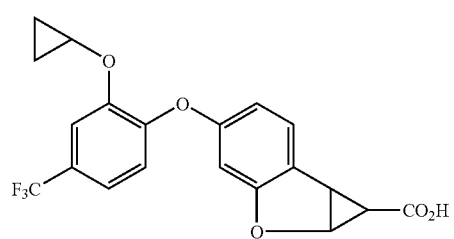
Ex. 11
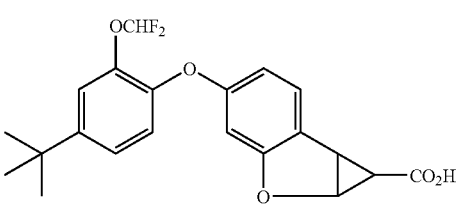
Ex. 12
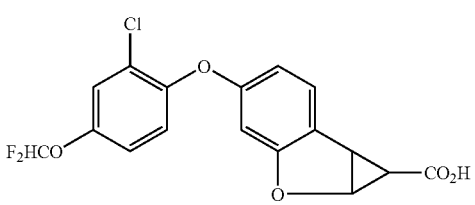
Ex. 13
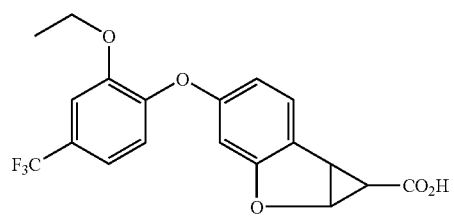
Ex. 14
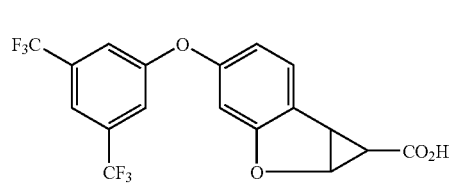
Ex. 15
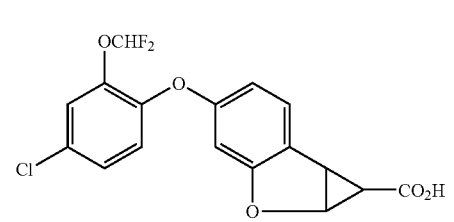
Ex. 16
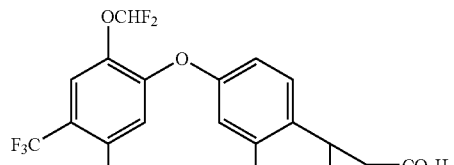
Ex. 17
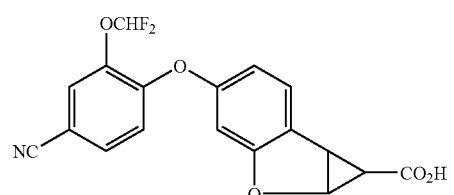
Ex. 18
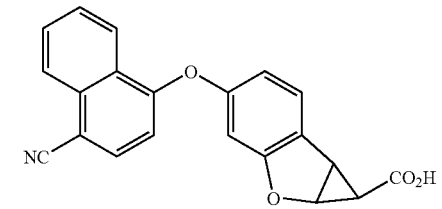
Ex. 19
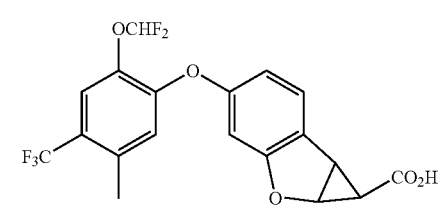
Ex. 20
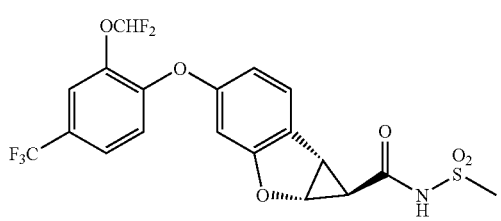
Ex. 21
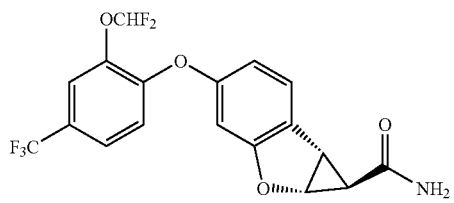
Ex. 22
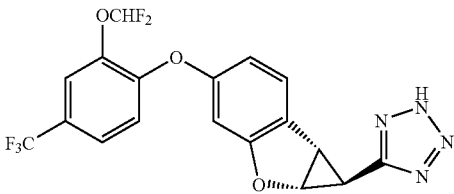

-continued
Ex. 23
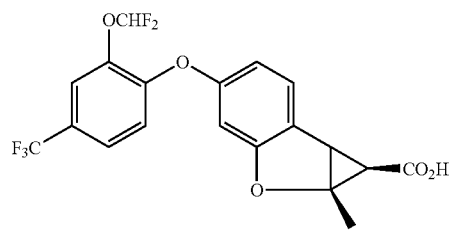
Ex. 24
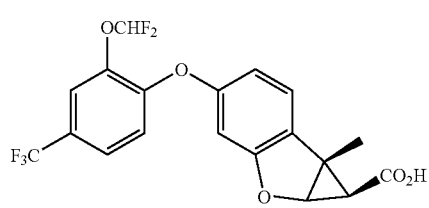
Ex. 25
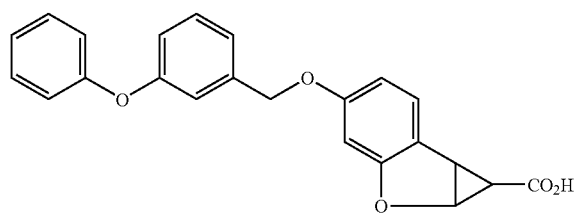
Ex. 26
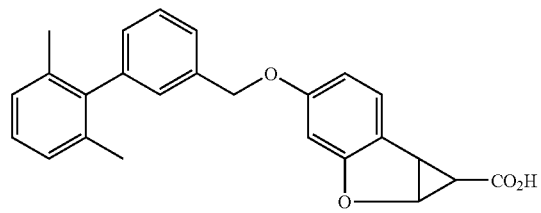
Ex. 27
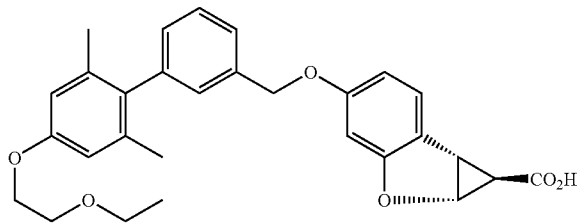
Ex. 28
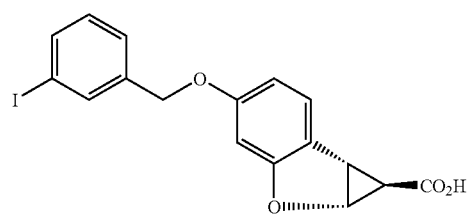
-continued
Ex. 29
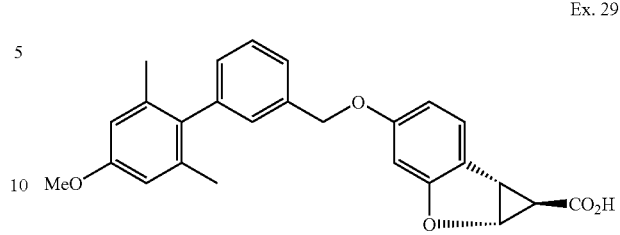
Ex. 30
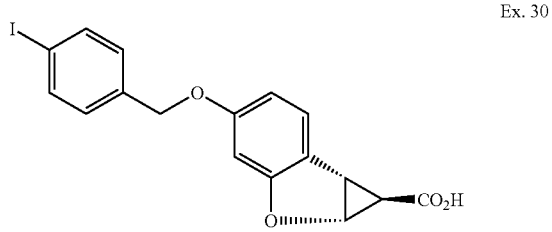
Ex. 31
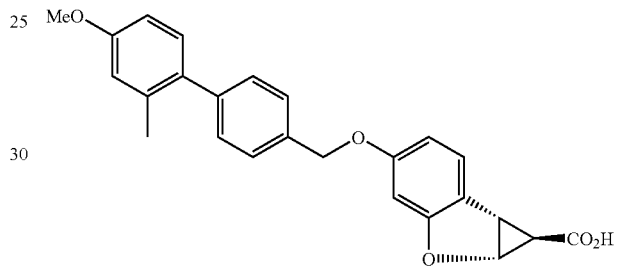
Ex. 32
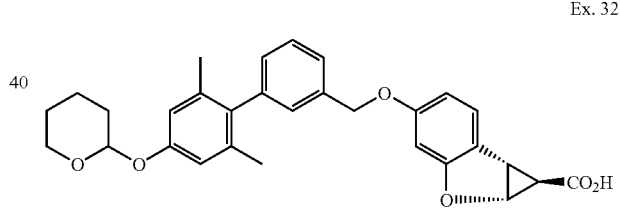
Ex. 33
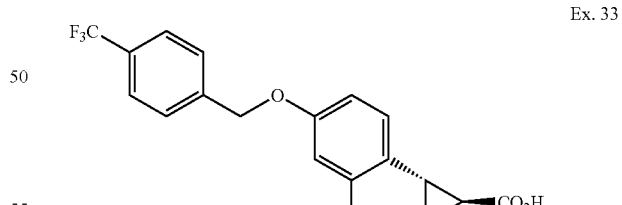
Ex. 34
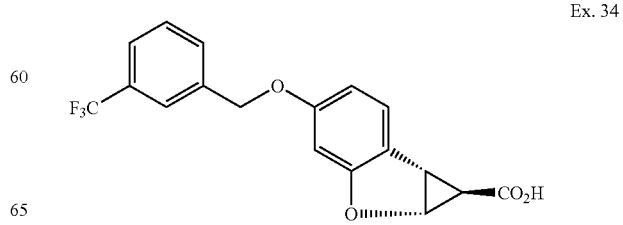

Ex. 35 – Ex. 47 (continued): structural diagrams only.

Ex. 48
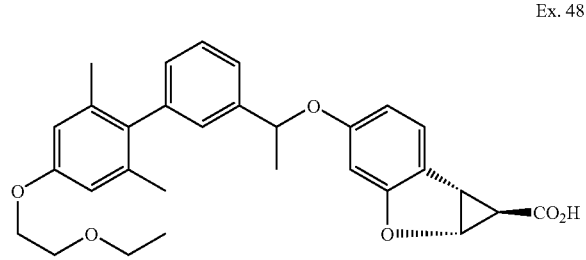
Ex. 49
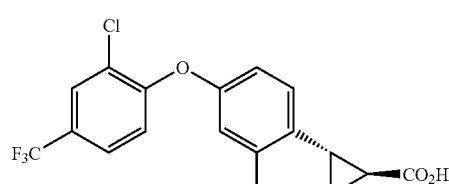
Ex. 54
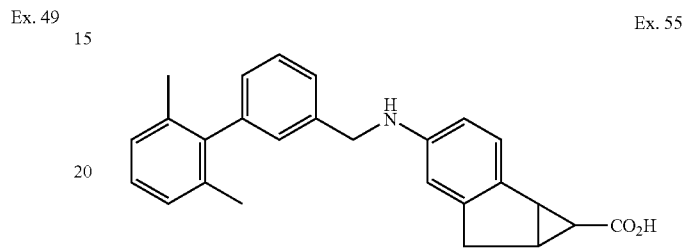
Ex. 55
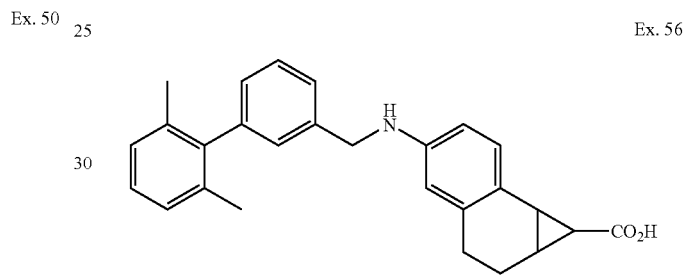
Ex. 50
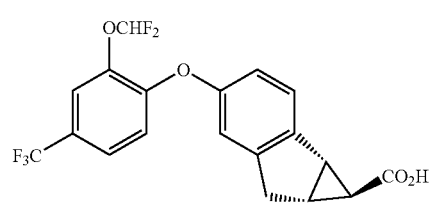
Ex. 56
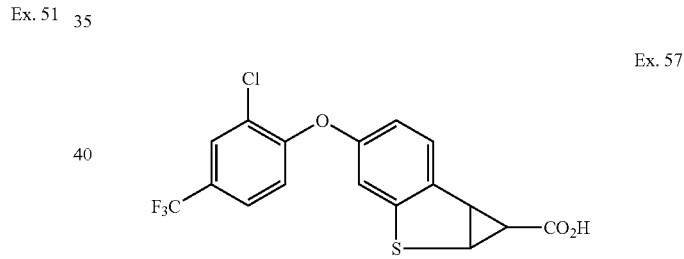
Ex. 51
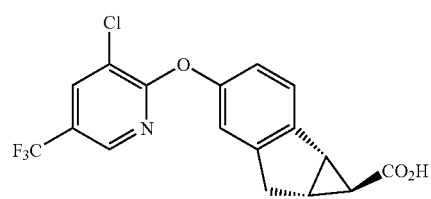
Ex. 57
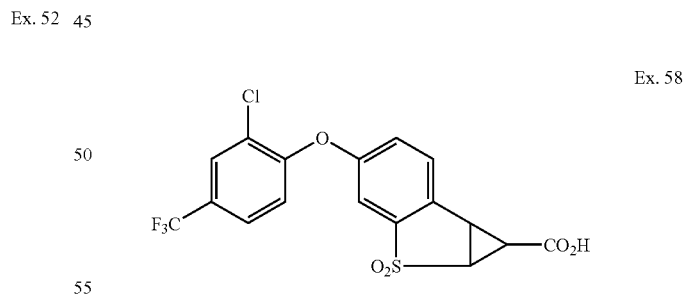
Ex. 52
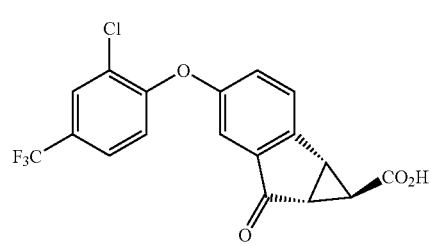
Ex. 58
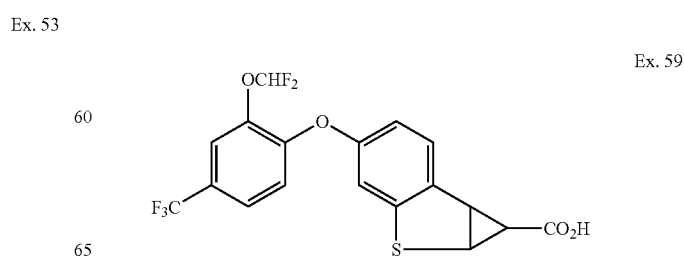
Ex. 53
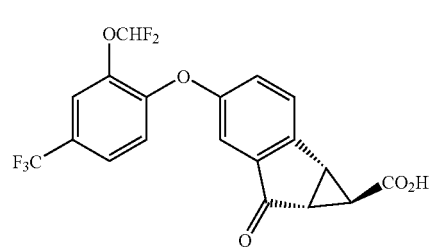
Ex. 59

-continued

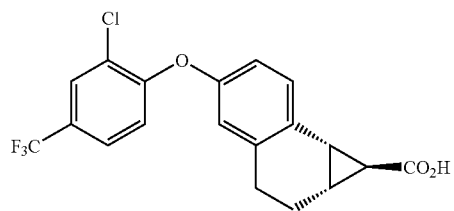
Ex. 60

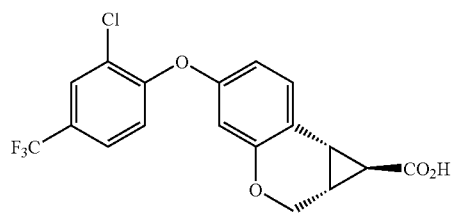
Ex. 61

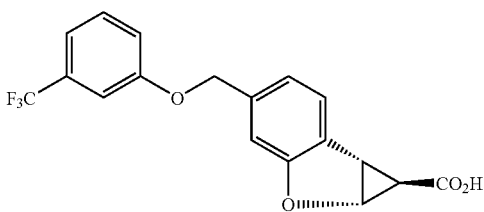
Ex. 62

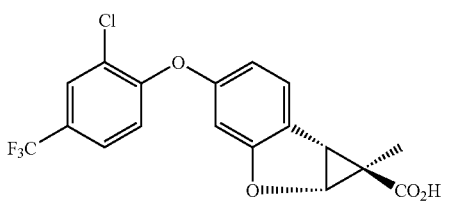
Ex. 63(a)

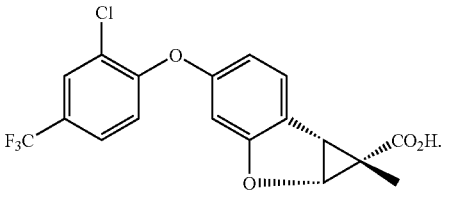
Ex. 63(b)

11. A pharmaceutical composition comprising a compound of claim 1, or a pharmaceutically acceptable salt thereof, and a pharmaceutically acceptable carrier.

12. A method of treating type 2 diabetes mellitus in a patient in need of treatment comprising the administration to the patient of a therapeutically effective amount of the compound of claim 1, or a pharmaceutically acceptable salt thereof.

13. A pharmaceutical composition comprising
(1) a compound of claim 1 or a pharmaceutically acceptable salt thereof;
(2) one or more compounds selected from the group consisting of:
(a) PPAR gamma agonists and partial agonists;
(b) biguanides;
(c) protein tyrosine phosphatase-1B (PTP-1B) inhibitors;
(d) dipeptidyl peptidase IV (DP-IV) inhibitors;
(e) insulin or an insulin mimetic;
(f) sulfonylureas;
(g) α-glucosidase inhibitors;
(h) agents which improve a patient's lipid profile, said agents being selected from the group consisting of (i) HMG-CoA reductase inhibitors, (ii) bile acid sequestrants, (iii) nicotinyl alcohol, nicotinic acid or a salt thereof, (iv) PPARα agonists, (v) cholesterol absorption inhibitors, (vi) acyl CoA:cholesterol acyltransferase (ACAT) inhibitors, (vii) CETP inhibitors, and (viii) phenolic anti-oxidants;
(i) PPARα/γ dual agonists,
(j) PPARδ agonists,
(k) antiobesity compounds,
(l) ileal bile acid transporter inhibitors;
(m) anti-inflammatory agents;
(n) glucagon receptor antagonists;
(o) GLP-1;
(p) GIP-1;
(q) GLP-1 analogs; and
(r) HSD-1 inhibitors; and
(3) a pharmaceutically acceptable carrier.

* * * * *